(12) United States Patent
Myers, III et al.

(10) Patent No.: US 12,023,665 B2
(45) Date of Patent: *Jul. 2, 2024

(54) DEVICES AND METHODS FOR MODIFYING OPTICAL PROPERTIES

(71) Applicant: Pfizer Inc., New York, NY (US)

(72) Inventors: Frank B. Myers, III, Richmond, CA (US); Debkishore Mitra, Fremont, CA (US); John Robert Waldeisen, Berkeley, CA (US); Ivan Krastev Dimov, Union City, CA (US)

(73) Assignee: Pfizer Inc., New York, NY (US)

( * ) Notice: Subject to any disclaimer, the term of this patent is extended or adjusted under 35 U.S.C. 154(b) by 1170 days.

This patent is subject to a terminal disclaimer.

(21) Appl. No.: 16/081,800

(22) PCT Filed: Mar. 14, 2017

(86) PCT No.: PCT/US2017/022305
§ 371 (c)(1),
(2) Date: Aug. 31, 2018

(87) PCT Pub. No.: WO2017/160839
PCT Pub. Date: Sep. 21, 2017

(65) Prior Publication Data
US 2019/0060895 A1 Feb. 28, 2019

Related U.S. Application Data

(60) Provisional application No. 62/307,881, filed on Mar. 14, 2016.

(51) Int. Cl.
*B01L 3/00* (2006.01)
*B01L 7/00* (2006.01)
(Continued)

(52) U.S. Cl.
CPC .......... *B01L 3/502715* (2013.01); *B01L 7/52* (2013.01); *G01N 21/0332* (2013.01);
(Continued)

(58) Field of Classification Search
CPC . G01N 2035/00346; G01N 2035/1034; G01N 2035/00376; G01N 21/0332; G01N 2201/0221; G01N 30/6091
See application file for complete search history.

(56) References Cited

U.S. PATENT DOCUMENTS

D244,555 S    5/1977   Wiedmann
4,310,488 A   1/1982   Rahm et al.
(Continued)

FOREIGN PATENT DOCUMENTS

AU     2003272465 A1   4/2004
CA        2495252 A1   3/2004
(Continued)

OTHER PUBLICATIONS

Extended European Search Report, European Published U.S. Appl. No. 18/857,052, filed May 11, 2021, 10 pages.
(Continued)

*Primary Examiner* — Joseph G. Dauner
(74) *Attorney, Agent, or Firm* — Haley Guiliano LLP

(57) ABSTRACT

Devices and methods for modifying optical properties of biological samples or aspects thereof are provided. The subject methods include generating a reaction product with a device and reacting the reaction product to sufficiently modify an optical property to allow detection of the modified optical property.

83 Claims, 23 Drawing Sheets

(51) Int. Cl.
*G01N 21/03* (2006.01)
*G01N 21/78* (2006.01)
*G01N 21/80* (2006.01)
*G01N 33/50* (2006.01)

(52) U.S. Cl.
CPC ............ *G01N 21/78* (2013.01); *G01N 33/50* (2013.01); *B01L 2200/12* (2013.01); *B01L 2300/041* (2013.01); *B01L 2300/0627* (2013.01); *B01L 2300/123* (2013.01); *B01L 2300/168* (2013.01); *B01L 2300/1822* (2013.01); *B01L 2300/1827* (2013.01); *B01L 2300/1877* (2013.01); *G01N 2021/0346* (2013.01); *G01N 2021/786* (2013.01); *G01N 21/80* (2013.01); *G01N 2201/0221* (2013.01)

(56) References Cited

U.S. PATENT DOCUMENTS

| | | |
|---|---|---|
| 4,379,848 A | 4/1983 | Yeaw |
| 4,624,929 A | 11/1986 | Ullman |
| 4,849,340 A | 7/1989 | Oberhardt |
| 4,859,610 A | 8/1989 | Maggio |
| 4,936,682 A | 6/1990 | Hoyt |
| D334,065 S | 3/1993 | Collister |
| D371,605 S | 7/1996 | Wong et al. |
| 5,580,794 A | 12/1996 | Allen |
| 5,801,062 A | 9/1998 | Sarstedt et al. |
| 5,830,714 A | 11/1998 | Swaminathan et al. |
| 5,837,546 A | 11/1998 | Allen et al. |
| 5,888,826 A | 3/1999 | Ostgaard et al. |
| 5,922,604 A | 7/1999 | Stapleton et al. |
| 5,958,349 A | 9/1999 | Petersen et al. |
| 6,071,394 A | 6/2000 | Cheng et al. |
| 6,074,606 A | 6/2000 | Sayles |
| 6,180,395 B1 | 1/2001 | Skiffington et al. |
| 6,198,107 B1 | 3/2001 | Seville |
| 6,300,142 B1 | 10/2001 | Andrewes et al. |
| 6,336,900 B1 | 1/2002 | Alleckson et al. |
| 6,352,838 B1 | 3/2002 | Krulevitch et al. |
| D456,082 S | 4/2002 | Bouse et al. |
| 6,426,050 B1 | 7/2002 | Pham et al. |
| 6,564,968 B1 | 5/2003 | Terrell et al. |
| 6,565,808 B2 | 5/2003 | Hudak et al. |
| 6,699,384 B1 * | 3/2004 | Lin ............... B01F 25/3142 205/792 |
| 6,817,256 B2 | 11/2004 | Mehra et al. |
| 6,900,059 B1 | 5/2005 | Shinn et al. |
| D507,351 S | 7/2005 | Birnboim |
| 7,156,809 B2 | 1/2007 | Quy |
| 7,256,035 B1 | 8/2007 | Schnell et al. |
| D559,996 S | 1/2008 | Okamoto et al. |
| D560,812 S | 1/2008 | Powell et al. |
| D561,905 S | 2/2008 | Ramel et al. |
| D567,961 S | 4/2008 | Yajima |
| D574,507 S | 8/2008 | Muir et al. |
| 7,438,852 B2 | 10/2008 | Tung et al. |
| 7,452,667 B2 | 11/2008 | Liew et al. |
| D602,599 S | 10/2009 | Xiaowei |
| D608,885 S | 1/2010 | Sneddon et al. |
| D618,351 S | 6/2010 | Hara |
| 7,794,656 B2 | 9/2010 | Liang et al. |
| 7,850,922 B2 | 12/2010 | Gallagher et al. |
| D631,553 S | 1/2011 | Niedbala et al. |
| D659,848 S | 5/2012 | TerMaat et al. |
| D669,375 S | 10/2012 | Kao et al. |
| D675,335 S | 1/2013 | Feuerabend et al. |
| 8,372,353 B2 | 2/2013 | Lee et al. |
| D683,642 S | 6/2013 | Buesser et al. |
| D686,311 S | 7/2013 | Mori |
| D687,564 S | 8/2013 | Yang et al. |
| 8,719,989 B1 | 5/2014 | Qanaei |
| 9,034,606 B2 | 5/2015 | Tanner et al. |
| 9,074,243 B2 | 7/2015 | Tanner et al. |
| 9,074,249 B2 | 7/2015 | Tanner et al. |
| D736,403 S | 8/2015 | Hudson et al. |
| D743,571 S | 11/2015 | Jackson |
| D748,813 S | 2/2016 | Ishiguro et al. |
| D749,420 S | 2/2016 | Maggio |
| 9,278,321 B2 | 3/2016 | Dale et al. |
| D773,069 S | 11/2016 | Curry |
| 9,546,358 B2 | 1/2017 | Tanner et al. |
| D787,682 S | 5/2017 | Ockham et al. |
| D791,952 S | 7/2017 | Florescu et al. |
| 9,739,743 B2 | 8/2017 | Athanasiou et al. |
| D800,912 S | 10/2017 | Uzri et al. |
| 9,815,061 B2 | 11/2017 | Delattre et al. |
| D808,833 S | 1/2018 | Abbott et al. |
| D820,130 S | 6/2018 | Khattak et al. |
| D821,602 S | 6/2018 | Sever et al. |
| 9,999,889 B2 | 6/2018 | Khattak et al. |
| D825,772 S | 8/2018 | Sever et al. |
| D829,336 S | 9/2018 | Wohlstadter et al. |
| D829,337 S | 9/2018 | Klein et al. |
| 10,093,965 B2 | 10/2018 | Toumazou et al. |
| 10,146,909 B2 | 12/2018 | Dimov et al. |
| D838,379 S | 1/2019 | Trump |
| D840,049 S | 2/2019 | Schulz et al. |
| 10,195,606 B2 | 2/2019 | Khattak et al. |
| 10,253,357 B2 | 4/2019 | Mitra et al. |
| 10,272,434 B2 | 4/2019 | Khattak et al. |
| D854,703 S | 7/2019 | Juhlin et al. |
| D855,212 S | 7/2019 | Komuro |
| 10,343,160 B2 | 7/2019 | Lemoine et al. |
| D859,683 S | 9/2019 | Harding et al. |
| D860,472 S | 9/2019 | Blake et al. |
| D865,212 S | 10/2019 | Kakuda et al. |
| D865,218 S | 10/2019 | Mathers et al. |
| 10,449,538 B1 | 10/2019 | Carrano et al. |
| D867,584 S | 11/2019 | Zercher et al. |
| D869,311 S | 12/2019 | Khattak et al. |
| 10,545,161 B2 | 1/2020 | Khattak et al. |
| D874,677 S | 2/2020 | Stamm et al. |
| D875,963 S | 2/2020 | Gruen |
| 10,549,275 B2 | 2/2020 | Myers et al. |
| D879,319 S | 3/2020 | Kakuda et al. |
| D879,320 S | 3/2020 | Kakuda et al. |
| D879,994 S | 3/2020 | Leimkuehler et al. |
| 10,589,267 B2 | 3/2020 | Khattak et al. |
| 10,603,664 B2 | 3/2020 | Khattak et al. |
| D882,110 S | 4/2020 | Klein et al. |
| D883,515 S | 5/2020 | Jenoski et al. |
| D886,901 S | 6/2020 | Hussey et al. |
| 10,843,185 B2 | 11/2020 | Gorin et al. |
| D907,232 S | 1/2021 | Reber et al. |
| D923,797 S | 6/2021 | Parks et al. |
| D928,341 S | 8/2021 | Thimm et al. |
| 11,291,995 B2 | 4/2022 | Mitra et al. |
| 2001/0012612 A1 | 8/2001 | Petersen et al. |
| 2002/0001539 A1 | 1/2002 | DiCesare et al. |
| 2002/0039783 A1 * | 4/2002 | McMillan ............ C12M 47/06 435/259 |
| 2002/0042125 A1 | 4/2002 | Petersen et al. |
| 2002/0114738 A1 | 8/2002 | Wyzgol et al. |
| 2002/0191826 A1 | 12/2002 | Benett et al. |
| 2003/0064526 A1 | 4/2003 | Niedbala et al. |
| 2003/0082632 A1 | 5/2003 | Shumate |
| 2003/0123994 A1 | 7/2003 | Weng et al. |
| 2003/0157503 A1 | 8/2003 | McGarry et al. |
| 2004/0018634 A1 | 1/2004 | Hajizadeh et al. |
| 2004/0052689 A1 | 3/2004 | Yao |
| 2004/0118189 A1 | 6/2004 | Karp et al. |
| 2004/0132218 A1 | 7/2004 | Ho |
| 2004/0166569 A1 | 8/2004 | Marziali et al. |
| 2004/0203174 A1 * | 10/2004 | Jones ............... B01L 3/0241 422/503 |
| 2004/0208792 A1 | 10/2004 | Linton et al. |
| 2004/0209275 A1 | 10/2004 | Liew et al. |
| 2005/0022895 A1 | 2/2005 | Barth et al. |
| 2005/0106066 A1 | 5/2005 | Saltsman et al. |
| 2005/0221281 A1 | 10/2005 | Ho |
| 2006/0078929 A1 | 4/2006 | Bickel et al. |
| 2006/0094004 A1 | 5/2006 | Nakajima et al. |

(56) References Cited

U.S. PATENT DOCUMENTS

| | | |
|---|---|---|
| 2006/0166354 A1 | 7/2006 | Wikswo et al. |
| 2006/0194207 A1 | 8/2006 | Mitani et al. |
| 2006/0245977 A1 | 11/2006 | Bodner |
| 2007/0014695 A1 | 1/2007 | Yue et al. |
| 2007/0092407 A1 | 4/2007 | Xiao et al. |
| 2007/0092975 A1 | 4/2007 | Potyrailo et al. |
| 2007/0166200 A1 | 7/2007 | Zhou et al. |
| 2007/0183934 A1 | 8/2007 | Diercks et al. |
| 2007/0217963 A1 | 9/2007 | Elizarov et al. |
| 2008/0000892 A1 | 1/2008 | Hirano et al. |
| 2008/0038713 A1 | 2/2008 | Gao et al. |
| 2008/0056948 A1 | 3/2008 | Dale et al. |
| 2008/0149840 A1 | 6/2008 | Handique et al. |
| 2008/0204380 A1 | 8/2008 | Shin et al. |
| 2008/0213808 A1 | 9/2008 | Knappe |
| 2008/0233015 A1 | 9/2008 | Turner |
| 2008/0293156 A1 | 11/2008 | Smith |
| 2009/0004732 A1 | 1/2009 | LaBarre et al. |
| 2009/0048115 A1 | 2/2009 | Liew et al. |
| 2009/0071911 A1 | 3/2009 | Folden et al. |
| 2009/0151864 A1 | 6/2009 | Burke et al. |
| 2009/0203973 A1 | 8/2009 | Donoghue et al. |
| 2009/0253130 A1 | 10/2009 | Yoo |
| 2009/0305315 A1 | 12/2009 | Gandola et al. |
| 2009/0308185 A1 | 12/2009 | Wu et al. |
| 2009/0320684 A1* | 12/2009 | Weaver ............... A61M 1/3627 96/12 |
| 2010/0015611 A1 | 1/2010 | Webster et al. |
| 2010/0229956 A1 | 9/2010 | Luyendijk |
| 2010/0315644 A1 | 12/2010 | Egan et al. |
| 2010/0323919 A1 | 12/2010 | Chen et al. |
| 2010/0331219 A1 | 12/2010 | Munenaka |
| 2011/0003330 A1 | 1/2011 | Durack |
| 2011/0005932 A1 | 1/2011 | Jovanovich et al. |
| 2011/0124098 A1 | 5/2011 | Rose et al. |
| 2011/0151432 A1 | 6/2011 | Zappia et al. |
| 2011/0172510 A1 | 7/2011 | Chickering, III et al. |
| 2011/0294112 A1 | 12/2011 | Bearinger et al. |
| 2011/0294205 A1 | 12/2011 | Hukari et al. |
| 2012/0040445 A1 | 2/2012 | Bouma et al. |
| 2012/0100624 A1 | 4/2012 | Hara et al. |
| 2012/0105837 A1 | 5/2012 | Ingber |
| 2012/0115248 A1 | 5/2012 | Ansyln et al. |
| 2012/0123686 A1 | 5/2012 | Xiang et al. |
| 2012/0285562 A1 | 11/2012 | Richardson |
| 2013/0003162 A1 | 1/2013 | Leoni et al. |
| 2013/0112296 A1 | 5/2013 | Lee et al. |
| 2013/0130232 A1 | 5/2013 | Weibel et al. |
| 2013/0130267 A1 | 5/2013 | Luedke et al. |
| 2013/0244241 A1 | 9/2013 | Carrera Fabra et al. |
| 2013/0266948 A1 | 10/2013 | Bird et al. |
| 2013/0280725 A1 | 10/2013 | Ismagilov et al. |
| 2013/0295663 A1 | 11/2013 | Weight et al. |
| 2013/0323738 A1 | 12/2013 | Tanner et al. |
| 2013/0323793 A1 | 12/2013 | Tanner et al. |
| 2014/0031248 A1 | 1/2014 | Tanner et al. |
| 2014/0057210 A1* | 2/2014 | Malik ...................... B01L 7/52 430/320 |
| 2014/0057268 A1 | 2/2014 | Tanner et al. |
| 2014/0073013 A1* | 3/2014 | Gorman ................. B01L 7/52 435/91.2 |
| 2014/0073043 A1 | 3/2014 | Holmes |
| 2014/0170661 A1* | 6/2014 | Lamura ............... G01N 27/414 435/6.12 |
| 2014/0188089 A1 | 7/2014 | Midgette et al. |
| 2014/0228773 A1 | 8/2014 | Burkholz |
| 2014/0242612 A1 | 8/2014 | Wang et al. |
| 2014/0335505 A1 | 11/2014 | Holmes |
| 2014/0356874 A1 | 12/2014 | Bearinger |
| 2015/0024436 A1 | 1/2015 | Eberhart et al. |
| 2015/0111201 A1 | 4/2015 | Ozcan et al. |
| 2015/0132795 A1 | 5/2015 | Griswold et al. |
| 2015/0151300 A1 | 6/2015 | Williams et al. |
| 2015/0154449 A1 | 6/2015 | Ito et al. |
| 2015/0182966 A1 | 7/2015 | Coursey |
| 2015/0218613 A1 | 8/2015 | De Forest et al. |
| 2015/0240293 A1 | 8/2015 | Tanner et al. |
| 2015/0247190 A1 | 9/2015 | Ismagilov et al. |
| 2015/0298118 A1 | 10/2015 | Chard et al. |
| 2015/0321193 A1 | 11/2015 | Sprague et al. |
| 2015/0328638 A1 | 11/2015 | Handique et al. |
| 2015/0359458 A1 | 12/2015 | Erickson et al. |
| 2016/0016171 A1 | 1/2016 | Goel |
| 2016/0077015 A1 | 3/2016 | Holmes et al. |
| 2016/0194685 A1 | 7/2016 | Unger et al. |
| 2016/0216287 A1 | 7/2016 | Holmes et al. |
| 2016/0256870 A1 | 9/2016 | Ismagilov et al. |
| 2016/0275149 A1 | 9/2016 | Majumdar et al. |
| 2016/0288121 A1 | 10/2016 | Ismagilov et al. |
| 2016/0334403 A1 | 11/2016 | Gibbons et al. |
| 2017/0044599 A1 | 2/2017 | Mitra et al. |
| 2017/0327867 A1 | 11/2017 | Dohale et al. |
| 2018/0293350 A1 | 10/2018 | Dimov et al. |
| 2018/0372595 A1 | 12/2018 | Pais et al. |
| 2019/0050988 A1 | 2/2019 | Dimov et al. |
| 2019/0060895 A1 | 2/2019 | Myers, III et al. |
| 2019/0076841 A1 | 3/2019 | Myers, III et al. |
| 2019/0083975 A1 | 3/2019 | Mitra et al. |
| 2019/0094114 A1 | 3/2019 | Myers, III et al. |
| 2019/0309356 A1 | 10/2019 | Mitra et al. |
| 2019/0314810 A1 | 10/2019 | Khattak et al. |
| 2020/0030798 A1 | 1/2020 | Mitra et al. |
| 2020/0122142 A1 | 4/2020 | Myers, III et al. |
| 2020/0164373 A1 | 5/2020 | Khattak et al. |
| 2020/0290035 A1 | 9/2020 | Samsoondar |
| 2020/0323474 A1 | 10/2020 | McIntosh |
| 2021/0378643 A1 | 12/2021 | Roswech et al. |

FOREIGN PATENT DOCUMENTS

| | | |
|---|---|---|
| CN | 101297189 A | 10/2008 |
| CN | 101821619 A | 9/2010 |
| CN | 102395431 A | 3/2012 |
| CN | 102439717 A | 5/2012 |
| CN | 102811754 A | 12/2012 |
| CN | 104374932 A | 2/2015 |
| CN | 104870652 A | 8/2015 |
| CN | 104937108 A | 9/2015 |
| CN | 105142789 A | 12/2015 |
| CN | 105441312 A | 3/2016 |
| CN | 201930535293.7 | 4/2020 |
| EP | 0056241 A1 | 7/1981 |
| EP | 0520408 A2 | 12/1992 |
| EP | 1557673 A1 | 7/2005 |
| EP | 1581652 A2 | 10/2005 |
| EP | 1661988 A1 | 5/2006 |
| EP | 1964927 A1 | 9/2008 |
| EP | 2251435 A1 | 11/2010 |
| EP | 2528687 A2 | 12/2012 |
| EP | 2888374 A1 | 7/2015 |
| EP | 3134553 A1 | 3/2017 |
| IN | 287440 | 8/2019 |
| JP | 62-151198 A | 7/1987 |
| JP | 2001-515216 A | 9/2001 |
| JP | 2002-243748 A | 8/2002 |
| JP | 2004-150804 A | 5/2004 |
| JP | 2006-506979 A | 3/2006 |
| JP | 2006-518449 A | 8/2006 |
| JP | 2007-089591 A | 4/2007 |
| JP | 2008-173218 A | 7/2008 |
| JP | 2010-061383 A | 3/2010 |
| JP | 2010-538801 A | 12/2010 |
| JP | 2013-526867 A | 6/2013 |
| JP | 2013-532488 A | 8/2013 |
| JP | 2013-228350 A | 11/2013 |
| JP | 2014-142361 A | 8/2014 |
| JP | 2015-532593 A | 11/2015 |
| JP | 2016-500002 A | 1/2016 |
| JP | 2016-075687 A | 5/2016 |
| JP | 2016-522676 A | 8/2016 |
| JP | 2017-513531 A | 6/2017 |
| KR | 10-0800436 B1 | 2/2008 |
| KR | 10-2013-0022258 A | 3/2013 |
| KR | 10-1439982 B1 | 9/2014 |

(56) References Cited

FOREIGN PATENT DOCUMENTS

| WO | 1997/011723 A1 | 4/1997 |
| WO | 1997/012681 A1 | 4/1997 |
| WO | 1997/041421 A1 | 11/1997 |
| WO | 99/09042 A2 | 2/1999 |
| WO | 2004/024892 A2 | 3/2004 |
| WO | 2005/012518 A1 | 2/2005 |
| WO | 2008/060604 A2 | 5/2008 |
| WO | 2008/107014 A1 | 9/2008 |
| WO | 2009/033178 A1 | 3/2009 |
| WO | 2009/039259 A1 | 3/2009 |
| WO | 2009/113010 A1 | 9/2009 |
| WO | 2009/125227 A1 | 10/2009 |
| WO | 2010/091080 A2 | 8/2010 |
| WO | 2010/119377 A1 | 10/2010 |
| WO | 2010/132453 A2 | 11/2010 |
| WO | 2011/094577 A2 | 8/2011 |
| WO | 2011/110873 A1 | 9/2011 |
| WO | WO 2011/123064 A1 | 10/2011 |
| WO | 2011/144345 A1 | 11/2011 |
| WO | 2012/018741 A2 | 2/2012 |
| WO | 2012/045889 A1 | 4/2012 |
| WO | 2013/008042 A1 | 1/2013 |
| WO | 2013/080154 A1 | 6/2013 |
| WO | 2014/018828 A1 | 1/2014 |
| WO | 2014/019829 A1 | 2/2014 |
| WO | 2014/020326 A2 | 2/2014 |
| WO | 2014/025415 A2 | 2/2014 |
| WO | 2014/031783 A1 | 2/2014 |
| WO | 2014/055963 A1 | 4/2014 |
| WO | 2014/144548 A2 | 9/2014 |
| WO | 2015/038717 A1 | 3/2015 |
| WO | 2015/112496 A2 | 7/2015 |
| WO | 2015/037281 A1 | 8/2015 |
| WO | 2015/164770 A1 | 10/2015 |
| WO | 2015/184360 A1 | 12/2015 |
| WO | 2017/160836 A1 | 9/2017 |
| WO | 2017/160838 A1 | 9/2017 |
| WO | 2017/160839 A1 | 9/2017 |
| WO | 2017/160840 A1 | 9/2017 |
| WO | 2018/140540 A1 | 8/2018 |
| WO | 2018/185573 A1 | 10/2018 |
| WO | 2019/055135 A1 | 3/2019 |
| WO | WO-2020/180858 A1 | 9/2020 |

OTHER PUBLICATIONS

FDA Approves in-home, rapid results COVID-19 test. Online, published Nov. 18, 2020.
Notification of Transmittal of the International Search Report and the Written Opinion of the International Searching Authority, or the Declaration, Int'l Application No. PCT/US20/20772, dated Jun. 10, 2020, 15 pages.
Canadian Office Action for Application No. 2,944,994, dated Aug. 8, 2019, 3 pages.
European Application No. 17767336.5, Extended European Search Report dated Sep. 26, 2019, 14 pages.
European Application No. 17767337.3, Extended European Search Report dated Sep. 18, 2019, 6 pages.
European Application No. 17767339.9, Extended European Search Report dated Oct. 4, 2019, 11 pages.
European Search Report for Eurpean Patent Application No. EP 19178796.9, dated Oct. 9, 2019, 7 Pages.
Goto., M., et al., "Colorimetric detection of loop-mediated isothermal amplification reaction by using hydroxy naphthol blue", Biotechniques, Mar. 1, 2009, pp. 167-172, vol. 46, No. 3.
Non-Final Office Action for United States U.S. Appl. No. 15/306,240, filed Jul. 24, 2018, 8 pages.
Non-Final Office Action for United States U.S. Appl. No. 16/359,913, filed Oct. 1, 2019, 9 pages.
Non-Final Office Action for United States U.S. Appl. No. 29/674,581, filed Jan. 8, 2020, 11 pages.
Partial Supplemental European Search Report for European Patent Application No. EP 17767338.1, dated Oct. 10, 2019, 15 Pages.
Patent Cooperation Treaty, International Search Report and Written Opinion of the International Searching Authority, International Patent Application No. PCT/US19/55365, dated Feb. 5, 2020, 20 Pages.
Patent Cooperation Treaty, International Search Report and Written Opinion of the International Searching Authority, International Patent Application No. PCT/US2015/027556, dated Sep. 15, 2015, 18 Pages.
Patent Cooperation Treaty, International Search Report and Written Opinion of the International Searching Authority, International Patent Application No. PCT/US2017/022300, dated Jul. 10, 2017, 15 Pages.
Patent Cooperation Treaty, International Search Report and Written Opinion of the International Searching Authority, International Patent Application No. PCT/US2017/022304, dated Jul. 25, 2017, 20 Pages.
Patent Cooperation Treaty, International Search Report and Written Opinion of the International Searching Authority, International Patent Application No. PCT/US2017/022305, dated Jul. 19, 2017, 20 Pages.
Patent Cooperation Treaty, International Search Report and Written Opinion of the International Searching Authority, International Patent Application No. PCT/US2017/022306, dated Jun. 5, 2017, 18 Pages.
PCT International Search Report and Written Opinion for PCT/IB2018/051326, dated Jun. 26, 2018, 15 pages.
PCT International Search Report and Written Opinion for PCT/US2018/044044, dated Sep. 26, 2018, 13 Pages.
Supplementary European Search Report for European Patent Application No. EP 15783787, dated Nov. 28, 2017, 8 Pages.
Supplementary European Search Report for European Patent Application No. EP 17767338.1, dated Jan. 10, 2020, 13 Pages.
Westcott, S.L., et al., "Broadband optical absorbance spectroscopy using a whispering gallery mode microsphere resonator," Review of Scientific Instruments, vol. 79, No. 3, Mar. 13, 2008, 9 Pages.
Foo et al., "Rapid Tests for the Diagnosis of Influenza," Australian Prescriber, vol. 32, No. 3, Jun. 2009, pp. 64-67.
Cao et al., "Microfluidic Chip for Molecular Amplification of Influenza A RNA in Human Respiratory Specimens," PLoS One, Mar. 2012, vol. 7, Issue 3, pp. 1-11.
Anonymous: "Image Enhancement and Verification Tools— ABBYY Mobile Imaging SDK," Jul. 13, 2014, 12 pages.
European Search Report, International Application No. EP18780624, dated Dec. 4, 2020, 10 pages.
Extended European Search Report, European Published Application No. I 15557673 A1, dated May 25, 2021, 21 pages.
Patent Cooperation Treaty, International Search Report and Written Opinion of the International Searcing Authority, International Patent Application No. PCT/US2017/022305, dated Jul. 19, 2017, 20 Pages.
Myers, F. B. et al., A handheld point-of-care genomic diagnostic system, and PLoS One, 2013, and vol. 8(8):e70266, pp. 1-9.
Notification of Transmittal of the International Search Report and the Written Opinion of the International Searching Authority, Int'l Application No. PCT/2021/049178, dated Jan. 14, 2022.

* cited by examiner

Figure 17

| Device | Time to Reaction | | | | | | Intra-Catridge Statistics | |
|---|---|---|---|---|---|---|---|---|
| | 1 | 2 | 3 | 4 | 5 | 6 | Avg | StDev |
| D1 | | 21.7 | 19.3 | 16.8 | 20 | 18.5 | 19.3 | 1.8 |
| D2 | 19.4 | | 18.7 | 16.8 | 19.7 | 19 | 18.7 | 1.1 |
| D3 | 18 | 17 | | 17.6 | 18.9 | 17.9 | 17.9 | 0.7 |
| K1 | | 17.8 | 17.8 | 17.2 | 17.2 | 18.8 | 17.8 | 0.7 |
| K2 | 20.5 | | 16.2 | 15.4 | 16.7 | 17.7 | 17.3 | 2.0 |
| K3 | 18.3 | 17.5 | | 15.8 | 16.1 | 17.1 | 17.0 | 1.0 |
| B4 | 21.2 | 19 | 18.8 | | 15.5 | 16.3 | 18.2 | 2.3 |
| B5 | 18.2 | 18.3 | 18.5 | 15.3 | | 19.2 | 17.9 | 1.5 |
| B6 | 18 | 18.8 | 19.7 | 14.7 | 14.3 | | 17.1 | 2.5 |
| T4 | | 19.2 | 22.3 | 19.7 | 17.9 | 17.5 | 19.2 | 2.2 |
| T5 | 22.8 | 21 | 20.4 | 19.2 | | 17.5 | 20.3 | 1.9 |
| T6 | 22.7 | 21 | 19.2 | | 16.7 | | 19.8 | 2.2 |
| Average | 19.9 | 19.1 | 19.1 | 16.9 | 17.3 | 18.0 | | |
| StDev | 2.0 | 1.6 | 1.6 | 1.7 | 1.8 | 0.9 | | |
| Inter-Catridge Statistics | | | | | | | | |

Figure 18

| Device | Delta E | | | | | | Intra-Catridge Statistics | |
|---|---|---|---|---|---|---|---|---|
| | 1 | 2 | 3 | 4 | 5 | 6 | Avg | StDev |
| D1 | | 46.4 | 61.1 | 63.6 | 57 | 56.5 | 56.9 | 6.6 |
| D2 | 36.6 | 43.4 | 36.8 | 44.1 | 35.8 | 38.9 | 38.4 | 3.4 |
| D3 | 43.9 | 43.3 | | 52.1 | 49.9 | 47.8 | 47.4 | 3.8 |
| K1 | 37.2 | 64.3 | 63.9 | 63.3 | 66.7 | 59.1 | 63.5 | 2.8 |
| K2 | 46.6 | 47.5 | 44.3 | 52.3 | 54.2 | 51 | 47.8 | 7.0 |
| K3 | 44.8 | 53 | 55 | 56.1 | 56.8 | 51.3 | 51.7 | 4.7 |
| B4 | 47.1 | 50.3 | 50.7 | 52.1 | 59 | 52.2 | 52.8 | 5.2 |
| B5 | 42.5 | 47.4 | 43.5 | 53.7 | | 42.8 | 48.6 | 3.7 |
| B6 | | 58.5 | | | 50.8 | | 47.6 | 4.8 |
| T4 | 33.1 | 36.1 | 34.5 | 34.5 | 62.7 | 61.1 | 60.8 | 2.1 |
| T5 | | 32.3 | 38.9 | 42.7 | | 35.2 | 34.7 | 1.1 |
| T6 | 29.4 | | | | 46.1 | | 37.9 | 7.0 |
| Average | 40.1 | 47.9 | 47.6 | 51.5 | 53.9 | 49.6 | | |
| StDev | 6.3 | 9.5 | 10.6 | 9.0 | 8.8 | 8.5 | | |
| Inter-Catridge Statistics | | | | | | | | |

DEVICES AND METHODS FOR MODIFYING OPTICAL PROPERTIES

RELATED APPLICATIONS

This application is a 35 U.S.C. 371 national stage filing of International Application No. PCT/US2017/022305, filed on Mar. 14, 2017, which claims priority from U.S. Provisional Patent Application No. 62/307,881 filed on Mar. 14, 2016, which are hereby incorporated by reference in their entireties.

INTRODUCTION

Biological assays are used to determine one or more characteristics of biological samples. Such assays can qualitatively assess and/or quantitatively measure the presence, amount and/or functional activity of one or more analytes in a biological sample. Such an assessment can be made based on a change or lack of a change occurring in the assay. For example, a change in transmittance and/or color of a biological sample occurring under particular conditions during an assay can indicate one or more characteristics of the sample being evaluated.

SUMMARY OF THE INVENTION

Devices and methods for modifying optical properties of biological samples or aspects thereof are provided. The subject methods include generating a reaction product with a device and reacting the reaction product to sufficiently modify an optical property to allow detection of the modified optical property, such as by an un-assisted human eye.

The subject disclosure includes biological sample assay optical property modifying devices. In some versions, a biological sample employed in an assay device is a nucleic acid amplification sample. Various embodiments of the disclosed devices include a sample receiving cartridge having one or more reaction chambers, e.g., microfluidic reaction chambers, for receiving a biological sample and each including an optical property modifying reagent, e.g., an enzyme-linked immunosorbent assay (ELISA) reagent, and/or a nucleic acid amplification composition. A sample receiving cartridge can include a sample inlet operatively connecting each of the one or more reaction chambers.

In some versions of the devices, each of the one or more reaction chambers includes a first opening on a first side of the sample receiving cartridge and a second opening on a second side of the sample receiving cartridge, wherein the first side is opposite the second side and the adhesive layer forms a wall of each of the one or more reaction chambers by sealing each second opening. In various aspects of the devices, the devices include a selective venting element, e.g., a polyethylene selective venting element, forming a wall of each of the one or more reaction chambers. In some embodiments, a selective venting element seals each first opening. According to various embodiments, a sample receiving cartridge is transparent and/or includes a polymeric material such as polyethylene.

In some versions, the devices also have a substrate e.g., a printed circuit board substrate, which can include a heating element and/or a power source operatively coupled to the heating element. Heating elements are elements that are configured to generate thermal energy and can be proximate to one or more reaction chambers. By "proximate" is meant close to. In some versions, heating elements may be configured for heating a sample in one or more reaction chambers. A substrate can also include a control unit and/or a sensor for detecting presence of the sample in the one or more reaction chambers. In some versions, a control unit activates a heating element to heat a sample in the one or more reaction chambers when a sensor detects the sample in the one or more reaction chambers. A control unit can also be configured to perform a colorimetric analysis of a sample in the one or more reaction chambers. The substrate can also include a light source that emits light when the sensor detects the sample in the one or more reaction chambers.

The subject devices also can include an adhesive layer operatively connecting the sample receiving cartridge and the substrate and thereby forming a wall of each of the one or more reaction chambers. An adhesive layer, in some variations, is composed of a first layer laminated with a second layer. An adhesive layer can be transparent, reflective and/or include one or more adhesive, e.g., acrylic adhesive. An adhesive layer can also be opaque and/or white. In some versions, an adhesive layer does not include an acid.

The subject devices also, in some embodiments, include a housing. The housing can include a first portion and a second portion mateable with the first portion to encapsulate the sample receiving cartridge, substrate and adhesive layer. Embodiments of the subject devices can be hand-held devices. As such, in some versions, housings have a volume of 300 $cm^3$ or less.

The subject disclosure also includes methods of modifying an optical property in a biological sample assay. Such methods include transmitting a biological sample into one or more reaction chambers of a sample receiving cartridge of a biological sample assay optical property modifying device, wherein the chambers each include an optical property modifying reagent, and thereby generating a reaction mixture. In some aspects, transmitting a biological sample into the one or more reaction chambers includes flowing the sample through a sample inlet operatively connecting each of the one or more reaction chambers. Transmitting a biological sample into one or more reaction chambers can also include flowing a gas, e.g., air, through a selective venting element.

According to some aspects, a substrate includes a sensor, and transmitting a biological sample into one or more reaction chambers includes detecting the sample in the one or more reaction chambers with the sensor. A substrate can also include a light source, and transmitting a biological sample into one or more reaction chambers can include activating the light source to emit light. Also, in some aspects, an optical property modifying device includes a housing having a first portion including a receptacle, and a second portion mateable with the first portion to encapsulate the sample receiving cartridge and the heating element. In such embodiments, transmitting the biological sample into the one or more reaction chambers can include flowing the sample through the receptacle.

The methods also include heating the reaction mixture with a heating element of the device and thereby generating a reaction product. In some aspects, the heating accelerates a nucleic acid amplification reaction comprising the nucleic acid and the amplification composition, the reaction generating an amplified nucleic acid and the reaction product, wherein the reaction product comprises a plurality of protons.

According to some embodiments, the methods include reacting the reaction product with the optical property modifying reagent, wherein the reacting sufficiently modifies an optical property of the optical property modifying reagent to allow detection of the modified optical property, such as by an un-assisted human eye and/or a device, such as an optical property detecting device, such as device including a camera.

In some aspects of the methods, an optical property modifying device includes a selective venting element. In such aspects, the methods can include containing the sample in the one or more reaction chambers with the selective venting element.

Modifying an optical property of the biological sample can also, in various aspects, include performing a colorimetric analysis of a sample in the one or more reaction chambers with a control unit. Such an analysis can be performed on the reaction product after reacting it with the optical property modifying reagent. In some versions, a sample receiving cartridge is transparent, and performing a colorimetric analysis includes detecting one or more characteristics of light transmitted through the sample receiving cartridge. The methods can also include performing a colorimetric analysis of a reaction product after reacting it with an optical property modifying reagent, wherein the adhesive layer is opaque white, and wherein performing the colorimetric analysis includes visually inspecting the chambers to detect a modified optical property.

In some aspects, each of the one or more reaction chambers includes a first opening on a first side of the sample receiving cartridge and a second opening on a second side of the sample receiving cartridge, wherein the first side is opposite the second side. According to some versions of the methods, an optical property modifying device includes an adhesive layer forming a wall of each of the one or more reaction chambers by sealing each second opening, and wherein transmitting a biological sample into one or more reaction chambers includes containing the sample in the one or more reaction chambers with the adhesive layer.

Also provided herein are methods of modifying an optical property with the biological sample assay optical property modifying device. Such methods include generating a reaction product from a biological sample. Such methods can also include reacting the reaction product with the optical property modifying reagent, wherein the reacting sufficiently modifies an optical property of the optical property modifying reagent to allow detection of the modified optical property by an un-assisted human eye.

Methods of manufacturing a biological sample assay optical property modifying device are also included. Such methods can include operatively coupling the sample receiving cartridge and the substrate with the adhesive layer. In some versions, an adhesive layer includes a first side and a second side opposite the first side, and wherein operatively coupling the sample receiving cartridge and substrate includes adhesively attaching the sample receiving cartridge to the first side and the substrate to the second side.

BRIEF DESCRIPTION OF THE SEVERAL VIEWS OF THE DRAWINGS

FIG. 17 provides nucleic acid amplification reaction times across six different reaction chambers in an optical property modifying device according to embodiments of the subject disclosure.

FIG. 18 provides color changes, as measured using the CIE94 Delta-E scale, resulting from nucleic acid amplification reactions across six different reaction chambers in an optical property modifying device according to embodiments of the subject disclosure.

DETAILED DESCRIPTION OF THE INVENTION

Figure 1:
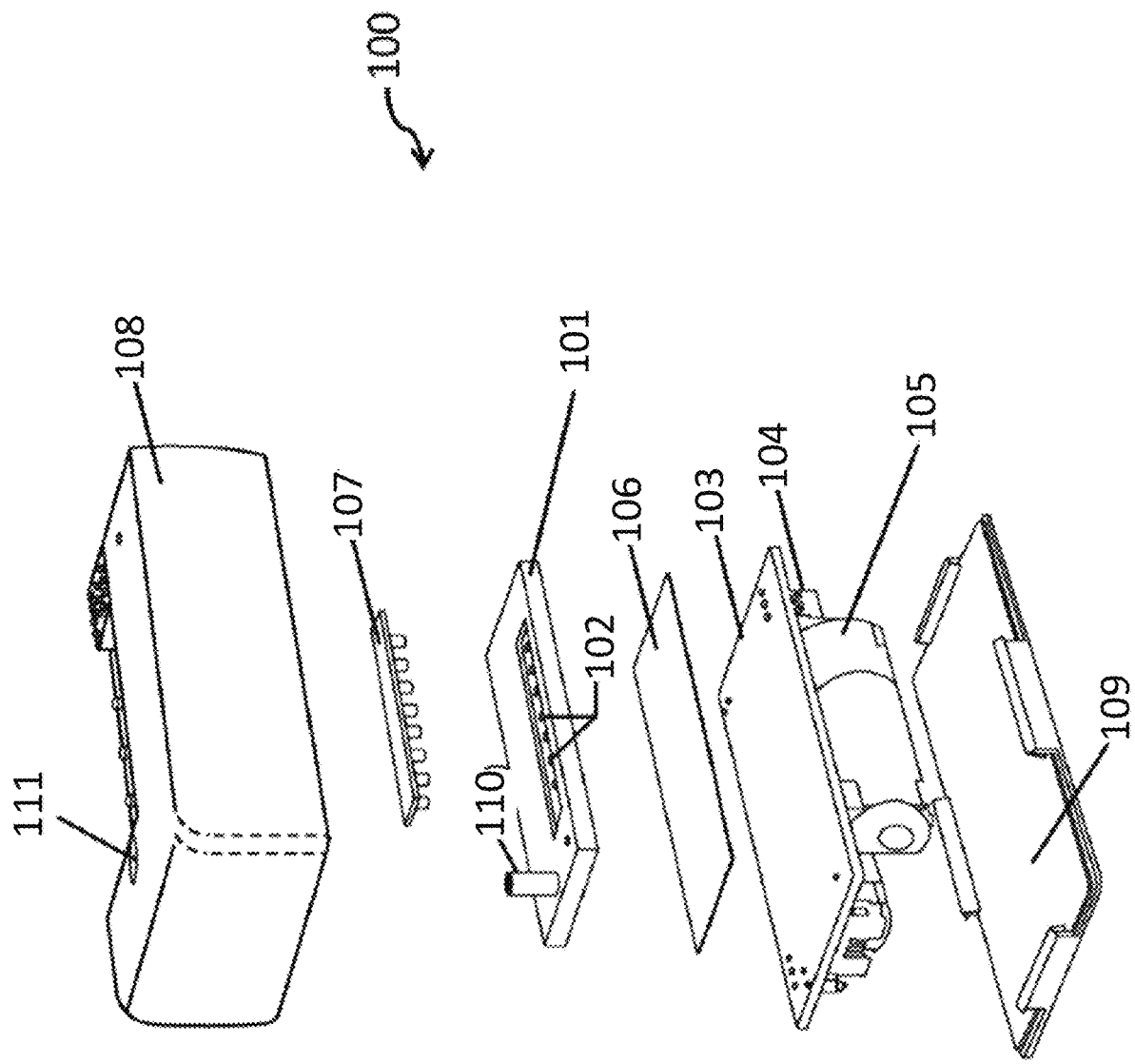
FIG. 1 provides a perspective view of a device according to embodiments of the subject disclosure.

Devices and methods for modifying optical properties of biological samples or aspects thereof are provided. The subject methods include generating a reaction product with a device and reacting the reaction product to sufficiently modify an optical property to allow detection of the modified optical property, such as by an un-assisted human eye.

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention.

Certain ranges can be presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided can be different from the actual publication dates which can need to be independently confirmed.

It is noted that, as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Additionally, certain embodiments of the disclosed devices and/or associated methods can be represented by drawings which can be included in this application. Embodiments of the devices and their specific spatial characteristics and/or abilities include those shown or substantially shown in the drawings or which are reasonably inferable from the drawings. Such characteristics include, for example, one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal; distal), and/or numbers (e.g., three surfaces; four surfaces), or any combinations thereof. Such spatial characteristics also include, for example, the lack (e.g., specific absence of) one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal), and/or numbers (e.g., three surfaces), or any combinations thereof.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

In further describing the subject invention, subject devices for use in practicing the subject devices will be discussed in greater detail, followed by a review of associated methods.

Definitions

Terms used in the claims and specification are defined as set forth below unless otherwise specified.

The term "colorimetry" or "colorimetric" refers to techniques of quantifying or otherwise observing colored compound concentrations in solution. "Colorimetric detection" refers to any method of detecting such colored compounds and/or the change in color of the compounds in solution. Methods can include visual observation, absorbance measurements, or fluorescence measurements, among others.

The term "halochromic agent" refers to a composition that changes color upon some chemical reaction. In particular, a halochromic agent can refer to a composition that changes color with a pH change. Different halochromic agents can change colors over different pH transition ranges.

The term "transition pH range" or "pH transition range" refers to a pH range over which the color of a particular sample or compound changes. A specific transition pH range for a sample can depend on a halochromic agent in the sample (see above).

The term "nucleic acid amplification" or "amplification reaction" refers to methods of amplifying DNA, RNA, or modified versions thereof. Nucleic acid amplification includes several techniques, such as an isothermal reaction or a thermocycled reaction. More specifically, nucleic acid amplification includes methods such as polymerase chain reaction (PCR), loop-mediated isothermal amplification (LAMP), strand displacement amplification (SDA), recombinase polymerase amplification (RPA), helicase dependent amplification (HDA), multiple displacement amplification (MDA), rolling circle amplification (RCA), and nucleic acid sequence-based amplification (NASBA). The term "isothermal amplification" refers to an amplification method that is performed without changing the temperature of the amplification reaction. Protons are released during an amplification reaction: for every deoxynucleotide triphosphate (dNTP) that is added to a single-stranded DNA template during an amplification reaction, one proton (H f) is released.

The term "sufficient amount" means an amount sufficient to produce a desired effect, e.g., an amount sufficient to modulate protein aggregation in a cell.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

Devices

Aspects of the subject disclosure include biological sample assay optical property modifying devices. As used herein, a "biological sample" is a sample containing a quantity of organic material, e.g., one or more organic molecules, such as one or more nucleic acids e.g., DNA and/or RNA or portions thereof, which can be taken from a subject. As such, a "biological sample assay" is test on a biological sample which is performed to evaluate one or more characteristics of the sample. In some aspects a biological sample is a nucleic acid amplification sample, which is a sample including one or more nucleic acids or portions thereof which can be amplified according to the subject embodiments.

A biological sample can be collected from a subject and include one or more cells, such as tissue cells of the subject. As used herein, the term "tissue" refers to one or more aggregates of cells in a subject (e.g., a living organism, such as a mammal, such as a human) that have a similar function and structure or to a plurality of different types of such aggregates. Tissue can include, for example, organ tissue, muscle tissue (e.g., cardiac muscle; smooth muscle; and/or skeletal muscle), connective tissue, nervous tissue and/or epithelial tissue. Tissue can, in some versions, include cells from the inside of a subject's cheek and/or cells in a subject's saliva.

As noted above, a biological sample can be collected from a subject. In certain embodiments, a subject is a "mammal" or a "mammalian" subject, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the subject is a human. The term "humans" can include human subjects of both genders and at any stage of development (e.g., fetal, neonates, infant, juvenile, adolescent, and adult), where in certain embodiments the human subject is a juvenile, adolescent or adult. While the devices and methods described herein can be applied in association with a human subject, it is to be understood that the subject devices and methods can also be applied in association with other subjects, that is, on "non-human subjects."

A biological sample, as referred to herein, can in some versions be a prepared biological sample. A prepared biological assay sample is a biological assay sample which has been processed for example by exposing the sample to a preparation solution, such as a solution including a lysing agent, such as a detergent. Accordingly, in some embodiments, a biological sample is a lysate. Such preparation can enable the prepared biological sample to react, for example, with an amplification composition and/or an optical property modifying reagent upon exposure thereto. The exposure can include lysing cells of the sample with a lysing agent of the preparation solution and/or extracting nucleic acids therefrom. Such extracted nucleic acids can be released into a resulting prepared sample solution. In some embodiments, a step of extracting genomic deoxyribonucleic acid (DNA) from a biological sample is included. Where desired, the preparation solution is a nucleic acid amplification preparation solution and exposure to the solution prepares nucleic acids of the sample for amplification, e.g., isothermal amplification.

Also, as used herein, the phrase "optical property," refers to one or more optically-recognizable characteristics, such as a characteristic resulting from wavelength and/or frequency of radiation, e.g., light, emitted from an aspect, such as color, fluorescence, phosphorescence, etc. As such, modifying an optical property refers to changing such a characteristic.

An embodiment of a biological sample assay optical property modifying device for use in practicing the subject methods is provided in FIG. 1. In various embodiments, the device 100 includes a sample receiving cartridge 101 including one or more reaction chambers 102 for receiving a biological sample and each including an optical property modifying reagent. Such a device 100 can also include a substrate 103 including a heating element 104 and/or a power source 105 operatively coupled to the heating element 104.

By "operatively coupled," "operatively connected," and "operatively attached" as used herein, is meant connected in a specific way that allows the disclosed devices to operate and/or methods to be carried out effectively in the manner described herein. For example, operatively coupling can include removably coupling or fixedly coupling two or more aspects. Operatively coupling can also include fluidically and/or electrically and/or mateably and/or adhesively coupling two or more components. Also, by "removably coupled," as used herein, is meant coupled, e.g., physically and/or fluidically and/or electrically coupled, in a manner wherein the two or more coupled components can be un-coupled and then re-coupled repeatedly.

As provided in FIG. 1, the device 100 also includes an adhesive layer 106. Such a layer 106 can operatively connect the sample receiving cartridge 101 and the substrate 103 and thereby form a wall of each of the one or more reaction chambers 102. The device 100 also includes a selective venting element 107 which also forms a wall of each of the one or more reaction chambers 102. Also, as provided in FIG. 1, the device includes a housing composed of a first portion 108 including a receptacle 111 and a second portion 109 mateable with the first portion to encapsulate the sample receiving cartridge 101, substrate 103 and adhesive layer 106. In such a configuration, the sample receiving cartridge 101, substrate 103 and adhesive layer 106 can all be disposed between at least two opposite portions, e.g., walls, of the first portion 108.

Figure 2:
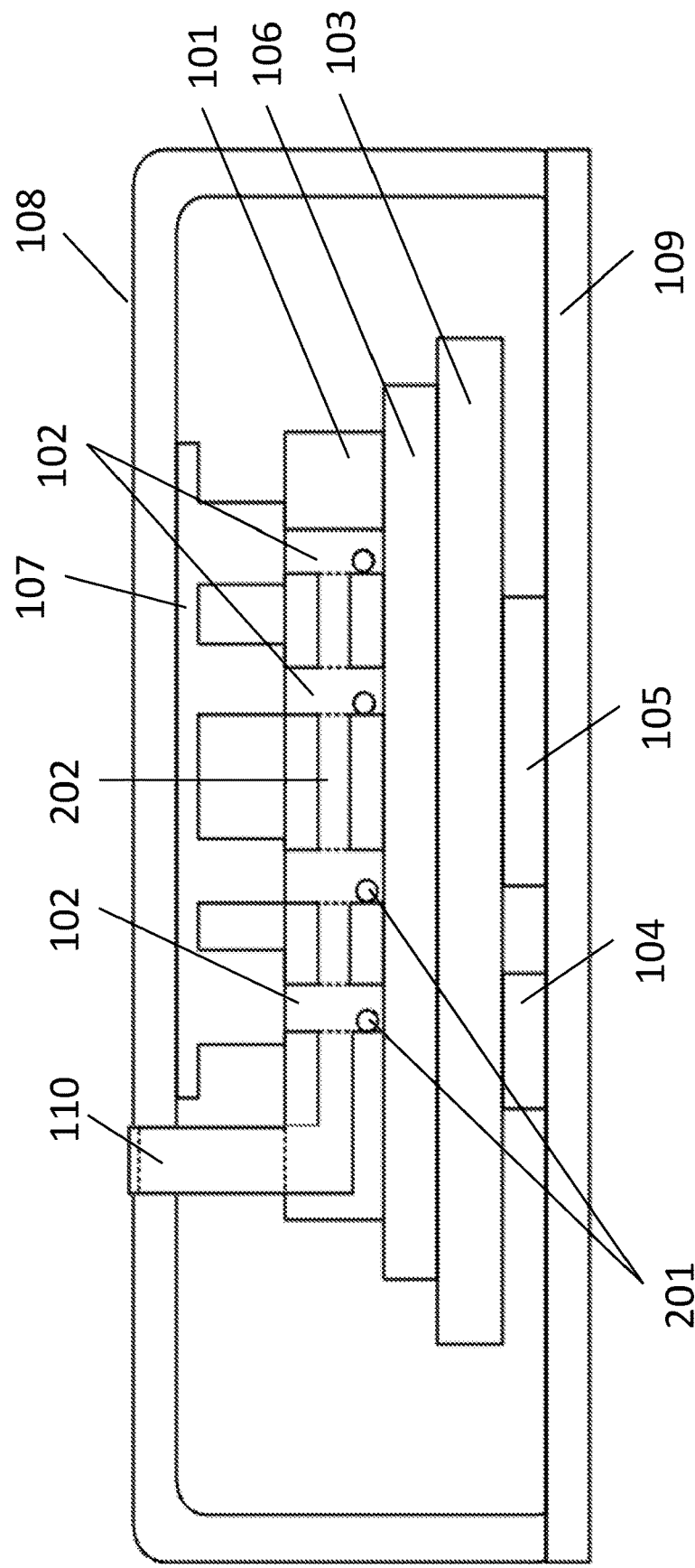
FIG. 2 provides a representative cross sectional view of a device according to embodiments of the present disclosure.

Whereas the embodiment provided in FIG. 1, is shown in an unassembled conformation for illustrative purposes, a representative embodiment of the device is provided in FIG. 2. FIG. 2 specifically provides a representative illustration of many of the same elements as FIG. 1 in an assembled conformation. FIG. 2 also specifically shows an optical property modifying reagent 201 within each of the one or more reaction chambers 102. Also shown are conduits 202 operatively coupling each of the one or more reaction chambers 102 with one another and/or with a sample inlet 110.

In various embodiments, a sample receiving cartridge can include one or more, such as a plurality, such as two or more, such as 5 or more, such as 10 or more, such as 15 or more, such as 20 or more, such as 50 or more reaction chambers. A sample receiving cartridge can include 50 or less, such as 20 or less, such as 15 or less, such as 10 or less, such as 5 or less reaction chambers. A sample receiving cartridge can include from 1 to 25, such as from 1 to 20, such as from 1 to 15, such as from 1 to 10 such as from 1 to 5, reaction chambers, or from 2 to 20, such as from 2 to 15, such as from 5 to 15 reaction chambers, wherein each range is inclusive. As used herein, "inclusive" refers to a provided range including each of the listed numbers. Unless noted otherwise herein, all provided ranges are inclusive. A sample receiving cartridge can include 1, 2, 3, 4, 5, 6, 7, 8, 9, 10, 11, 12, 13, 14, 15, 16, 17, 18, 19, or 20 or more reaction chambers.

Each reaction chamber can be shaped as a cylinder, rectangular box, cube, or any combination thereof. For example, each reaction chamber can extend from a first opening in a first surface of a sample receiving cartridge, through the cartridge to a second opening in a second surface of a sample receiving cartridge opposite the first. Also, as noted herein, each opening can be sealed by a portion, e.g., surface, of a component, such as an adhesive layer and/or a selective venting element, each forming a wall of a reaction chamber. For example an adhesive layer can form a wall of a reaction chamber at a first end and/or a selective venting element can form a wall of the reaction chamber at a second end opposite the first. In doing so, the adhesive layer can seal each second opening and/or the selective venting element can seal each first opening.

Each reaction chamber can also be a microfluidic reaction chamber. The subject reaction chambers can each have a volume of 1 µL to 1000 µL, such as 1 µL to 100 µL, such as 1 µL to 50 µL, such as 10 µL to 30 µL, such as 15 µL to 30 µL, or 50 µL or less, or 30 µL or less. As such, each reaction chamber is configured to receive contents, e.g., contents including solid and/or liquid media, such as a biological sample and/or optical property modifying reagents, therein having a volume equal to or less than any of the provided volumes.

In various embodiments, each reaction chamber can include, such as contain within a chamber, one or more optical property modifying reagent. Such optical property modifying reagents can include, for example, pH sensitive dyes, fluorescent dyes, FRET dyes, micro and nano particles, fluorescent proteins, colorimetric substrates, enzymes and reagents, plasmonic structures, precipitation reagents and substrates, or any combination thereof.

In some versions, the optical property modifying reagent is or includes an enzyme-linked immunosorbent assay (ELISA) reagent. In some aspects, the ELISA reagent is selected from the group consisting of alkaline phosphatase, horseradish peroxidase, β-galactosidase, BCIP/NBT (5-bromo-4-chloro-3-indolyl-phosphate/nitrobluetetrazolium), TMB (3,3', 5,5' tetramethylbenzidine), DAB (3,3', 4,4' diaminobenzidine), 4CN (4-chloro-1-naphthol). TMB (dual function substrate), ABTS (2,2'-azino-di [3-ethylbenzthiazoline] sulfonate), OPD (o-phenylenediamine), MUG (4-methylumbelliferyl galactoside), HPA (hydroxyphenylacetic acid), and HPPA (3-p-hydroxyphenylproprionic acid).

Also, in some versions, an optical property modifying reagent, can be stored in a sample receiving cartridge in dry, e.g., lyophilized, form. As such, moving a biological sample, e.g., a fluid biological sample, into a reaction chamber can include mixing the biological sample and the optical property modifying reagent and/or hydrating the optical property modifying reagent. According to some embodiments, an optical property of an optical property modifying reagent is changed due to the presence or the absence of a particular marker in a biological sample when the biological sample or one or more aspect thereof, such as one or more amplified nucleic acids and/or protons, are exposed to the optical property modifying reagent.

In some versions, performing an optical property modification includes changing the pH of reaction chamber contents by performing a reaction. An optical property modifying reagent can produce a modification based on the location and extent of such a pH change.

In some instances, each reaction chamber can include, such as contain within a chamber, one or more nucleic acid amplification composition. Such nucleic acid amplification composition can include, for example, one or more primers, deoxynucleotides (dNTPs), and/or polymerases, Trizma pre-set crystals (Tris buffer, pH 8.8; Sigma, cat. no. T9443), Potassium chloride (KCl; Wako Pure Chemicals, cat. no. 163-03545), Magnesium sulfate heptahydrate (MgSO4; Wako Pure Chemicals, cat. no. 137-00402), Ammonium sulfate ((NH4)2SO4; Kanto Chemical, cat. no. 01322-00), TWEEN® 20 (Tokyo Chemical Industry, cat. no. T0543), Betaine solution (Betaine, 5 M; Sigma, cat. no. B0300), Calcein (DOJINDO, cat. no. 340-00433) plus all other optical modification reagents as discussed above, Manganese(II) chloride tetrahydrate (MnCl2; Wako Pure Chemicals, cat. no. 133-00725), Agarose S, EtBr solution, template nucleic acids, or any combination thereof. In addition, in some versions, a nucleic acid amplification composition, can be stored in a sample receiving cartridge in dry, e.g., lyophilized, form. As such, moving a biological sample, e.g., a fluid biological sample, into a reaction chamber can include mixing the biological sample and the nucleic acid amplification composition and/or hydrating the nucleic acid amplification composition.

In some versions of the subject disclosure, the nucleic acid amplification composition can include one or more buffer and/or water. A nucleic acid amplification composition is a solution which prepares a biological sample such that one or more nucleic acid thereof can be amplified, e.g., amplified isothermally.

A nucleic acid amplification composition can be a reagent which prepares a biological sample for amplification with an isothermal amplification protocol including: transcription mediated amplification, strand displacement amplification, nucleic acid sequence-based amplification, rolling circle amplification, loop-mediated isothermal amplification, isothermal multiple displacement amplification, helicase-dependent amplification, circular helicase-dependent amplification, single primer isothermal amplification, loop-mediated amplification, or any combination thereof.

In various embodiments, the amplification according to the subject embodiments is reverse transcriptase loop-mediated amplification (RT-LAMP). In various aspects, RT-LAMP is an isothermal gene amplification procedure in which the reaction can be processed at a constant temperature, e.g., 63° C., by one type of enzyme, e.g., Bst polymerase, in a single step. RT-LAMP, in various aspects, uses six primers that recognize eight regions on a target nucleic acid. In various embodiments, the sensitivities and specificities of the RT-LAMP technique is higher than those associated with performing a polymerase chain reaction (PCR). The RT-LAMP method is also fast, producing a signal from a few copies of RNA in 60 minutes, or less, 45 minutes or less, 30 minutes or less, or 15 minutes or less. RT-LAMP can also not require any special reagents. Also, according to the subject embodiments a "detection" according to the subject embodiments is a detection of one or more aspects, such as specific pathogenic genetic markers in samples. Amplification according to the subject embodiments can also be performed by applying PCR.

Also, as noted above, in some versions, the sample receiving cartridges also include one or more conduits operatively, e.g., fluidically, connecting each or any combination of the one or more reaction chambers with one another and/or with a sample inlet. Each of the one or more conduits can be shaped as a cylinder or a quadrilateral prism and can have dimensions including a length of 10 m or less, such as 1 m or less, such as 10 cm or less, such as 1 mm or less, and/or have a diameter, width and/or height of 100 mm or less, such as 10 mm or less, such as 1 mm or less, such as 0.1 mm or less, such as 10 micrometers or less. Each of the one or more conduits can also have a volume of 1000 µL, or less, such as 10 µL, or less, such as 1 µL or less, such as 0.1 µL, or less, such as 1 nL or less. Movement, e.g., diffusion, of a liquid or a component thereof from one reaction chamber to another is substantially prevented by the conduits due to the length of the conduits. Accordingly, each of the reaction chambers is isolated from one another and the amount of such movement over the duration of an assay is negligible in influencing an assay result.

In addition, where desired, the sample receiving cartridges also include one or more inlets operatively, e.g., fluidically, connecting each or any combination of the one or more reaction chambers with one another and/or with an environment external to the device. Each of the one or more inlets can be shaped as a tube extending from a surface of the microfluidic cartridge through the cartridge. A first end of the inlet can extend from a surface of the cartridge to an opening in the housing and be configured for receiving a fluid, e.g., a biological sample, therein. A second end, or a plurality of second ends, opposite the first end of the inlet, can each terminate at a reaction chamber and be configured for conveying fluid, e.g., a biological sample, to the chamber. Also, a second end, or a plurality of second ends, opposite the first end of the inlet, can each terminate at a conduit, as described herein. An inlet can also be microfluidic and can be configured such that a fluid flows automatically therethrough upon introduction at a first end. An inlet can have a diameter ranging from 1 µm to 10 cm and can also have a volume of 1 µL to 1 mL. Furthermore, in some versions, inlets can include one or more connectors, e.g., fluidic connectors, e.g., luer connectors, such as at an end, for operatively connecting to one or more reciprocating connectors, e.g., fluidic connectors, e.g., luer connectors, such as one or more connector of a sample preparation device.

Also, in various embodiments, the sample receiving cartridges or portions thereof, e.g., substrates, are composed of one or more materials including, for example, polymeric materials (e.g., materials having one or more polymers including, for example, plastic and/or rubber) and/or metallic materials. Materials of which any of the device components including sample receiving cartridges or portions thereof described herein can be composed include, but are not limited to: polymeric materials, e.g., plastics, such as polytetrafluoroethene or polytetrafluoroethylene (PFTE), including expanded polytetrafluoroethylene (e-PFTE), polyethylene, polyester (Dacron™), nylon, polypropylene, polyethylene, high-density polyethylene (HDPE), polyurethane, polydimethylsiioxane (PDMS), one or more acrylic adhesive, silicone adhesive, epoxy adhesive, or any combination thereof, etc., metals and metal alloys, e.g., titanium, chromium, aluminum, stainless steel, etc., and the like. In various embodiments, the materials are transparent materials and as such, allow light within the visible spectrum to efficiently pass therethrough.

Furthermore, in various instances, a sample receiving cartridge, or a portion thereof is transparent to light, e.g., visible light. As such, a user can observe an optical property modification of a sample or an aspect thereof through the sample receiving cartridge. Also, in some versions, a sample receiving cartridge, or a portion thereof, is opaque and/or white.

According to some versions, the subject devices include a substrate. The substrate, in some instances, can be a circuit board, e.g., a printed circuit board, composed, for example, of a layer of Silicon and/or Copper and/or Gold and/or Aluminum contacts therein or thereon. Substrates can be printed circuit boards composed, for example, of a layer, e.g., a silicon layer, having thereon metallic contacts affixed thereto with one or more adhesive, e.g., epoxy. Substrates according to the subject embodiments can also have one or more surface, e.g., a first surface and a second surface opposite a first surface, having a roughness (Ra) of 5 µm or more, such as 10 µm or more, such as 20 µm or more, such as 50 µm or more. The substrates can also have a roughness (Ra) of 50 µm or less, such as 20 µm or less, such as 10 µm or less, such as 5 µm or less.

Substrates, in various instances, can include one or more optical property modifying substances and as such, be configured to have one of their optical properties, such as color, modified. As such, the methods include modifying one or more optical property of a substrate. In some aspects, substrates may include one or more enzyme, e.g., a colorimetric enzyme, which can provide a color change. As such, modifying an optical property can include changing the color and/or opacity of a substrate.

Where desired the substrates can include one or more heating elements. Heating elements are elements and/or one or more reactants that are configured to generate thermal energy and can be configured for heating one or more reaction chambers and contents thereof, e.g., a biological sample and/or an optical property modifying reagent and/or a nucleic acid amplification composition. Examples of such heating elements include thermoelectric heating elements, e.g., thermoelectric heating elements that include resistive conductors, e.g., thermistors, Peltier devices, or other elements that generate heat.

In some aspects, heating elements are or include one or more heat-generating reactants, e.g., liquid reactants, that cause an exothermic/exothermal reaction when exposed to one another or one or more of the compositions and/or reagents disclosed herein, e.g., water. Also, in some embodiments, the methods include adding to contents of a device as disclosed herein, e.g., contents including a biological sample, one or more heating reagents which, when mixed, cause an exothermal reaction. Such a reaction can, for example, heat a sample for lysis or produce a colorimetric change as described herein. Exothermal reactions can generate heat and/or gas. Exothermal reactions can include the hydration of a mixture composed of encapsulated and/or non-encapsulated oxides such as calcium oxide and/or magnesium oxide and dehydrated and/or hydrated zeolite, or any combinations thereof. Such a process can be coupled with control of pH of the mixture through compounds such as Citric acid, or combination exothermic mixes, such as Cao and Mg Fe. Modulation can include timed/controlled release from encapsulated reactants and can include particles with tailored size distribution and different burn characteristics. Phase change materials (PCM) can be used to control the heat stability of the reaction. PCMs include, for example, organics (paraffins, non paraffins and fatty acids) and inorganics (salt hydrates). The reagents applied in exothermal reactions or other gas-producing reagents may also be applied to produce gas inside one or more of the chambers, e.g., sealed chambers, of the devices disclosed herein and thereby increase pressure in the one or more container.

Heating elements can be configured to elevate the temperature of a reaction chamber and/or contents thereof, e.g., a biological sample, by 1° C. or more, 5° C. or more, 10° C. or more, 15° C. or more, 25° C. or more, 50° C. or more, or 100° C. or more. Such elements can be configured to increase the temperature of a reaction chamber and/or contents thereof from room temperature, e.g., 21° C., to 59° C., 60° C., 61° C., 62° C., 63° C., 64° C., 65° C., 66° C., or 67° C. and/or within a range from 50-75° C., such as 60-70° C., such as 60-66° C., in 10 minutes or less, such as in 5 minutes or less, such as in 3 minutes or less, such as in 2 minutes or less. For example, a heating element can be configured to increase the temperature of a reaction chamber and/or contents thereof from room temperature to 63° C.±1° C. in 3 minutes or less and/or can be configured to maintain such a temperature for 30 minutes or more. Heating elements can also be configured to maintain the temperature of a reaction chamber and/or contents thereof for a period of time such as 2 hours or more or 2 hours or less, such as 1 hour or less, such as 30 minutes or less, such as 15 minutes or less. Such a temperature can be maintained at, for example, 59° C., 60° C., 61° C., 62° C., 63° C., 64° C., 65° C., 66° C., or 67° C. and/or within a range from 50-75° C., such as 60-70° C., such as 60-66° C. Maintaining such a temperature can be performed by applying a thermistor as a heating sensing element and/or can be based on sensor feedback to a control unit. Heating elements can be configured to elevate the temperature of a reaction chamber and/or contents thereof, repeatedly, e.g., heat the contents a first time and then a second time. The subject heating elements also can heat the contents of a reaction chamber so that an optical property modification and/or nucleic acid amplification occurs. Furthermore, the subject heating elements also can heat contents to perform thermo-cycling for amplification reactions, such as PCR.

In some instances, the subject substrates can include one or more power sources. A power source can be operatively connected to one or more heating elements. By "power source," as used herein, is meant a device that supplies electric power to an electrical load. As such, in some aspects, power sources can include, for example, one or more battery, direct current (DC) power supply, alternating current (AC) power supply, linear regulated power supply, switched-mode power supply, programmable power supply, uninterruptible power supply, high-voltage power supply and/or a voltage multiplier. The amount of power, current and/or voltage capable of being provided by a power supply can, for example, be equivalent to that required to power the heating elements to generate heat according to the subject embodiments and/or other elements described herein, e.g., one or more controller, to provide their described functions. A power source can, in some aspects, be one or more battery, e.g., a portable and/or self-contained and/or replaceable battery, such as one or two AA batteries, an outlet, or another source of electrical power. In some aspects, a power source can include one or more electrical cords, e.g., cords configured to operatively connect a device to an outlet. Cords of power sources can be configured to removably connect to a device and/or an outlet.

Embodiments of power sources include power sources configured to turn on to provide electrical power to another component and/or turn off to stop providing electrical power to another component. Such power sources can be configured to be turned on and/or off, for example, by operation of a switch, button, timer or other component operatively connected to or included in the power source, such as a control unit.

As noted herein, power sources can, in certain aspects, be operatively connected to one or more components of the disclosed systems, e.g., a control unit. As such, embodiments of power sources include electrical connections from a power source to components of the disclosed systems. Such electrical connections can include one or more lengths of electrically conductive material, e.g., contacts, traces, and/or wires.

Where desired, substrates can include one or more control unit, e.g., a central processing unit (CPU) or a field-programmable gate array (FPGA). Such a unit can include a memory and/or a processor, e.g., a microprocessor, configured to generate one or more outputs, e.g., electrical signals, based on one or more sets of inputs, e.g., inputs from a user and/or a sensor, and/or a timer, and/or instructions stored in the memory. A device can also include a user interface for receiving an input and operatively coupled to the control unit.

In some versions, a control unit is configured to perform an optical property modification and/or colorimetric analysis of a biological sample in the one or more reaction chambers. As such, a control unit can be configured to determine, based on an input from one or more sensors, whether a change in an optical property, e.g., color, of one or more contents of a reaction chamber, has occurred. Based on the determination, the control unit can be configured to generate an output, such as an output to a user via a display, wherein the output reflects to the user whether a change has occurred.

Also, in some instances, a substrate can include one or more sensor, e.g., a plurality of sensors, configured to detect the presence and/or absence of a liquid, e.g., a biological sample, in one or more of the reaction chambers. In some instances the sensors are operatively connected to the control unit and send an input thereto based on a detected presence and/or absence of a sample. For example, a control unit can generate an output which activates a heating element of a device to heat contents, e.g., a biological sample, of one or more reaction chambers by transmitting thermal energy via an adhesive layer to the reaction chambers when an input from a sensor indicating the presence of a biological sample in a reaction chamber is received. In some versions, the one or more sensors can be configured to detect an optical property, e.g., a wavelength of light, e.g., color, and/or a change in an optical property, such as a wavelength of light emitted from contents of a reaction chamber, e.g., a biological sample.

In various aspects, substrates according to the subject embodiments include one or more light source configured to emit light. Such light sources can be operatively coupled to the one or more sensors and/or control units such that when a sensor detects a liquid, e.g., a biological sample, in the one or more reaction chambers, the light source emits light. Such light sources can also be operatively coupled to the one or more sensors and/or control units such that when an optical property modification occurs or does not occur in the one or more reaction chambers, the light source emits light. Light sources according to the subject embodiments can also include one or more light emitting diode (LED).

Also, in some versions, the devices include one or more display for displaying one or more output, e.g., reaction result, and/or status, to a user. In some versions, the devices also include an interface for receiving an input, wherein the interface is operatively coupled to the control unit.

The disclosed devices can also include a wireless signal transmitter and/or a wireless signal receiver. A wireless signal transmitter can be operatively coupled to the control unit and can be configured to transmit a signal, such as an audio signal, from the control unit to, for example, a wireless receiver operatively coupled to one or more other device, such as a second central processing unit and/or a sample analyzer, which can be a mobile device, such as a cellular telephone. The wireless signal receiver can be configured to receive a signal and transmit it for processing by the control unit.

In some versions, the subject devices include a housing. Such housings can include a first portion and a second portion operatively coupleable, e.g., mateable, e.g., snapedly coupleable, with the first portion to encapsulate the sample receiving cartridge, substrate and adhesive layer. In some versions, a second portion is substantially flat and a first portion is composed of five walls separated by edges and configured to contain, e.g., fully contain, one or more other components of a device, such as by retaining the components between at least two portions, e.g., opposite walls, thereof. In some versions a second portion makes up a bottom surface of the housing and the housing includes an inlet opening in a top surface of the housing opposite the bottom surface.

Housings of the subject devices can be composed of one or more layers of material, e.g., a polymeric material, as described herein, and can be shaped substantially as a rectangular box. The housings can include one or more inlet opening providing access, e.g., fluidic access, to an inlet of a sample receiving cartridge so that a biological sample can be loaded into the cartridge therethrough. In some versions, such an opening is on a top surface of a device and/or is in a first portion.

According to some embodiments, the subject devices and components thereof, e.g., housings, are hand-held devices or components. As used herein, the term "hand-held" refers to the characteristic ability of an aspect to be held (e.g., retained, or easily or comfortably held) in a hand, such as the hand of a mammal, such as the hand of a human, such as the hand of an adult male or female human of an average size and/or strength. As such, a hand-held aspect is an aspect that is sized and/or shaped to be retained (e.g., easily or comfortably retained) in the hand of a human. A hand-held aspect can also be an aspect that can be moved (e.g., easily moved, such as easily moved in a vertical and/or horizontal direction) by a human (e.g., one or two hands of a human).

In some embodiments, a housing has a volume and/or defines an exterior or interior volume, sufficient to contain any of the described components therein. A housing can have a volume, for example, of 1 $cm^3$ to 500 $cm^3$, such as from 10 $cm^3$ to 200 $cm^3$, such as from 50 $cm^3$ to 150 $cm^3$. In some instances, a housing can also have a volume of 1 $cm^3$ or more, such as 50 $cm^3$ or more, such as 100 $cm^3$ or more, such as 200 $cm^3$ or more, such as 300 $cm^3$ or more, such as 500 $cm^3$ or more. A housing can also have a volume of 500 $cm^3$ or less, such as 300 $cm^3$ or less, such as 200 $cm^3$ or less, such as 100 $cm^3$ or less, such as 50 $cm^3$ or less, such as 10 $cm^3$ or less.

In some aspects, the subject devices include one or more adhesive layer operatively connecting a sample receiving cartridge and a substrate. As is shown, for example, in FIG. 2, such a layer can also form a wall of each of the one or more reaction chambers. In forming a wall, an adhesive layer can seal and/or extend over an opening at an end of a reaction chamber. As such, an adhesive layer and/or a portion thereof, e.g., a sheet and/or an adhesive material can define an end of a reaction chamber and/or sealably contain one or more solid and/or fluid media, e.g., a biological sample and/or an optical property modifying reagent and/or a nucleic acid amplification composition, within the reaction chamber. In various embodiments, an adhesive layer can be operatively coupled to a sample receiving cartridge such that the adhesive layer fluidically seals one or more openings, e.g., an opening at an end, of one or more reaction chambers of the cartridge.

An adhesive layer according to the subject embodiments can be or include a sheet, e.g., a solid sheet, of one or more materials, e.g., two materials, having a thin and/or planar shape. An adhesive layer or other components of the subject devices can include a top surface and a bottom surface each defining a plane parallel with the other and separated by a thickness. In various embodiments, a sheet is or includes a uniform layer of a single material. An adhesive layer can also be composed of two or more, e.g., three, four, five, or more, etc. sheets laminated to one another. In some versions, the adhesive layers are acrylic adhesive laminates.

In various embodiments, an adhesive layer can be composed entirely of an adhesive material or can have an adhesive material, e.g., a coating and/or layer of adhesive material, on a first surface and/or one or other surfaces, e.g., a second surface opposite the first. Such an adhesive can be an acrylic adhesive. Accordingly, an adhesive layer can include one or more sheets, e.g., laminated sheets, and have an adhesive material on a top surface and/or a bottom surface thereof. One layer of adhesive material can operatively connect the adhesive layer with a substrate and/or another layer of adhesive material can operatively connect the adhesive layer and a sample receiving cartridge.

A sheet can, in some aspects, have a length, a width and a height, also referred to as a thickness. A sheet can be shaped as a rectangular box with the width and length being substantially greater than the thickness. A thickness of an adhesive layer and/or a sheet, e.g., a thickness between a first surface and a second surface opposite the first surface, can be 5 mm or less, 3 mm or less, 1 mm or less, 0.5 mm or less, 0.1 mm or less, or 50 microns or less. A thickness of an adhesive layer and/or a sheet thereof can also range for example, from 5 mm to 50 microns, such as 3 mm to 0.1 mm, such as 1 mm to 0.1 mm, inclusive. Also, a length and/or width of an adhesive layer and/or a sheet can also range from 1 mm to 2 m, such as from 1 cm to 1 m, such as from 1 cm to 10 cm, such as from 1 cm to 5 cm.

Adhesive layers can be and/or have an area defining any suitable size or shape including a: circle, semi-circle, oval, rectangle, square, triangle, polygon, quadrilateral, or combination thereof. For example, in embodiments where the adhesive layer is a rectangle, the length of the adhesive layer is greater than the width. An adhesive layer can include one or more sheets of solid, uniform, integrated material, and in some versions, does not include any openings therethrough.

An adhesive layer and/or a sheet thereof can have three edges, four edges, or more than four edges which define the area of the adhesive layer. In various embodiments, the edges meet at corners, e.g., three, four, five, or ten or more corners. In some versions, a first edge of an adhesive layer is opposite a second edge of an adhesive layer and adjacent to a third and/or fourth edge of an adhesive layer. In such an embodiment, the third edge can be opposite a fourth edge and the fourth edge can be adjacent to the first and/or second edge.

According to the subject embodiments, adhesive layers can each be composed of a variety of materials and can be composed of the same or different materials. The sample receiving modules and/or caps or portions thereof can be composed of polymeric materials, e.g., materials having one or more polymers including, for example, plastic and/or rubber. Such materials can have characteristics of flexibility and/or high strength (e.g., resistant to wear) and/or high fatigue resistance (e.g., able to retain its physical properties for long periods of time regardless of the amount of use or environment). Materials of interest of which adhesive layers or portions thereof described herein can be composed include, but are not limited to: polymeric materials, e.g., plastics, such as polytetrafluoroethene or polytetrafluoroethylene (PFTE), including expanded polytetrafluoroethylene (e-PFTE), polyester (Dacron™), nylon, polypropylene, polyethylene, high-density polyethylene (HDPE), polyurethane, one or more acrylic adhesive, silicone adhesive, epoxy adhesive, or any combination thereof. As described, each of such materials can include coatings or layers of adhesive materials, e.g., acrylic adhesive materials, on one or more surface thereof.

Furthermore, in various instances, an adhesive layer, or a portion thereof, such as a first and/or second laminated layer, does not include an acid. Also, in some versions, an adhesive layer, or a portion thereof, e.g., such as a first and/or second laminated layer, is opaque and/or white. Where an adhesive layer or a portion thereof is white, the white layer provides a uniform background of visual inspection of one or more reaction chambers. In some versions, a layer, e.g., a first layer and/or second layer and/or an adhesive layer, is opaque and/or a color complementary to a reaction start color, e.g., red, orange, yellow, green, blue, indigo, violet, black, gold, silver, brown, or any combination thereof. A reaction start color is the color of the reaction product and/or the optical property modifying reagent before a reaction occurs to sufficiently modifies an optical property of the optical property modifying reagent to allow detection of the modified optical property. The color complementary to a reaction start color may provide sufficient color contrast, e.g., increased color contrast as opposed to a single color, of the reaction chambers such that, for example, detection of the modified optical property may be made by an unassisted human eye.

In various instances, an adhesive layer, or a portion thereof, is transparent to light, e.g., visible light. In other versions, an adhesive layer, or a portion thereof, is reflective, e.g., entirely or substantially reflective to light, e.g., visible light. Also, as noted herein, an adhesive layer can include a first layer laminated with a second layer. In such embodiments, for example, a first layer does not include an acid and/or a second layer is opaque and/or white.

Additionally, in various instances, an adhesive layer, or a portion thereof such as a sheet, has a thermal conductivity ranging from 0.1 W/m-K to 10 W/m-K, such as 0.1 W/m-K to 5 W/m-K, such as 1 W/m-K to 5 W/m-K.

According to some versions, an adhesive layer is a patterned adhesive layer. In such embodiments, the adhesive layer can be or have a portion that is porous and/or includes one or more opening extending from a first surface of an adhesive layer to a second surface of the adhesive layer opposite the first surface such that one or more contents, e.g., liquids, of a reaction chamber can pass therethrough. As such, in some aspects, one or more contents, e.g., liquids, of a reaction chamber can contact a substrate and/or one or more components thereof, e.g., a sensor and/or a heating element, directly while an assay is performed.

As described herein, the subject devices and methods can be used to detect the presence and/or absence of one or more nucleic acids in one or more reaction chambers. The subject devices and methods can also be applied, for example to detect the presence and/or absence of one or more other biomarkers, such as proteins, in the one or more reaction chambers.

In various embodiments, optical property modifying devices contain one or more, e.g., three, assay controls: a sample adequacy control, a positive control, e.g., an internal positive control, and/or a negative control. The sample adequacy control detects, for example, abundant human nucleic acid markers such as housekeeping genes, RNA, and/or human β-actin deoxyribonucleic acid (DNA) to ensure a sufficient swab sample was collected. The positive control amplifies a synthetic oligonucleotide that will be co-packaged and/or co-lyophilized in the reaction well. Such a synthetic oligonucleotide can be included, for example, in a modifying reagent, an optical property modifying reagent and/or an amplification composition. Such a control ensures that the device operates under conditions that allow amplification of genetic markers of interest. The negative control also amplifies the positive control but without the co-lyophilized synthetic oligonucleotide. Such a control ensures the absence of any contaminating self-amplifying amplicon.

In addition, the optical property modifying devices or portions thereof, e.g., housings, can include calibrators for an image data analysis algorithm as performed, for example, by a control unit of a sample analyzer. For example a quick response (QR) code, can be a resolution calibration target. Also, a white housing, and specifically a region proximate reaction chambers, can be applied by the sample analyzer for white balance calibration and illumination uniformity calibration. Additionally, housings can include printed color targets for calibrating color change measurements.

Optical property modifying devices can also include one or more code, e.g., a quick response (QR) code, on an exterior of a housing thereof. Such a code can include an identification of assay type, expiration date for the device, serial number, or any combination thereof. A sample analyzer can be configured to read and/or recognize such a code so that a proper identification of the device can be made and the device used accordingly.

As noted above, in various embodiments, the devices include a selective venting element. Selective venting elements can be porous and as such, have a plurality of pores extending therethrough. Selective venting elements according to the subject embodiments can also have a passively tunable porosity. The phrase "passively tunable porosity," as used herein, refers to the ability of having a first conformation in which one or more gasses, e.g., air, can pass therethrough, e.g., through pores, and a second conformation in which fluids including the one or more gasses and liquids, such as liquids including a biological sample, are prevented from passing therethrough, e.g., through the pores, and proceeding automatically from the first to the second conformation upon contact with a liquid. In the second conformation, the selective venting elements prevent evaporation of the liquids therethrough, e.g., through the pores. Also, in the second conformation, the selective venting elements can fluidically seal a reaction chamber at an end thereof by covering an opening thereof and prevent passage of fluid, including evaporation, therethrough. The selective venting elements can be configured to proceed from the first conformation to the second conformation passively, e.g., automatically without user interaction, upon contacting the one or more liquids, such as liquids including a biological sample, with the selective venting elements or a portion thereof, e.g., a surface, such as a surface forming a wall of a reaction chamber. As such, in some versions, selective venting elements can be self-sealing to liquids and gasses when contacted by a liquid. Additionally, in some versions, selective venting elements may cover and/or seal one or more inlet and/or sample receiving opening of a device and may thereby regulate, e.g., allow and/or prevent liquid and/or gas flow therethrough in the same manner as through the one or more venting openings.

Also, each reaction chamber can include a sample receiving opening for receiving a biological sample from the sample inlet and/or a conduit. A sample receiving opening can be operatively, e.g., fluidically, connected to a sample inlet. In some versions, each reaction chamber includes one or more, e.g., two, additional openings, such as a "vented" and "supplementary," or "first" and "second" opening. Accordingly, in some versions, a sample receiving opening is a third opening and is adjacent to the first and/or second openings. Reaction chambers can also include a fourth opening operatively coupling the chamber to one or more other chambers and/or the inlet via one or more conduits.

Also, one or more portions or materials of selective venting elements can have a passively tunable porosity. For example, in some versions, selective venting elements can be composed of a hydrogel having a passively tunable porosity. Such a hydrogel can be capable of swelling and reducing the porosity of the porous polymer matrix upon contact with a liquid, e.g., an aqueous liquid.

Furthermore selective venting elements can be composed of a variety of materials including one or more polymer matrix, such as a porous polymer matrix, such as polyethylene. Selective venting elements can also be composed of a hydrogel such as carboxymethyl cellulose. Other materials of which selective venting elements or portions thereof, such as coatings, can also be composed include saccharides, proteins, deliquescent materials, nylon, ABS, polycarbonate, and Poly(methyl methacrylate), and other hygroscopinc materials, or any combinations thereof. Selective venting elements may also be or include one or more coatings. Selective venting elements can be shaped as a comb. As such, the elements can include a body and one or more protrusions, e.g., cylindrical protrusions, extending from the body to cover each of one or more openings, e.g., first or second openings, of reaction chambers. A selective venting element of a device can have a number of protrusions equal to the number of reaction chambers in the device. Furthermore, a selective venting element can be operatively coupled to a device housing and/or a microfluidic cartridge and can be disposed between such elements within a device.

Methods of the Invention

The present disclosure includes methods of modifying an optical property in a biological sample assay. Such a modification can be performed on a biological sample, or an aspect associated therewith, such as a reaction mixture or a reaction product. Where desired, a modification of an optical property can be performed with a biological sample assay optical property modifying device as such devices are described herein.

Modifying an optical property refers to changing one or more optically-recognizable characteristics of an aspect, e.g., a sample, such as a characteristic resulting from wavelength and/or frequency of radiation, e.g., light, emitted from an aspect, such as color, fluorescence, phosphorescence, etc. For example, in some versions, the optical property is color and modifying the optical property includes changing the color. In some aspects, such an optical property modification, e.g., color change, is detectable by an un-assisted human eye under, for example ambient light, and the subject methods include making such detection with an un-assisted human eye. Modifying an optical property can also include changing the transmittance and/or opacity of a substance and can include causing the substance to change substantially from transparent to opaque or from opaque to transparent. As such, the methods can include detecting such a change with an un-assisted human eye.

In some aspects, the subject methods include exposing a reagent or substance as disclosed herein and/or a device or portion thereof, e.g., a sample receiving cartridge, to external, e.g., ambient, light to thereby measure the change in optical property. Such external light can include a camera flash or fluorescent excitation light. Exposure to external light can provide a change in conditions such that the optical property can be measured.

According to some versions of the subject methods, the methods include transmitting a biological sample into one or more reaction chambers of a sample receiving cartridge of an optical property modifying device. Transmitting a sample can include moving, e.g., flowing, a sample, to a particular location, such as one or more reaction chambers. Transmitting can include flowing the sample through a sample inlet and/or one or more conduits operatively connecting each of the one or more reaction chambers. Such flowing can include biasing, e.g., pumping, the sample to move through the inlet and/or conduits. The flowing can also include flowing the sample into an opening in the sample inlet through a receptacle opening in the housing of a device.

In various embodiments, transmitting a biological sample into one or more reaction chambers includes operatively coupling a biological sample assay optical property modifying device with a sample preparation device and flowing a prepared biological sample from the sample preparation device into the biological sample assay optical property modifying device. Operatively coupling such devices can include coupling reciprocating connectors, e.g., fluidic connectors, e.g., luer connectors, of each device.

As noted above, one or more one or more reaction chambers of a device can include one or more optical property modifying reagent. As such, transmitting a biological sample into one or more reaction chambers can include mixing a biological sample with the one or more optical property modifying reagent and thereby generating a reaction mixture including the biological sample and optical property modifying reagent. A reaction mixture is a mixture which can be employed in one or more reactions as designated herein. A reaction mixture can also include, for example, an amount of buffer, water, and/or other compositions such as a biological sample, e.g., a prepared biological sample, an amplification composition, e.g., a nucleic acid amplification composition, and/or one or more optical property modifying reagent, or any combination thereof.

The subject embodiments also include heating a reaction mixture with a heating element of a device. In some versions such heating includes transferring thermal energy to one or more reaction chambers via an adhesive layer. Heating the reaction mixture in turn can generate a reaction product, e.g., a reaction product including a plurality of protons. A reaction product can include, for example, one or more compositions, e.g., an aspect of a biological sample, e.g., protons, which, when reacted with an optical property modifying reagent, result in a modification of one or more optical property.

Where desired, a heating element is operatively coupled to a substrate, e.g., a circuit board, such as a printed circuit board, of a device. A substrate can also include and/or be operatively coupled to one or more sensors and/or a control unit and/or a power source, and/or one or more light source. As such, in some versions, transmitting a biological sample into one or more reaction chambers includes detecting a sample, e.g., a liquid, in one or more reaction chambers with one or more sensors. The sensors can be, for example, electrochemical sensors. The sensors can be configured to send and/or receive electrical energy to and/or from one or more reaction chambers via, in some versions, an adhesive layer and/or one or more electrical contacts. Such sensors can be configured to detect the presence and/or absence of liquid in one or more reaction chambers. Also, in some variations wherein a substrate is operatively coupled to a light source, transmitting a biological sample into one or more reaction chambers can include activating the light source to emit light and/or deactivating the light source to stop emitting light. In some versions of the subject devices, the sensors, control unit and/or heating element are operatively connected such that when liquid enters a reaction chamber, the sensor senses the liquid and the heating element begins heating the reaction chamber automatically, such as without a particular user action required.

In embodiments wherein a substrate includes a control unit, modifying an optical property of the biological sample can include performing an optical property, e.g., colorimetric, analysis of a sample in the one or more reaction chambers with the control unit. Such an analysis can be performed on a reaction product after reacting it with the optical property modifying reagent. Performing an optical property, e.g., colorimetric, analysis can include determining, based on an input, e.g., an input from one or more sensors, whether a change in an optical property, e.g., color, of one or more contents of a reaction chamber, has occurred. Based on the determination, performing the analysis can include generating an output, such as an output to a user via a display, wherein the output reflects to the user whether a modification has occurred. Performing an optical property, e.g., colorimetric, analysis can also be performed by a user without employing a control unit, such as by using an analyzing device or by making a determination based on a visual inspection. Furthermore, performing an optical property, e.g., colorimetric, analysis can also include obtaining image data, e.g., photo and/or video, of an optical property modification or lack thereof with, for example, a camera, such as a camera on a mobile phone, and evaluating the data visually or with an analyzing device, such as a mobile phone.

In some versions, the subject methods include transferring electrical energy from one or more elements of a substrate, e.g., a control unit and/or a sensor, to one or more reaction chambers via an adhesive layer. The methods can also include transferring electrical energy from one or more reaction chambers to one or more elements of a substrate, e.g., a control unit and/or a sensor, via an adhesive layer. In some aspects, performing an optical property modification analysis requires such electrical energy to be transmitted.

In some versions of the methods, the sample receiving cartridge is transparent, and performing an optical property, e.g., colorimetric, analysis includes detecting, visualizing, one or more characteristics of light, e.g., color or opacity, transmitted through the sample receiving cartridge. In some aspects of the methods, an optical property modifying device also includes an adhesive layer, an opaque and/or white adhesive layer, operatively connected to the sample receiving cartridge. In such aspects, the methods can include performing an optical property analysis, such as by visually inspecting the chambers to detect a modified optical property, of the reaction product after reacting it with an optical property modifying reagent.

Biological sample assay optical property modifying devices can also be manufactured according to the subject methods by operatively coupling a sample receiving cartridge and/or a substrate with the adhesive layer. Such coupling can be performed by placing an adhesive layer against a sample receiving cartridge and/or a substrate and attaching, such as by adhesively binding and/or melting the components to one another. Specifically, in some embodiments, the methods include contacting an adhesive layer directly with a substrate, e.g., a printed circuit board, and binding, e.g., adhesively binding, or laminating the two together. In some aspects, an adhesive layer has a first side and a second side opposite the first side. As such, manufacturing a device by operatively coupling a sample receiving cartridge and substrate can include adhesively attaching the sample receiving cartridge to the first side and the substrate to the second side. Such manufacturing can be performed manually or automatically, such as with an electronic manufacturing device, such as a manufacturing device which can be programmed to perform one or more manufacturing steps.

In some versions, the reaction chambers each include an amplification composition, e.g., a nucleic acid amplification composition. As noted above, one or more one or more reaction chambers of a device can each include an amplification composition, e.g., a nucleic acid amplification composition. As such, transmitting a biological sample into one or more reaction chambers can include mixing a biological sample with the one or more amplification composition. Such mixing can include causing a chemical reaction between the two.

In some instances, heating a reaction mixture with a heating element includes accelerating a nucleic acid amplification reaction between, for example, nucleic acids of a biological sample and one or more aspects of an amplification composition, e.g., a nucleic acid amplification composition. As such, in various aspects, the reaction generates one or more amplified nucleic acid. Such a reaction can also generate a reaction product. Such a reaction product can be or include a plurality of protons and/or one or more amplified nucleic acid.

The subject methods also can include reacting the reaction product, or an aspect thereof, such as one or more protons and/or one or more amplified nucleic acid, with an optical property modifying reagent. Such reacting can be performed, for example, by placing the reaction product, or an aspect thereof, such as one or more protons and/or one or more amplified nucleic acid, in contact with an optical property modifying reagent, such as by mixing them in one or more container, e.g., one or more reaction chambers. Reacting the reaction product, or an aspect thereof, with an optical property modifying reagent can include chemically modifying the reaction product and/or the optical property modifying reagent, such as by bonding the one or more protons to the optical property modifying reagent, so that one or the other displays one or more different optical property, such as a color and/or opacity.

Reacting the reaction product, or an aspect thereof, such as one or more protons and/or one or more amplified nucleic acid, with an optical property modifying reagent, in various embodiments, sufficiently modifies an optical property, e.g., color and/or opacity, of the optical property modifying reagent to allow detection of the modified optical property by an un-assisted human eye. The term "human," as used herein, can include human users or subjects of both genders and at any stage of development, e.g., fetal, neonates, infant, juvenile, adolescent, adult, where in certain embodiments the human subject or user is a juvenile, adolescent or adult. Also, an un-assisted human eye refers to a human eye that is not enhanced by one or more devices which enhance or modify visual ability. Such devices might include a camera, optical magnifier, microscope, or optimized, e.g., filtered, e.g., polarized, glasses or contacts, etc.

One embodiment of the subject methods can be illustrated in association with the device 100 as shown in FIGS. 1 and 2. Accordingly, in some aspects, the methods include transmitting a biological sample into one or more reaction chambers 102 of a sample receiving cartridge 101 of a biological sample assay optical property modifying device 100 and thereby generating a reaction mixture. Such transmission can be performed via sample inlet 110 and/or conduits 202.

The methods can also include heating the reaction mixture with a heating element 104 of the device 100 and thereby generating a reaction product. In various instances, the methods also include reacting the reaction product with the optical property modifying reagent 201, wherein the reacting sufficiently modifies an optical property of the optical property modifying reagent to allow detection of the modified optical property by an un-assisted human eye while the reaction product is with the one or more reaction chambers 102 of the sample receiving cartridge 101. Detection of the modified optical property with an un-assisted human eye can be performed, for example, through a sample receiving cartridge 101, which can be transparent.

Also, in some versions, the methods include containing, e.g., stopping substantial movement, such as a flow of, a sample in the one or more reaction chambers 102 with a selective venting element 107 and/or an adhesive layer 106. In such embodiments, transmitting a biological sample into one or more reaction chambers 102 includes flowing a gas, e.g., air, through the selective venting element 107 before contacting a liquid, e.g., a biological sample, with the selective venting element 107 and thereby making it impermeable to liquid and gas flow.

In various instances, a device 100 includes a housing including a first portion 108 having a receptacle 111, and a second portion 109 mateable with the first portion. As such, transmitting the biological sample into the one or more reaction chambers 102 can include flowing a sample through the receptacle 111.

Furthermore, in some embodiments, the subject methods include collecting a biological sample, such as collecting a sample with a sample collector. Such a sample can include, for example, human saliva, urine, human mucus, blood, or a solid tissue such as buccal tissue. Such a sample can also include bacteria or spores. Collecting can include contacting, e.g., rubbing and/or scraping, the sample collector against one or more surfaces of a subject and/or surfaces of a biological sample of a subject, such as a liquid, e.g., saliva and/or blood, sample extracted from the subject. As such, in some versions, collecting includes extracting one or more biological samples from the subject. In some versions, collecting the biological sample can include instructing a subject to produce a biological sample, such as by spitting onto and/or into a sample collector. Collecting the biological sample can also include retaining a biological sample or a portion thereof, e.g., one or more cells, on the sample collector while, for example transferring the sample collector to an assay device. In some instances, a sample collector is a swab and collecting the biological sample includes swabbing the inside of a subject's mouth and/or nose to obtain the biological sample on the collector. In some versions, sample collectors are nasopharyngeal, mid turbinate and/or nasal swabs. After a biological sample is collected, the methods, in some versions, include processing the biological sample so that it is a prepared biological sample as described herein.

In addition, in some versions of the methods, a device is manufactured by encapsulating within a housing a selective venting element, sample receiving cartridge, adhesive layer, and/or substrate, or any combination thereof, by contacting them together in a single concerted step. In some variations, the methods do not include manufacturing a device for example, by performing a first step of patterning a substrate layer, such as a glass, silicon and/or polymer layer, and/or binding a patterned, e.g., binding it chemically and/or physically, to a non-patterned layer, e.g., a sealing layer, and a second subsequent step of integrating the bound and/or sealed layer into a housing or cassette that provides additional functionality to employ the fluidic device. Also, in various embodiments, the methods of manufacturing the subject devices include substantially preserving the functionality, e.g., chemical functionality, of reaction chamber contents, such as optical property modifying reagents and/or amplification compositions, while the contents are contained in the reaction chambers during manufacturing. This is achieved as the manufacturing process does not expose reagents to extreme temperature or chemical environments. Also, in some versions of the methods, the methods include manufacturing a device by operatively coupling an adhesive layer and a substrate while reaction chamber contents, such as optical property modifying reagents and/or amplification compositions, are retained within the reaction chambers. In some versions, operatively coupling an adhesive layer and a substrate does not include heating the adhesive layer, substrate, or environment surrounding either.

The amplification reaction provided herein amplifies nucleotides from a nucleic acid template. In some embodiments, the amplification reaction is an isothermal amplification reaction, such as a strand displacement reaction. In a further embodiment, a strand displacement reaction is provided by a polymerase with strand displacement activity under reaction conditions such that strand displacement is possible. Examples of strand displacement reactions include strand displacement amplification (SDA), multiple displacement amplification (MDA), rolling circle amplification (RCA) or loop mediated isothermal amplification (LAMP). In other embodiments, the amplification reaction includes other non-isothermal amplification reactions such as polymerase chain reaction (PCR).

In certain embodiments, the amplification reaction performed is LAMP. In a LAMP reaction, a double- or single-stranded DNA template in dynamic equilibrium at an elevated temperature is amplified using two or three pairs of primers. The primers are designed based on the DNA template, using primer design software such as LAMP Designer (Premier Biosoft, Palo Alto, CA). In the first step of the LAMP reaction, the F2 region of the FIP (Forward Inner Primer) anneals to the single stranded DNA at the respective complementary (F2c) position. Next, a polymerase with strand displacement activity incorporates dNTPs along the template from the 3' end of F2. The incorporation of nucleotides releases protons, reducing the pH of the reaction mix. Then, the F3 forward primer anneals to the F3c region upstream of the F2 region and on the template. The F3 forward primer begins amplifying the template strand, which releases further protons and displaces the FIP-incorporated strand that was synthesized previously. This single strand contains an F1 sequence (within the target sequence) along with its complementary F1c sequence (within the FIP). This forms a stem-loop as F1c anneals to F1 at the 5' end. At the same time, the BIP (Backward Inner Primer) anneals to the other end of the strand and nucleotides extend from B2, releasing more protons. The backward primer B3 then binds to the B3c region, downstream of the B2 region, displaces the BIP-amplified strands and promotes extension to create the double strand. This displaced strand now contains a B1 sequence (within the target sequence) along with its complementary B1c sequence (within the BIP), forming another stem loop in the 3' end. The structure now has two stem-loop structures at each end from which continuous displacement and extension occur to amplify the template. The LAMP reaction can be amplified by adding further Forward and Backward Loop primers to produce more amplicons with stem loop structures.

The LAMP procedure can take place at a fixed temperature, minimizing the need for any expensive thermocycling equipment. Typically, isothermal methods require a set temperature, which is determined by the selected reagents. For example, enzymes function best between 60-65° C. in LAMP methods.

Colorimetric detection of the nucleic acid amplification reaction product can be performed in real-time throughout the amplification reaction, or after the performance of the amplification reaction. Detection of the colorimetric change of the reaction mix can be associated with a digital indication of a presence or absence of the amplification reaction product. In other words, a visual observation of the color change of the reaction mix can provide information regarding whether the amplification reaction product is present or absent. In certain embodiments, detection of a colorimetric change of the reaction mix indicates that the exponential or plateau phase of the amplification reaction has been obtained.

In some embodiments, detection of the amplification reaction product is accelerated relative to an amplification reaction that uses a reaction mix without a halochromic agent. In further embodiments, the colorimetric change of the reaction mix is detected in less than 60 minutes from a starting time of the amplification reaction. Accelerated detection of the amplification reaction product is obtained because the halochromic agent (a weak acid or base) in the reaction mix absorbs protons generated during the amplification reaction, and recombination of the free protons acts to accelerate the detection of the amplification reaction. The reaction can be designed so that minimal amplification is required to generate a pH transition sufficient for the halochromic agent to change color. Conventional amplification techniques that use fluorescent intercalating dyes, molecular beacons, hybridization probes, dye-based detection, UV-Vis, or other detection methods require a certain threshold amount of amplification to occur before an amplification signal is detectable. However, the methods of the present invention require a relatively smaller threshold amount of amplification before a color change of the halochromic agent is detectable, and therefore the detection of an amplification reaction product is accelerated relative to conventional amplification methods.

In some embodiments, the amplification reaction product is detected visually by observation of a color change of the reaction mix. In a further embodiment, the human eye is used for the visual detection. In another embodiment, a camera, a computer, or some other optical device is used for the visual detection or for imaging the reaction mix. Imaging programs include PHOTOSHOP® (ADOBE®, San Jose CA), ImageJ (National Institutes of Health, Bethesda MD), and MATLAB® (MathWorks, Natick MA). In another embodiment, the amplification reaction product is detected by measuring fluorescence of the reaction mix, using fluorescence spectroscopy methods. In another embodiment, the amplification reaction product is detected by measuring absorbance of the reaction mix, using absorption spectroscopy methods. In a further embodiment, the endpoint or overall change in absorbance or fluorescence of the reaction mix is measured at a given wavelength or set of wavelengths.

FIG. 17 provides nucleic acid amplification reaction times across six different reaction chambers in an optical property modifying device according to embodiments of the subject disclosure. Columns represent reaction chamber positions and rows represent different devices. An integrated heating and fluidic cartridge provides uniform heating, allowing uniform multiplexed reaction conditions. As such, in this embodiment, the optical property modifying device includes an integrated heating element. The assay associated with the data presented in FIG. 17 is a LAMP control assay similar to the lambda DNA assay described herein.

In addition, FIG. 18 provides color changes, as measured using the CIE94 Delta-E scale, resulting from nucleic acid amplification reactions across six different reaction chambers in an optical property modifying device according to embodiments of the subject disclosure. As provided in FIG. 18, columns represent reaction chamber positions and rows represent different devices. An integrated heating and fluidic cartridge provides uniform heating, allowing uniform multiplexed reaction conditions. As such, in this embodiment, the optical property modifying device includes an integrated heating element. The applied device also includes an adhesive layer. The adhesive layer interposed between the fluidic channels and heater substrate provides thermal conduction as well as a uniform white background for reading color. The assay associated with the data presented in FIG. 18 is a LAMP control assay similar to the lambda DNA assay described herein. This device architecture represents a low-cost solution for visually reading multiplexed nucleic acid amplification assays.

Figure 19:
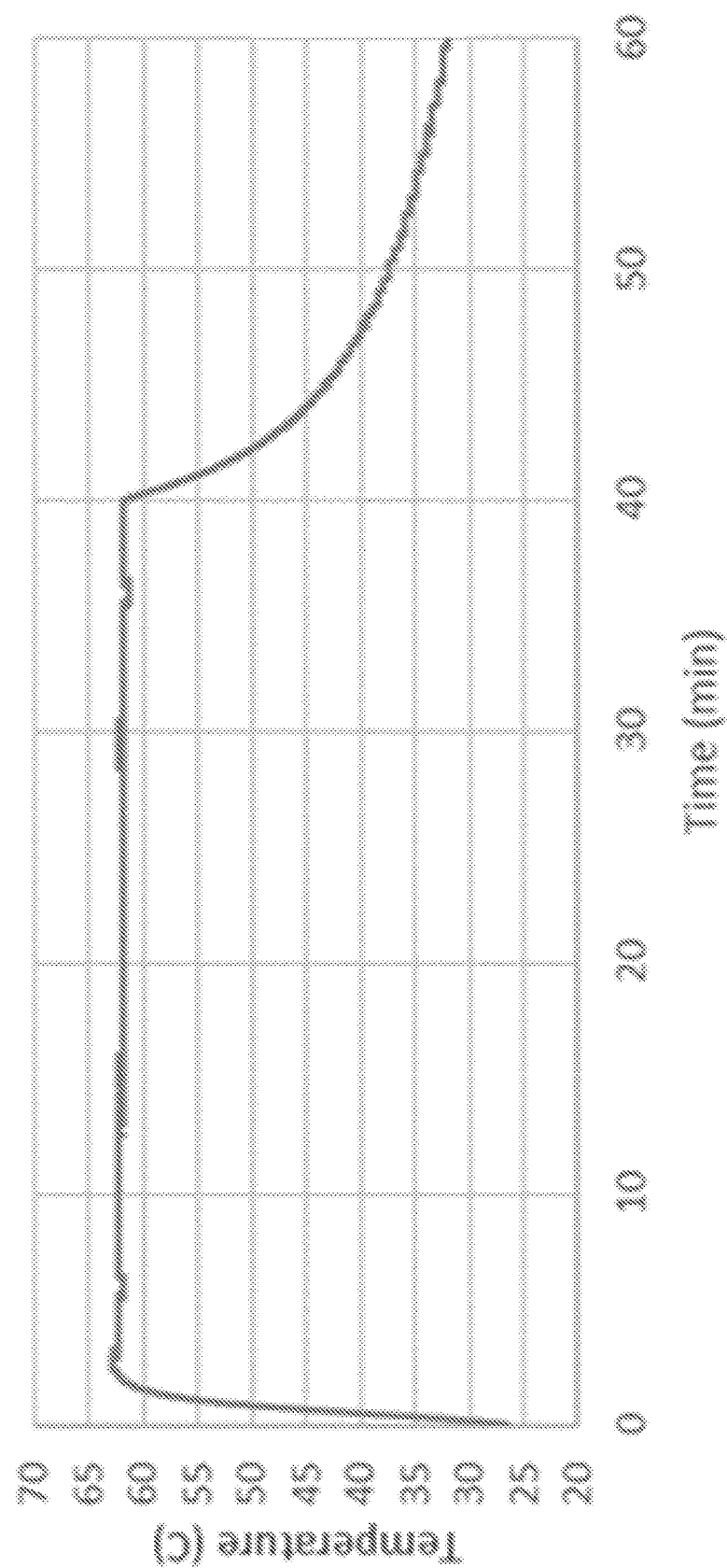
FIG. 19 provides a temperature profile of a reaction chamber, e.g., fluidic reservoir, operatively coupled to a heating element in the described manner according to embodiments of the subject disclosure.
Figure 20:
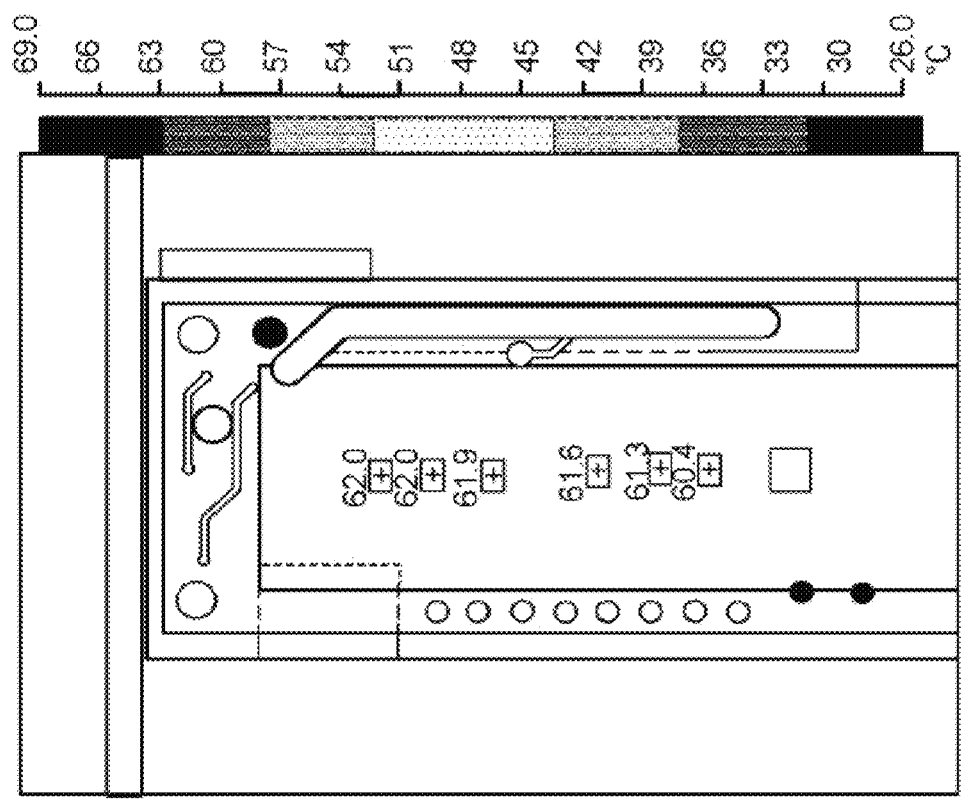
FIG. 20 provides temperature uniformity across six heating locations on a heating element, e.g., an electronic heater board, operatively coupled with a multiplexed nucleic acid amplification assay according to embodiments of the subject disclosure.

Furthermore, FIG. 19 provides a temperature profile of a reaction chamber, e.g., fluidic reservoir, operatively coupled and/or adjacent to a heating element, e.g., an electronic heater, in the described manner. In addition, FIG. 20 provides a depiction of temperature uniformity across six heating locations on a heating element, e.g., an electronic heater board, for operatively coupling with a multiplexed nucleic acid amplification assay. In such an embodiment, the assay includes an optical property modifying device including reaction chambers according to embodiments of the subject disclosure.

Compositions of the Invention

The compositions provided below can be applied in any embodiments of the devices and methods described herein for accelerated and efficient colorimetric detection of nucleic acid amplification reaction products. In an embodiment, a colorimetric assay is used to visually detect the presence of an amplified nucleic acid product, which eliminates the need for expensive and sophisticated instrumentation.

In some embodiments, the colorimetric detection of amplification products is achieved by amplifying a target nucleic acid template molecule to obtain the amplification reaction product. The amplification reaction includes a reaction mix. In an embodiment, the reaction mix includes a nucleic acid template molecule, one or more enzymes for catalyzing the amplification reaction, and one or more halochromic agents for colorimetric detection. In a further embodiment, the reaction mix also includes a buffer having a buffering capacity equivalent to Tris buffer at a concentration between 1 mM-19 mM in a solution having a starting pH of 8.0. In further embodiments, the reaction mix also includes a plurality of nucleic acid primers, deoxynucleotide triphosphates (dNTPs), suitable salts for the enzyme, and other non-buffered chemicals that enable nucleic acid amplification.

During the amplification reaction, one proton is released for each dNTP that is incorporated into a nucleic acid template molecule. Thus, the pH of the reaction mix decreases throughout the amplification reaction. In an embodiment, if the target nucleic acid is present, the amplification reaction changes the starting pH of the reaction mix to cause a detectable colorimetric change of the halochromic agent, thereby indicating the presence of the target nucleic acid, and if the target nucleic acid is not present, the amplification reaction does not generate a sufficient number of protons to change the starting pH of the reaction mix sufficient to cause a detectable colorimetric change of the halochromic agent, thereby indicating that the amplification reaction product has not been produced. In an embodiment, the halochromic agent (or pH indicator) in the reaction mix has a transition pH range for a colorimetric change of the halochromic agent that is narrower than an expected pH change between (1) a starting pH of the reaction mix before the amplification reaction is performed, and (2) an ending pH of the reaction mix after the amplification reaction has been performed.

In an embodiment, the halochromic agent is a colorimetric agent or a fluorescent agent. Suitable halochromic agents include phenol red, bromocresol purple, bromothymol blue, neutral red, naphtholphthalein, cresol red, cresolphthalein, phenolphthalein, methyl red, and thymolphthalein, among others. A wide range of concentrations of these halochromic agents can be used in the reaction mix. Different halochromic agents have different transition pH ranges. In some embodiments, the halochromic agent has a transition pH range between pH 5-10, between pH 6-9, or between pH 6.5-8.8. In another embodiment, the halochromic agent is at a concentration between 25-100 µM in the reaction mix. In another embodiment, the halochromic agent is at a concentration between 50-260 µM. In some embodiments, a combination of two or more halochromic agents is used in the reaction mix, which increases the normalized color contrast change of the reaction mix by being of complementary colors at the beginning and similar colors at the end of the amplification reaction. In a further embodiment, the combination of halochromic agents comprises phenol red and bromothymol blue. In a further embodiment, the combination of halochromic agents comprises cresol red and bromothymol blue.

In one example, Phenol red is a halochromic agent that has a transition pH range from around 6.4-8.0. At the upper limit of the transition pH range, phenol red is red, and at the lower limit of the transition pH range, phenol red is yellow. A reaction mix containing phenol red will change color from red to yellow throughout the amplification reaction, as long as the starting pH of the reaction mix is around or above 8.0, and the ending pH of the reaction mix is within the transition pH range or around or below 6.4.

In some embodiments, the starting pH of the reaction mix is set by adding an acid or a base to the reaction mix until the desired starting pH is reached. The ending pH of the reaction mix is determined by performing a sample amplification reaction and measuring the ending pH (for example, with a micro-pH electrode). In an embodiment, the halochromic agent for an amplification reaction is selected so that the transition pH range lies in between the starting pH and ending pH. In a further embodiment, the halochromic agent is selected so that the transition pH range is nearer to the starting pH than the ending pH. The halochromic agent can also be selected based on the particular enzyme used for catalyzing the amplification reaction. Near the ending pH, the enzyme in the reaction mix terminates polymerization of the amplification reaction as the pH decreases to unfavorable H+ concentrations. In an embodiment, additional hydronium ions or hydronium ion equivalents are added to the reaction mix via the sample. For example, between $4.8 \times 10^{-9}$ and $4.8 \times 10^{-18}$ additional hydronium ion equivalents per 10 µl reaction mix can be tolerated for the amplification reaction to proceed. In a further embodiment, between $4.8 \times 10^{-10}$ and $4.8 \times 10^{-18}$, $4.8 \times 10^{-12}$ and $4.8 \times 10^{-18}$, or $4.8 \times 10^{-15}$ and $4.8 \times 10^{-18}$ can be tolerated.

Generally, the enzyme will catalyze amplification reactions within a pH range that encompasses or is close to the transition pH range of the selected halochromic agent. Various enzymes can be used for the reaction, and different enzymes catalyze amplification reactions at different pH ranges. For example, Bst polymerase is believed to catalyze amplification reactions within the pH range of 6.6-9.0. The preferred starting pH for Bst polymerase is greater than 7, more preferably greater than 8.2, and more preferably at 8.8. Other examples of a preferred starting pH for Bst polymerase are found in U.S. Pat. No. 5,830,714, filed Apr. 17, 1996, hereby incorporated by reference in its entirety. In an embodiment, phenol red is coupled with Bst polymerase in a reaction mix, since the pH range at which Bst polymerase is active (6.6-9.0) encompasses the transition pH range of phenol red (6.4-8.0). In another embodiment, methyl red is coupled with U exo-Klenow fragment (polymerase for Helicase Dependent Amplification, HDA) in a reaction mix, since a starting pH at which U exo-Klenow fragment is active (around 7.5) is higher than the transition pH range of methyl red (4.8-6.2).

Other than Bst or Bst 2.0 polymerase, other enzymes capable of being used for catalyzing the amplification reaction include the polymerase from Thermus aquaticus (TAQ), DNA polymerases I-IV, Kapa Polymerase, RNA polymerases I-V, T7 RNA Polymerase, a reverse transcriptase, any DNA polymerase or RNA polymerase, a helicase, a recombinase, a ligase, a restriction endonuclease, and a single-strand binding protein. In some embodiments, an isothermal amplification reaction uses an enzyme that is a strand displacement polymerase, such as phi29-DNA-Polymerase, Klenow DNA-Polymerase, Vent DNA Polymerase, Deep Vent DNA Polymerase, Bst DNA Polymerase, 9oNm (TM) DNA Polymerase, U exo-Klenow fragment, or mutants and variants thereof. In some embodiments, suitable salts for the enzyme are also added to the reaction mix. In certain embodiments, the starting pH of the reaction mix is set based on an optimal pH for the specific enzyme used for catalyzing the amplification reaction. In an embodiment, the pH of the entire DNA sample is between pH 3 and pH 11.

In other embodiments, a fluorescent halochromic agent is used to detect protons released during amplification. The halochromic agent can change optical properties (such as amplitude and emitted wavelength) as the pH of the reaction mix changes during the amplification reaction. Fluorescent halochromic agents include fluorescein, pyranine, and pHrodo dye (Life Technologies, Carlsbad CA).

The base and/or acid added to the reaction mix maintains the starting pH of the reaction mix around or above an upper limit of the transition pH range of the halochromic agent. For example, an acid such as hydrochloric acid (HCl) or sulfuric acid (H2SO4), or a base such as sodium hydroxide (NaOH) or potassium hydroxide (KOH), can be added to the reaction mix. In some embodiments, the acid or base sets the starting pH of the reaction mix between pH 6-10, between pH 7-8, or between pH 8-8.6. In an embodiment, the reaction mix is capable of offsetting the starting pH of the reaction mix by less than 0.1 pH units. In another embodiment, the reaction mix has a starting pH lower than 2 pH units above the upper limit of the transition pH range of the halochromic agent. In further embodiments, the reaction mix has a starting pH lower than 1 pH unit, 0.5 pH units, or 0.1 pH units above the upper limit of the transition pH range of the halochromic agent. In a further embodiment, noise from non-specific amplification is minimized by setting the pH transition range sufficiently separated from the starting pH of the reaction mix, so that any color change is only achieved by a specific and sustained amplification.

In an embodiment, the reaction mix does not require any additional buffering agent for the amplification reaction, since a buffering agent could prevent large changes in pH from occurring during the amplification reaction. In another embodiment, the reaction mix contains a minimal amount of buffering agent, such that the buffering capacity of the reaction mixture is less than the expected change in pH during amplification. In some embodiments, the buffer is at a concentration between 1 mM and 3 mM. In a further embodiment, the buffer is at a concentration of 1 mM. In certain embodiments, the buffer used is Tris buffer (formulated to pH 8.8), HEPES (pH 7-9), or TAPS (pH 7-9). In another embodiment, the buffer used is a buffer having a buffering capacity equivalent to a Tris buffer at a concentration between 1 mM-19 mM in a solution having a starting pH of 8.0. This broad range of suitable buffer concentrations allows the reaction mix to resist unwanted starting pH changes during reaction setup, unlike reaction setups with minimal (<1 mM) Tris buffer equivalents (see U.S. Ser. No. 13/799,995, filed Mar. 13, 2013). These unwanted changes in pH come about due to hydronium or hydroxide ion equivalents added to the reaction via the sample reagents. As colorimetric detection and enzyme kinetics depend on the starting pH, the presence of buffer capacity in the reaction mix high enough to avoid starting pH change, but low enough to allow color change upon amplification, become important. In a further embodiment, the pH of the reaction mix is between pH 7.5-8.8. Table 1 shows various buffers having buffering capacities equivalent to a Tris buffer at a concentration between 1 mM-19 mM in a solution having a starting pH of 8.0. The buffer capacity ($\beta$) is defined as the equivalents of acid or base needed to change the pH of 1 Liter of buffer by 1 pH unit. This can be calculated as: $\beta=2.3*C*(Ka*[H3O+]/(Ka+[H3O+])2)$; where C is the buffer concentration, Ka is the dissociation constant for the buffer and [H3O+] is the hydronium ion concentration of the buffer (which is calculated from the reaction starting pH). The buffer capacity of 1 mM-19 mM Tris (in a solution having a starting pH of 8.0) was found to range from 0.000575 to 0.010873. The starting pH of the buffer was considered to be in the range of 7.5-8.8 to be compatible with the reaction biochemistry (polymerase function, nucleic acid melting, etc.). In other embodiments, the buffer has a buffering capacity equivalent to a Tris buffer at a concentration between 1.5 mM-19 mM, 2 mM-19 mM, 3 mM-19 mM, 4 mM-19 mM, 5 mM-19 mM, 6 mM-19 mM, 7 mM-19 mM, or otherwise, in a solution having a starting pH of 8.0. In other embodiments, the buffer has a buffering capacity equivalent to a Tris buffer at a concentration between 1.92 mM-36.29 mM, 3 mM-36.29 mM, 4 mM-36.29 mM, 5 mM-36.29 mM, or otherwise, in a solution having a starting pH of 8.8. In other embodiments, the buffer has a buffering capacity equivalent to a Tris buffer at a concentration between 1.48 mM-27.92 mM, 2 mM-27.92 mM, 3 mM-27.92 mM, 4 mM-27.92 mM, 5 mM-27.92 mM, or otherwise, in a solution having a starting pH of 7.5.

TABLE 1

Buffer Capacity Table

| Buffer | Full Chemical Name | pKa at 25° C. | Starting Reaction pH | Min Conc (mM) | Max Conc (mM) |
|---|---|---|---|---|---|
| Tris | tris(hydroxymethyl)methyl-amine | 8.06 | 8.8 | 1.92 | 36.29 |
|  |  |  | 8.0 | 1.00 | 19.00 |
|  |  |  | 7.5 | 1.48 | 27.92 |
| TAPS | N-Tris(hydroxymethyl)methyl-3-aminopropanesulfonic acid | 8.43 | 8.8 | 1.19 | 22.55 |
|  |  |  | 8.0 | 1.27 | 23.94 |
|  |  |  | 7.5 | 2.66 | 50.25 |
| Bicine | N,N-bis(2-hydroxyethyl)glycine | 8.35 | 8.8 | 1.29 | 24.46 |
|  |  |  | 8.0 | 1.17 | 22.15 |
|  |  |  | 7.5 | 2.31 | 43.59 |
| Tricine | N-tris(hydroxymethyl) methylglycine | 8.15 | 8.8 | 1.67 | 31.63 |
|  |  |  | 8.0 | 1.03 | 19.48 |
|  |  |  | 7.5 | 1.67 | 31.63 |

TABLE 1-continued

Buffer Capacity Table

| Buffer | Full Chemical Name | pKa at 25° C. | Starting Reaction pH | Min Conc (mM) | Max Conc (mM) |
|---|---|---|---|---|---|
| TAPSO | 3-[N-Tris(hydroxy-methyl)methylamino]-2-hydroxypropanesulfonic acid | 7.635 | 8.8<br>8.0<br>7.5 | 4.17<br>1.19<br>1.02 | 78.90<br>22.45<br>19.37 |
| HEPES | 4-(2-hydroxyethyl)-1-piperazineethanesulfonic acid | 7.48 | 8.8<br>8.0<br>7.5 | 5.74<br>1.40<br>1.00 | 108.45<br>26.54<br>18.92 |
| TES | N-tris(hydroxymethyl)methyl-2-aminoethanesulfonic acid | 7.4 | 8.8<br>8.0<br>7.5 | 6.79<br>1.56<br>1.01 | 128.39<br>29.46<br>19.16 |
| MOPS | 3-(N-morpholino)propane-sulfonic acid | 7.2 | 8.8<br>8.0<br>7.5 | 10.46<br>2.12<br>1.12 | 197.77<br>40.03<br>21.26 |
| PIPES | 1,4-piperazinediethane-sulfonic acid acid | 6.76 | 8.8<br>8.0<br>7.5 | 27.91<br>4.86<br>1.92 | 500.00<br>91.88<br>36.29 |
| SSC | Saline Sodium Citrate | 7.0 | 8.8<br>8.0<br>7.5 | 16.28<br>3.03<br>1.37 | 300.00<br>57.20<br>25.90 |

In an embodiment, a magnesium compound is added to the reaction mix, because magnesium promotes nucleotide incorporation into the template and influences the activity of the polymerase. In a further embodiment, the concentration of a magnesium compound (such as magnesium sulfate) in the reaction mix is at least 0.5 mM, at least 1 mM, at least 2 mM, or at least 4 mM. In an embodiment, the concentration of added magnesium ion is dependent on the concentration of dNTPs, nucleic acid template, and primers. In an embodiment, the ratio of dNTPs to magnesium sulphate in the reaction mix is less than 1:2, less than 1:3, less than 1:4 or less than 1:5.

In some embodiments, monovalent cations are added to the reaction mix. Monovalent cations include potassium, ammonium, and quaternary ammonium, among others. Monovalent cations can affect the melting characteristics of the nucleic acid template and improve the efficiency of the enzyme. In an embodiment, potassium is in the reaction mix at a concentration of less than 50 mM, or less than 15 mM. In another embodiment, quaternary ammonium salts are in the reaction mix at a concentration of greater than 2 mM, greater than 5 mM, or greater than 8 mM. In another embodiment, an ammonium compound (such as ammonium chloride) is in the reaction mix at a concentration of less than 15 mM, or less than 10 mM. Ammonium (NH4+) has some buffering capability, thus the final concentration of ammonium compounds in the reaction mix should be minimized while maintaining optimal amplification yield.

In an embodiment, the concentrations of other reagents of the reaction mix are kept at amounts as generally used in amplification reactions. See Notomi T et. al. Nucleic Acids Res. 2000 Jun. 15; 28 (12): E63; Nature Protocols 2008, Loop-mediated isothermal amplification (LAMP) of gene sequences and simple visual detection of products, 2008 3 (5): pg 880, hereby incorporated by reference in its entirety. In an embodiment, the Bst or Bst 2.0 enzyme is used, and the amount of enzyme is at least 0.8 Unit per microliter of combined fluid. In this embodiment, Betaine is also present in the reaction mix at a concentration between 0-1.5 M or 0.8M-1 M, and the total concentration of primers is between 3.6 µM and 6.2 µM. In some embodiments, any of the following reagents is present in the reaction mix: Tris buffer (pH 8.8) at 20 mM, KCl at 10 mM, MgSO$_4$ at 8 mM, (NH$_4$)$_2$SO$_4$ at 10 mM, TWEEN® 20 at 0.1%, Betaine at 0.8 M, dNTPs at 1.4 mM each, MnCl$_2$ at 0.5 mM, FIP at 1.6 µM, F3 at 0.2 µM, B3 at 0.2 µM, primers at a total concentration of 5.2 µM (2*(1.6+0.8+0.2), and Bst/Bst 2.0 at 8 U per 10 µL.

The above reagent concentrations have been found to provide good amplification yield and low buffering capacity so that a halochromic pH sensor can be used to detect protons released during the amplification reaction. In some embodiments, the concentrations of reaction mix reagents depend on the enzyme selection. In further embodiments, guidance regarding appropriate reagent concentrations is available from the enzyme manufacturers. In an embodiment, the ratio of the sample volume to the reaction mix volume is such that the sample is diluted between 5% and 40% when the reaction mix is added.

In some embodiments, amplification reaction reagents are stored separately before being added to a reaction mix, since some reagents have specific required conditions for stability. For example, the enzyme can be stored long term in a moderately buffered solution separate from the other reagents to ensure stability of the enzyme. Upon mixing with the remaining reagents in the reaction mix, the buffering agent becomes sufficiently diluted so as not to significantly mask a pH change. In addition, primers for specific genes of interest can be provided in a separate solution or in a lyophilized form.

In some embodiments, the amplification reaction is performed within a microtube. In other embodiments, the amplification reaction is performed within a fluidic or microfluidic structure. In some embodiments, the fluidic or microfluidic structure is a well, chamber, or channel that receives the reagents and the nucleic acid sample separately, and then mixes the components together. In another embodiment, the fluidic or microfluidic structure is a well, chamber, or channel that receives the pre-mixed reaction mix. In a further embodiment, the fluidic or microfluidic structure possesses a long optical path for colorimetric observation, or a fluorescent/absorbance excitation source and detector. In another embodiment, the fluidic or microfluidic structure receives the reagents in a lyophilized form, and subsequently receives the nucleic acid sample and hydration solution. In an embodiment, a chamber fluidic or microfluidic structure has a channel depth ranging between 50 µm-400 µm or greater. In a further embodiment, colorimetric observation is accomplished for channel depths (path length) of 50 µm, 50 µm-400 µm, or 50 µm or greater.

Some embodiments include a kit for colorimetric detection of an amplification product. The kit can include one or more halochromic agents, one or more enzymes for catalyzing an amplification reaction, and instructions for contacting a sample with a reaction mix including the buffer and the enzyme and the halochromic agent under conditions that an amplification reaction occurs and produces an amplification reaction product if the sample contains a target nucleic acid template molecule, the reaction mix having a starting pH, and if the target nucleic acid template molecule is present, the amplification reaction changes the starting pH of the reaction mix to cause a detectable colorimetric change of the halochromic agent, thereby indicating the presence of the target nucleic acid, and if the target nucleic acid template molecule is not present, the amplification reaction does not generate a sufficient number of protons to change the starting pH of the reaction mix sufficient to cause a detectable colorimetric change of the halochromic agent, thereby indicating that the amplification reaction product has not been produced. In another embodiment, the instructions are for contacting a nucleic acid template molecule with the halochromic agent and enzyme in a reaction mix, under conditions that result in (1) an amplification reaction that amplifies the nucleic acid template molecule to produce an amplification reaction product, and (2) generation of a sufficient number of protons so that an ending pH of the reaction mix is sufficiently low to produce a detectable colorimetric change of the halochromic agent, thereby indicating that the amplification reaction product has been produced. In further embodiments, the kit also includes an acid or base, dNTPs, primers, and monovalent cations. In a further embodiment, the kit includes the following reagents at the following concentrations:

Bst or Bst 2.0 polymerase, at least 0.8 Unit per microliter;
Betaine at 0.8 M;
Primers at 3.6 µM total;
  FIP and BIP primers at 1.6 µM
  F3 and B3 at 0.2 µM
Magnesium sulfate at 8 mM;
Ammonium sulfate at 10 mM;
Potassium chloride at 10 mM;
Sodium hydroxide to set the starting pH of the reaction mix; TWEEN® 20 at 0.1%;
dNTP's at 1.4 mM each;
Phenol red at 50 µM.

In a further embodiment, the kit includes LoopF and LoopB primers at 0.8 µM each.

Kits

The embodiments disclosed herein also include kits including the subject devices and which can be used according to the subject methods. The subject kits can include two or more, e.g., a plurality, three or less, four or less, five or less, ten or less, or fifteen or less, or fifteen or more, biological sample assay optical property modifying devices or components thereof, according to any of the embodiments described herein, or any combinations thereof.

The kits can include one or more compositions and/or reagents, such as any of those described herein, e.g., optical property modifying reagents, amplification compositions, preparation solutions and/or buffers, which can be stored in the kits in containers separate from the devices. In addition, the kits can include any device or other element which can facilitate the operation of any aspect of the kits. For example, a kit can include one or more devices for preparing a sample and/or analyzing one or more characteristics of a sample, e.g., a prepared sample. Kits can also include packaging, e.g., packaging for shipping the devices without breaking.

In certain embodiments, the kits which are disclosed herein include instructions, such as instructions for using devices. The instructions for using devices are, in some aspects, recorded on a suitable recording medium. For example, the instructions can be printed on a substrate, such as paper or plastic, etc. As such, the instructions can be present in the kits as a package insert, in the labeling of the container of the kit or components thereof (i.e., associated with the packaging or subpackaging etc.). In other embodiments, the instructions are present as an electronic storage data file present on a suitable computer readable storage medium, e.g., Portable Flash drive, CD-ROM, diskette, on the cloud, etc. The instructions may be storable and/or reproducible within one or more programs, such as computer applications. The instructions can take any form, including complete instructions for how to use the devices or as a website address with which instructions posted on the world wide web can be accessed.

Utility

As demonstrated above, the subject devices and methods are directed to performing biological assays by modifying optical properties of biological samples or aspects thereof. The subject devices and methods sufficiently modify an optical property to allow detection of the modified optical property by an un-assisted human eye. As such, the content of the subject disclosure eliminates a need for complex evaluation techniques or equipment to read or interpret a signal generated by a biological assay. Because a user can recognize a modified optical property with a user's eye, performing an assay with the subject methods can reduce time and expense compared to performing such an assay using other equipment or methods. The subject devices can also be finely tuned to provide efficient energy conduction, e.g., heat or electrical energy, into a fluidic network and/or specific variations in optical properties such as adhesive color. Also, previous biological assays have also involved a high degree of complexity in analysis, e.g., have required the use of one or more computer, which in turn has provided limited reliability and usability. Accordingly, the subject methods and devices are cheaper, less complex and/or more accurate than other such devices or methods.

Furthermore, previous methods of assembling biological assay devices have included patterning a substrate layer, e.g., a layer of glass, silicon or polymer, and then bonding it to a non-patterned sealing layer using chemical or physical bonds. Once the fluidic device was assembled, e.g., assembled by being bonded and sealed, then is has been integrated into a housing or cassette that provides additional functionality required to utilize the fluidic system. However, many microfluidic device bonding techniques have had the potential to damage any fragile pre-loaded reagents. By employing the device conformation disclosed herein, such difficulties are avoided since the adhesive layer can be employed for simultaneously sealing the microfluidic system and integrating into the final assembly while preserving reagent functionality, such as functionality of reagents pre-loaded into reaction chambers. As such, the subject methods and devices simplify the operation of such devices, as well as the manufacturing of such devices while improving effectiveness in generating an assay result.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* $3^{rd}$ Ed. (Plenum Press) Vols A and B (1992).

Figure 3:
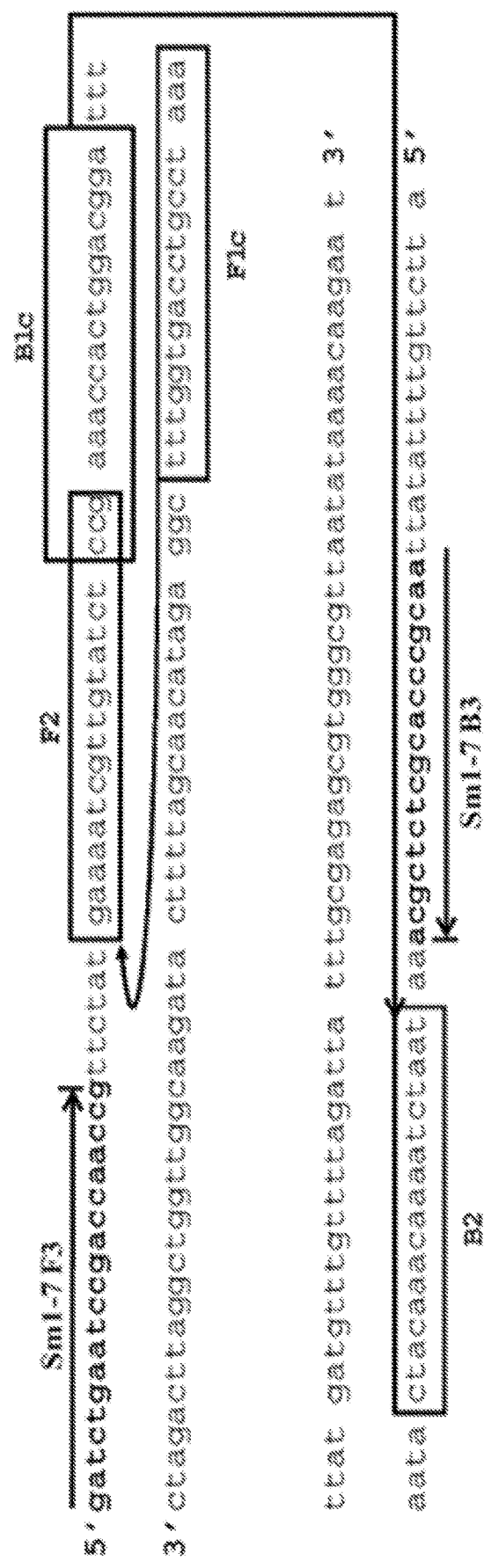
FIG. 3 shows the DNA sequence of a template nucleic acid molecule target region from Schistosoma mansoni (SEQ ID NO: 23), according to an embodiment.

Example 1: Colorimetric Detection of a Nucleic Acid Amplification Reaction Product In an assay for colorimetric detection of a nucleic acid amplification reaction product, the following reagents were mixed together to produce a 2× reagent mix:
 Magnesium Sulphate (Sigma Aldrich) at 16 mM
 Ammonium Sulphate (Sigma Aldrich) at 20 mM
 Potassium Chloride (Sigma Aldrich) at 20 mM
 Sodium hydroxide (Sigma Aldrich) at a concentration that sets the starting pH of the reagent mix to 8.8 pH The reagent mix was adjusted to an initial pH of 8.8 to enable efficient initial polymerization. The reagent mix was autoclaved for 1 hour for sterilization. The following ingredients were then added (in a sterile form) to the reagent mix to generate the reaction mix:
 TWEEN® 20 (Sigma Aldrich) at 0.1% (v/v)
 dNTPs (NEB) at 1.4 mM each
 Phenol Red (Sigma Aldrich) at 50 µM
 Bst polymerase (NEB) at 0.8 Unit per microliter (the enzyme storage buffer contributing 1 mM Tris buffer, 5 mM KCl, 0.01 mM EDTA, 0.1 mM DTT, 0.01% TRITON X100™ (v/v) and 5% Glycerol ((w/v) to the reaction mix)
 Betaine (Sigma Aldrich) at 0.8 M Primers and a nucleic acid template were added to the reaction mix. The primers were designed for LAMP and included two pairs of primers (solubilized in 1X Tris EDTA buffer) at a total concentration of 3.6 µM as described above. Primer F3 has the sequence: GATCTGAATCCGAC-CAACCG (SEQ ID NO: 1); primer B3 has the sequence: AACGCCCACGCTCTCGCA (SEQ ID NO: 2); the primer FIP has the sequence: AAATCCGTCCAGTGGTTTTTTT-GAAAATCGTTGTATCTCCG (SEQ ID NO: 3); and the primer BIP has the sequence: CCGAAACCACTGGACG-GATTTTTATTTTTAATCTAAAACAAACATC (SEQ ID NO: 4). The nucleic acid template molecule was purified from Schistosoma mansoni. FIG. 3 shows the SM1-7 target region of the nucleic acid template molecule (see Hamburger et al, Detection of Schistosoma mansoni and Schistosoma haematobium DNA by Loop-Mediated Isothermal Amplification: Identification of infected Snails from Early Prepatency, *Am J Trop Med Hyg,* 2010). The positive test reactions contained template DNA, and the negative control reactions contained water. The reaction mixes had a starting pH in the range of 7.5-8.5. The reaction mixes were heated in micro-tubes to 63° C. on a thermocycler to allow template amplification. After a predetermined reaction period of 45 minutes, during which sufficient template amplification occurred, the resultant color of the reaction mix was visually observed.

Figure 4:
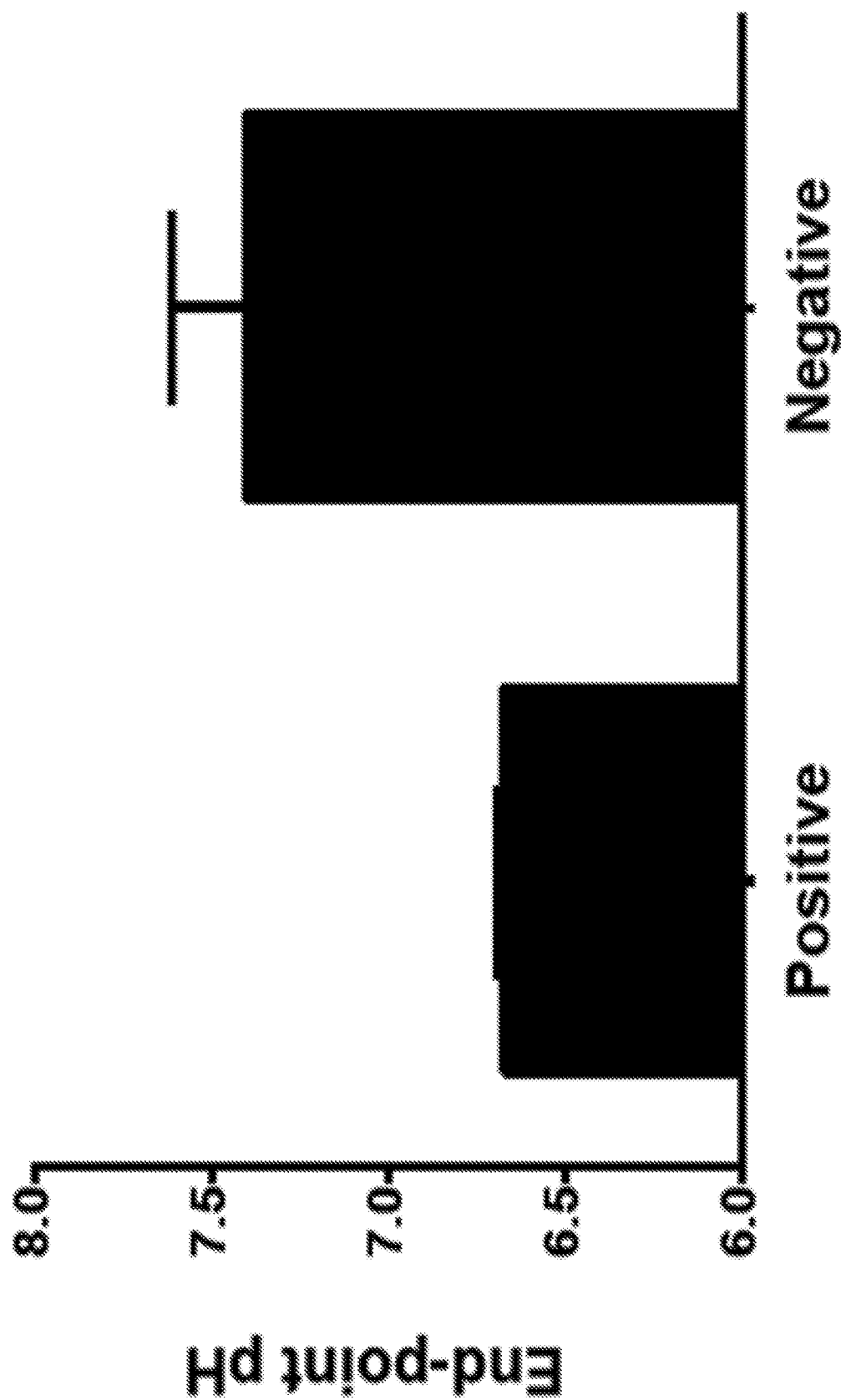
FIG. 4 is a graph indicating pH measurements for positive and negative isothermal amplification reactions, according to an embodiment.
Figure 5:
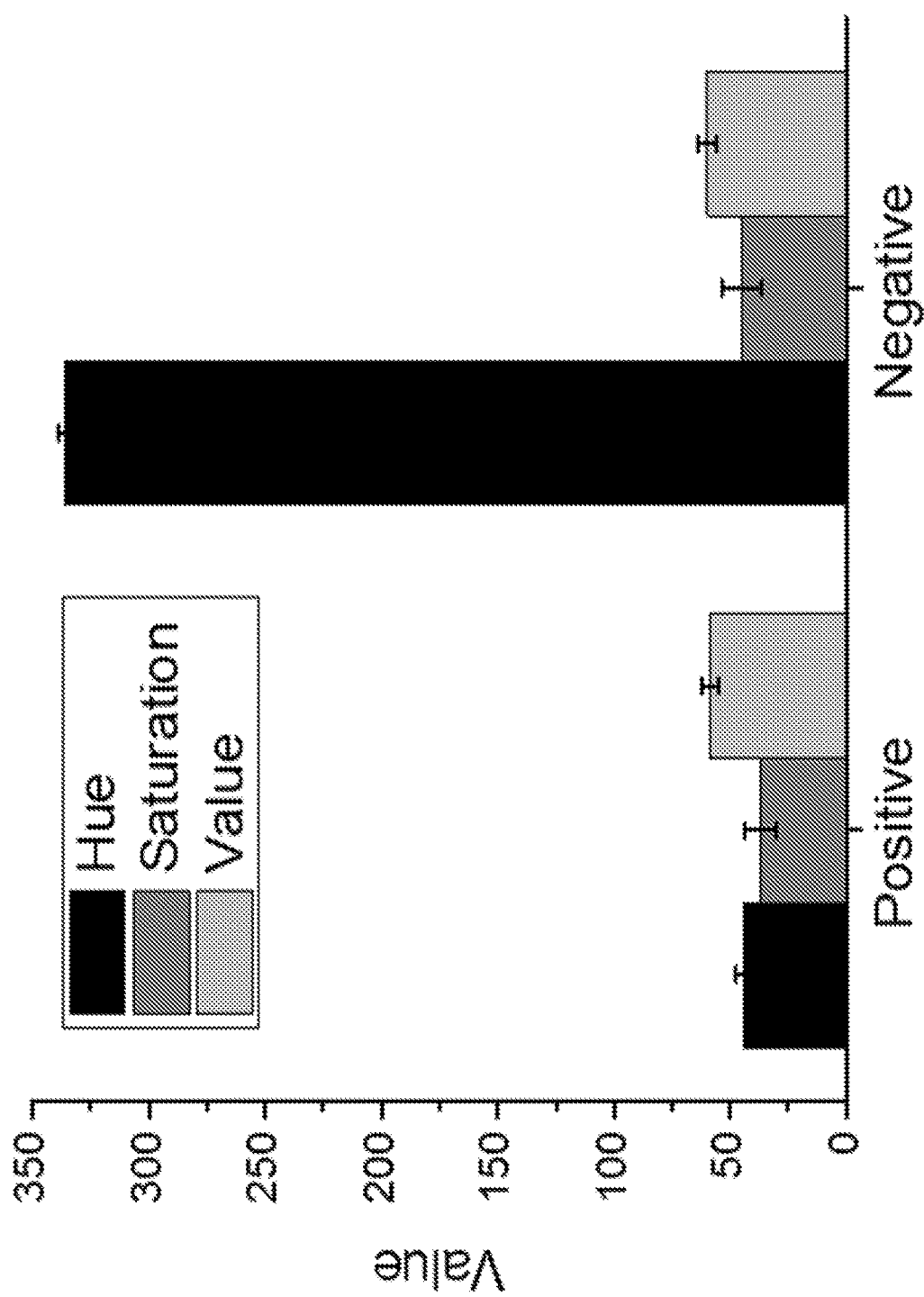
FIG. 5 is a graph showing the detection of color (hue) of positive and negative isothermal amplification reactions at the reaction endpoints, according to an embodiment.
Figure 6:
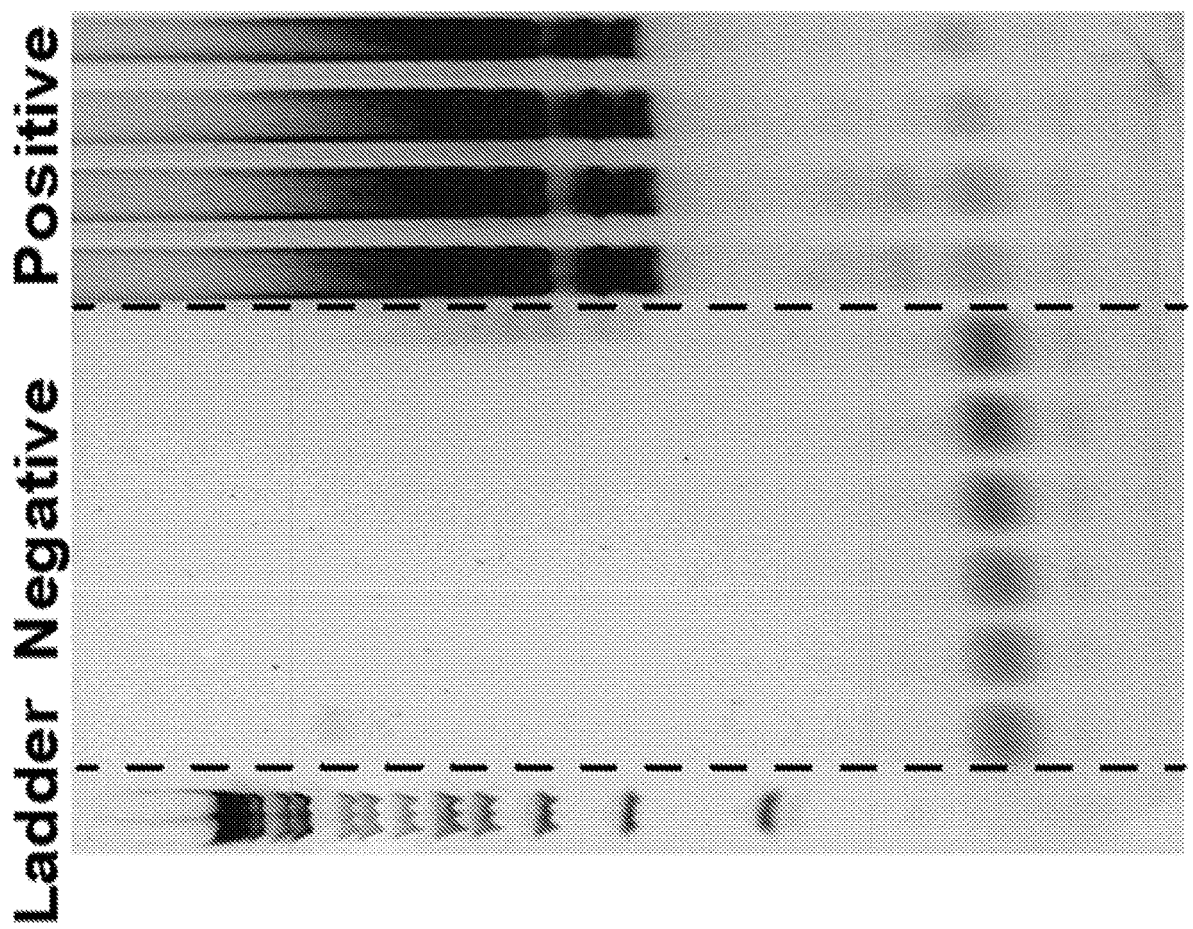
FIG. 6 shows the results of a gel electrophoresis assay of positive and negative isothermal amplification reaction products, according to an embodiment.

During the amplification process, the pH of the reaction mix was reduced from 7.5-8.5 to around 6.6 in a repeatable fashion. FIG. 4 is a graph showing the pH measurements for repeated positive (test) and negative (negative control) amplification reactions. The halochromic agent used was Phenol red, which has a transition pH range of 6.8-8.2. Phenol red changes color over this transition pH range from red to yellow (when the pH is lowered from the upper pH limit to the lower pH limit). In the assay, the reaction mix changed color from red (at pH 8.0) to yellow (at pH 6.6) in response to the pH change during nucleic acid amplification. FIG. 5 is a graph showing the difference in contrast value using HSV (hue, saturation, value) of images of the reaction mixes of a positive and negative amplification reaction at the reaction endpoints. The color change is quantitatively demonstrated in the hue variable. To confirm that the color change was due to target DNA amplification, endpoint reactions were analyzed using gel electrophoresis to verify the presence of amplicons (FIG. 6).

Using this method, amplification of a DNA template can be easily observed, either at the reaction end-point or in real-time throughout the reaction, by visually observing the color change in the reaction mix, or by measuring the absorbance or fluorescence of the reaction mix. This mechanism generates much larger contrast in comparison to other colorimetric detection techniques and can be imaged without the need of expensive optical instrumentation.

Example 2: Detection of LAMP Amplification Using a Visual Halochromic Aunt

LAMP reactions were performed with a reaction mix comprising of: 10 mM $(NH_4)_2SO_4$, 15 mM KCl, 0.1 mM EDTA, 0.1 mM DTT, 0.01% TRITON X100™ (v/v), 5% Glycerol, 8 mM $MgSO_4$, 1.4 mM each dNTPs, 0.1% v/v TWEEN® 20, 0.8 M Betaine. Three primer pairs, specific to different targets, were added to a final concentration of 1.6 µM each for FIP/BIP, 0.2 µM each for F3/B3, 0.4 µM each for LoopB/F. The final reaction volume is 10 µL and was held at 63° C. for different incubation times.

Figure 7:
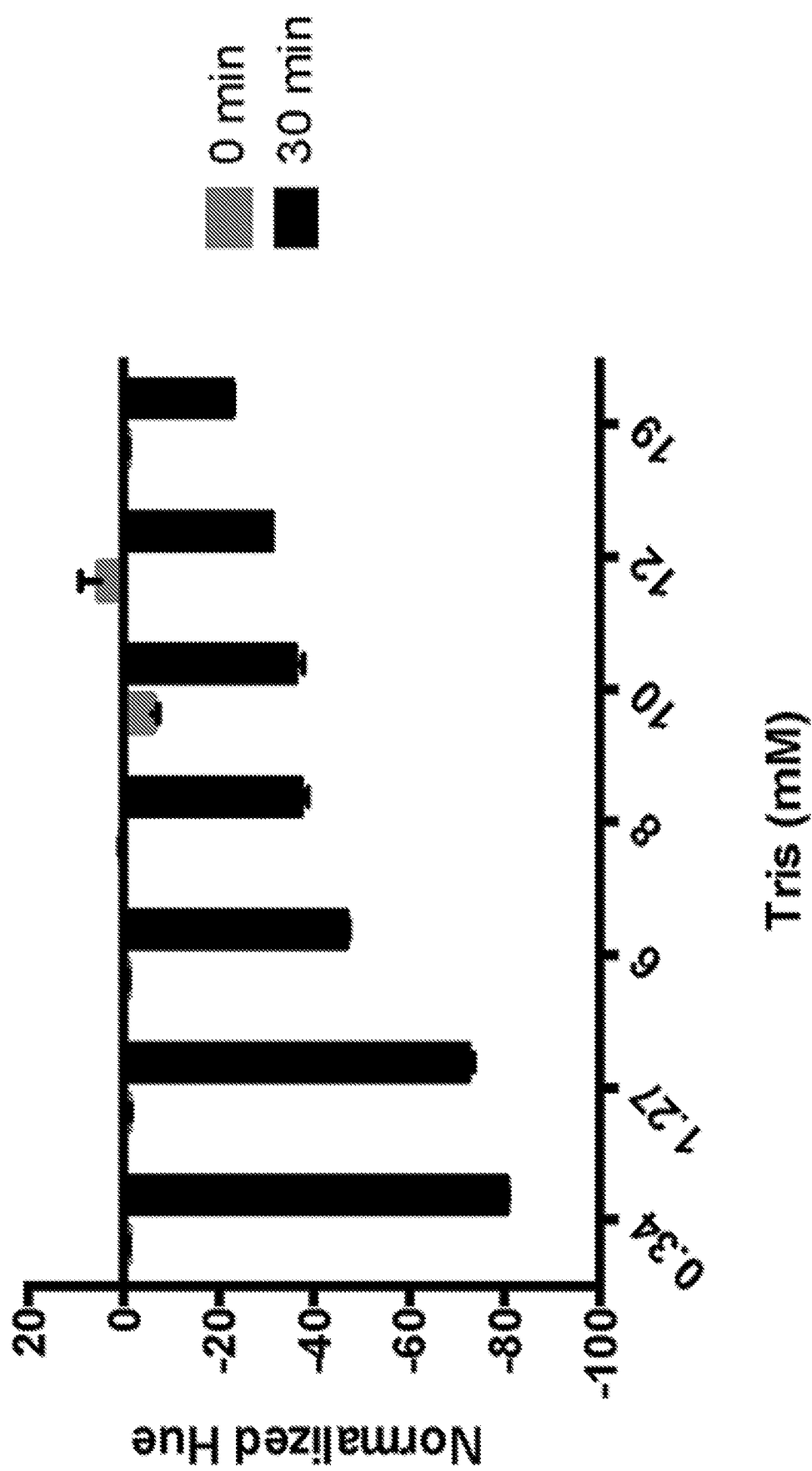
FIG. 7 shows the normalized hue values for amplification reactions using various Tris buffer concentrations, according to an embodiment.

In FIG. 7, the final Tris buffer concentration of the reaction mix was varied from 0.34 mM to 19 mM (by varying amount of Tris buffer formulated to pH 8.8). Reactions were performed with primers for lambda phage DNA, 5 ng of lambda DNA (New England Biolabs), 0.8 U/µl Bst 2.0 DNA polymerase (New England Biolabs) and 0.2 mM Neutral Red (Sigma Aldrich). The reaction tubes were then imaged and the Normalized Hue value was calculated for the color of the reaction mix. The Normalized Hue value was defined as the difference in Hue values between a positive and a no-template negative reaction. A color change, indicated by a change in the Normalized Hue value above the visualization threshold (dotted line), was observed for buffer concentrations as high as 19 mM Tris. This indicates that reaction mix with buffer capacities equivalent to >1 mM and <19 mM Tris allow enough pH change for visual color change detection.

Figure 8:
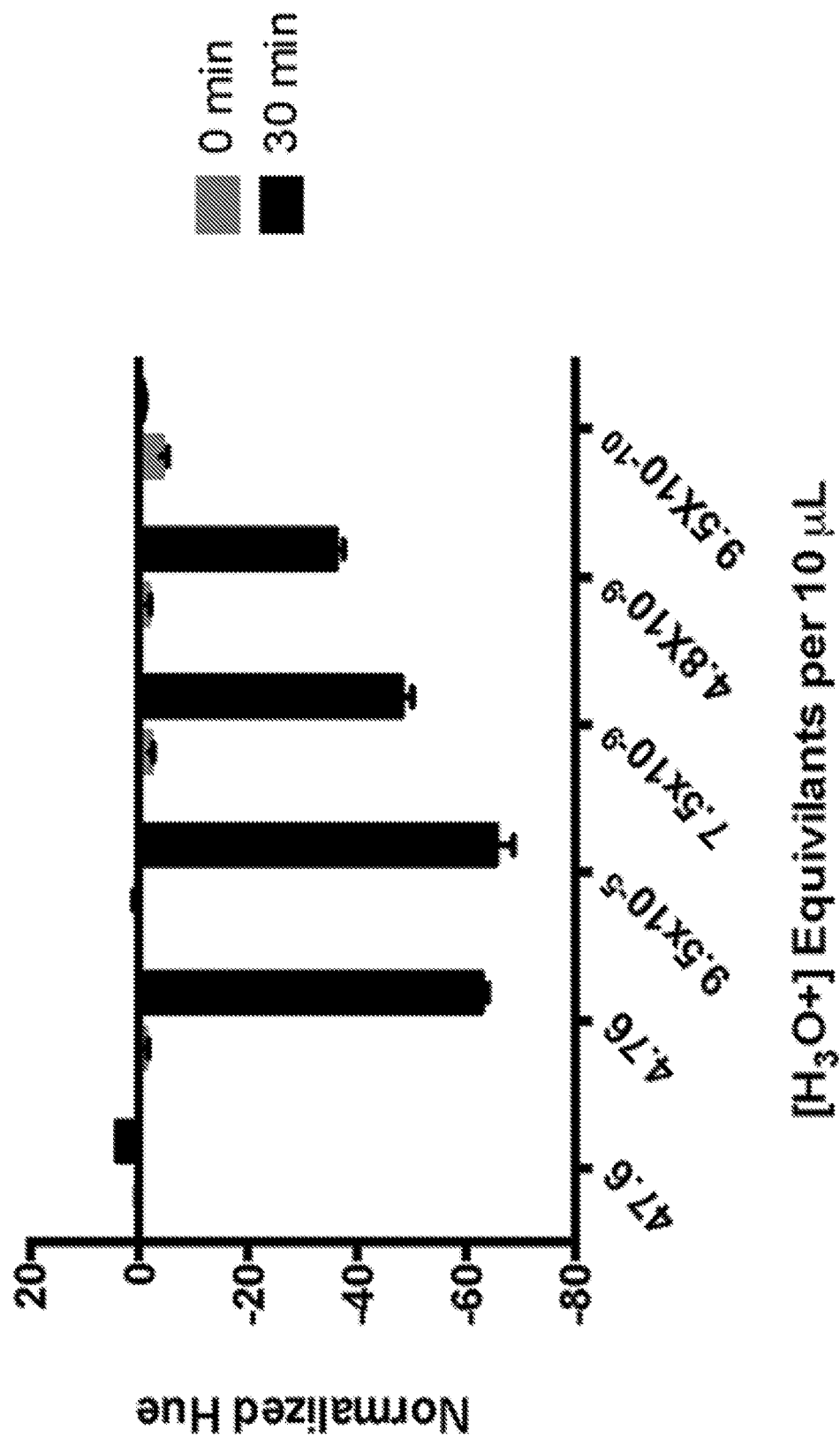
FIG. 8 shows the normalized hue values for amplification reactions using varying amounts of additional hydronium ion equivalents, according to an embodiment.

In FIG. 8, the tolerance of this visual detection method to excess hydronium ions added to the reaction mix was evaluated. This tolerance is important to allow the use of a wide variety of DNA samples which can add a range of hydronium or hydroxide ion equivalents to the reaction. Reactions were performed with 2 mM final Tris buffer concentration, 5 ng lambda DNA target, 0.8 U/μL Bst DNA polymerase and 0.2 mM Neutral Red halochromic agent. The change in Normalized Hue value indicates that this visual detection chemistry works with $4.8 \times 10^{-9}$ till $4.8 \times 10^{-18}$ additional hydronium ion equivalent per 10 μL reaction.

Figure 9A:
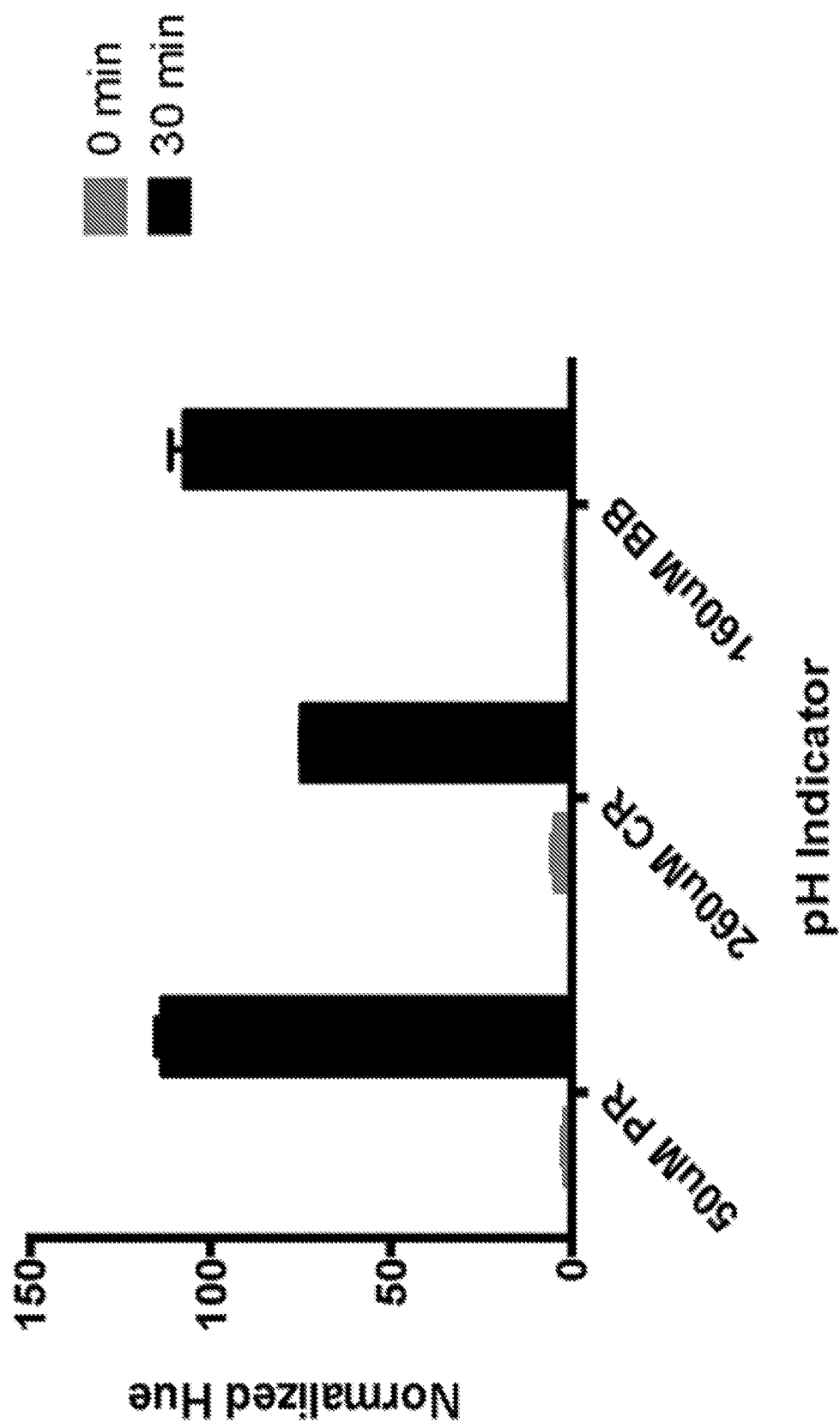
FIGS. 9A, 9B, 9C, and 9D show the normalized hue values for amplification reactions using various halochromic agent concentrations, according to an embodiment.
Figure 9B:
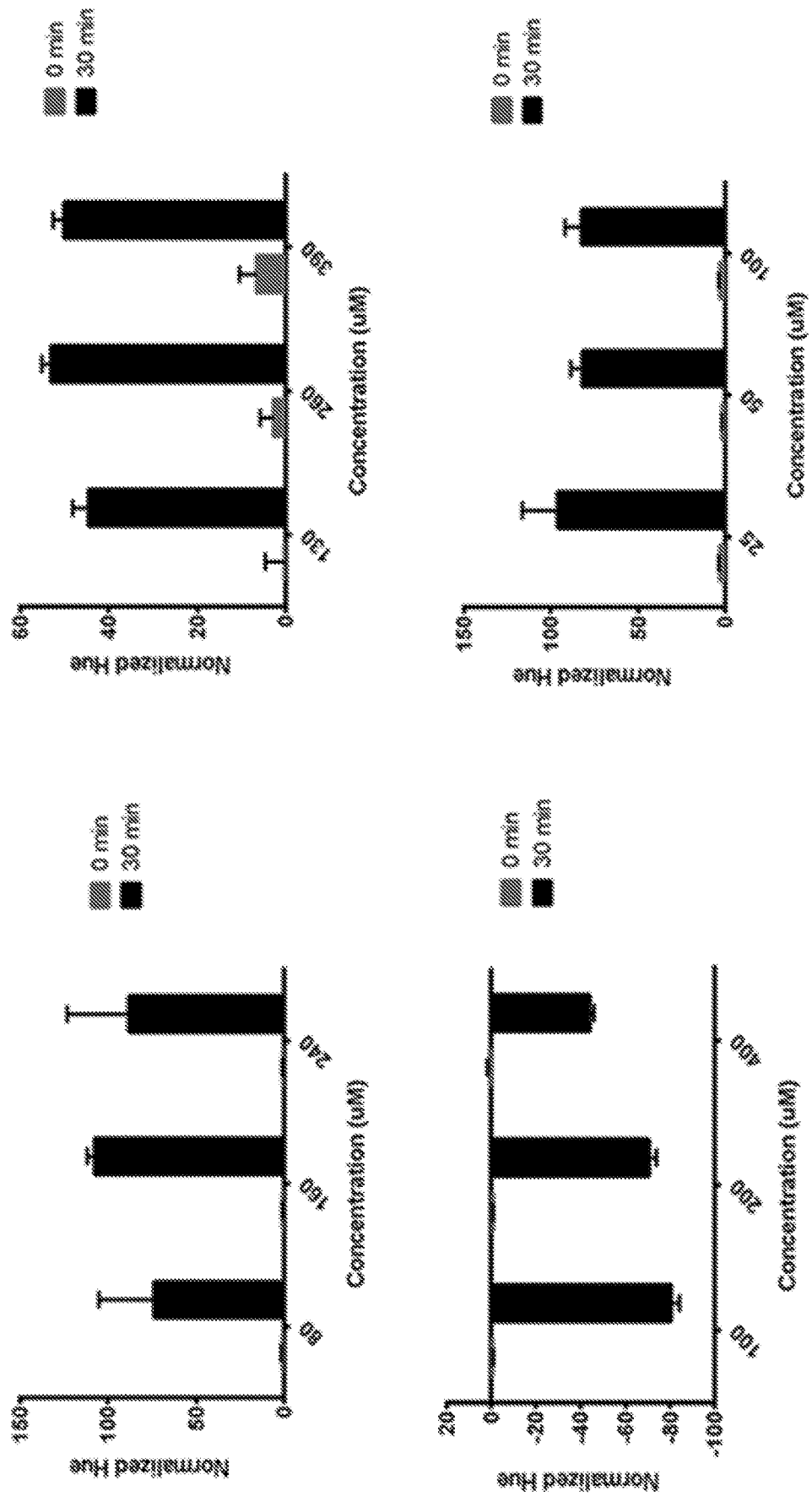
Figure 9C:
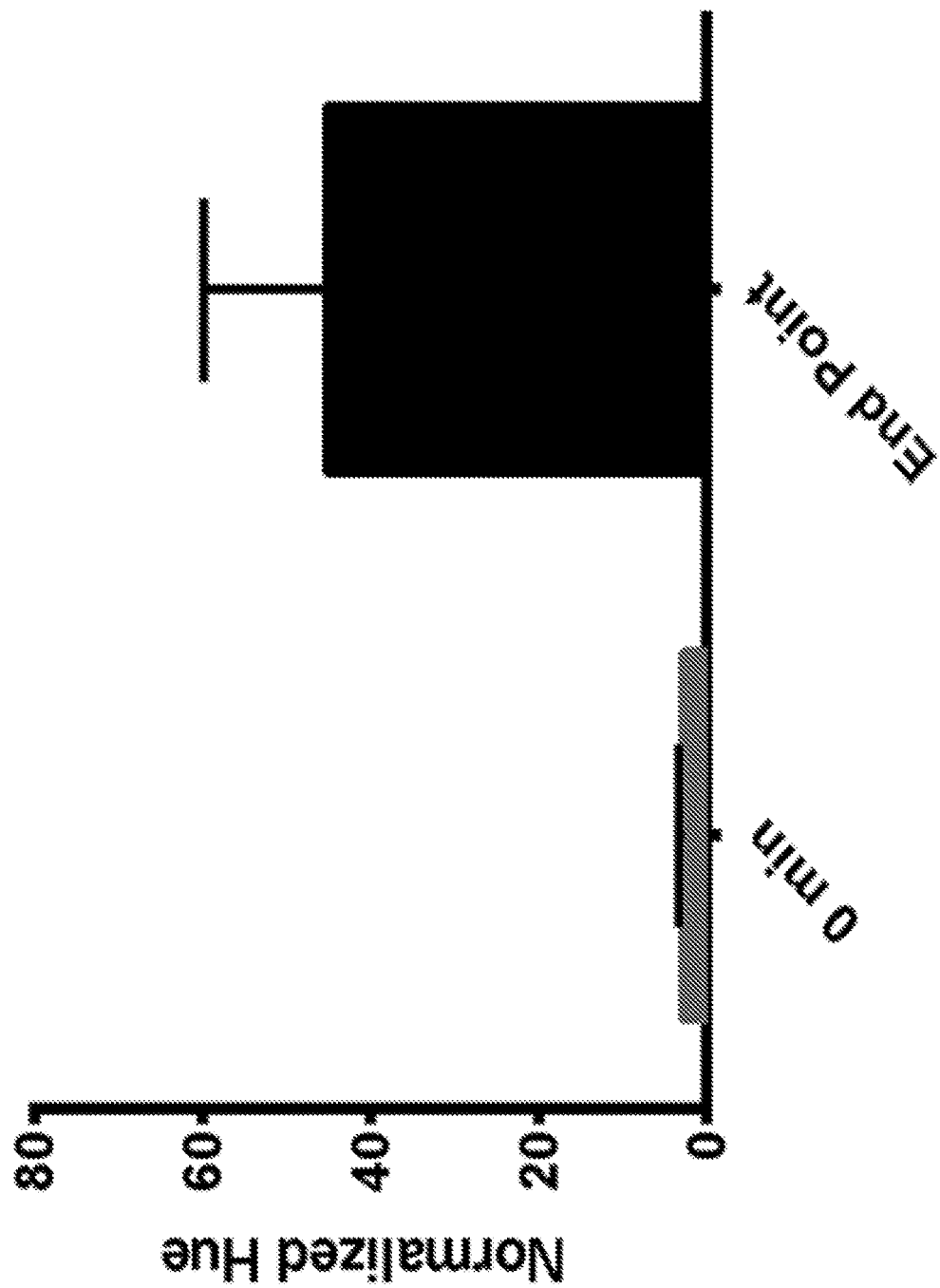
Figure 9D:
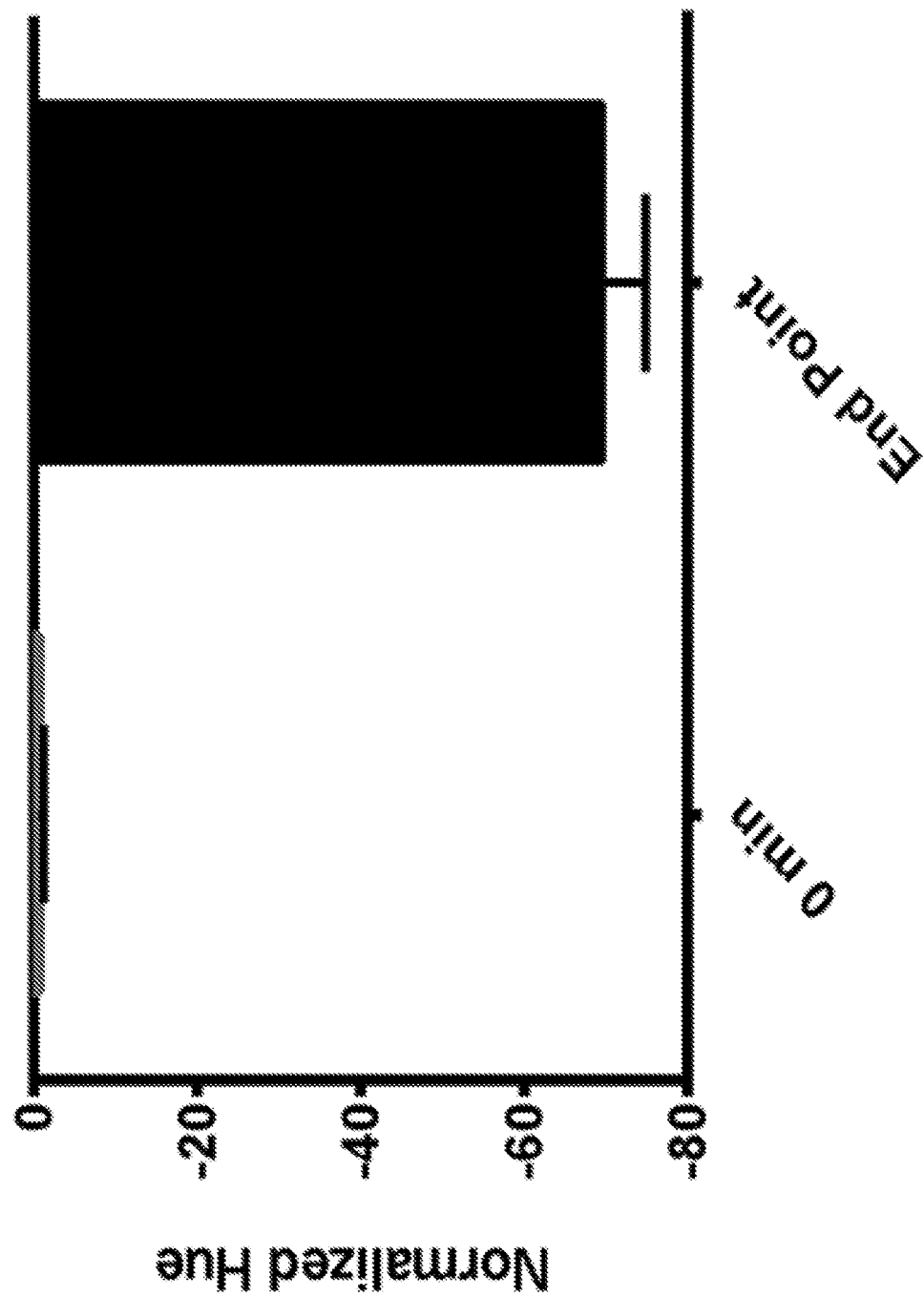

In FIGS. 9A-9D, the compatibility of different pH indicators and amplification targets with visual detection of LAMP amplification was evaluated. The reactions were performed with final Tris buffer concentration in the range of 1.2-1.3 mM and 0.8 U/μL Bst DNA polymerase. Three different indicator were tested with 5 ng lambda DNA target: 50 μM Phenol Red, 260 μM Cresol Red and 160 μM Bromothymol Blue (FIG. 9A). High contrast change in the normalized hue value was observed for all indicators tested.

Concentration sweeps were also performed for these indicators Bromothymol Blue (FIG. 9B top left), Cresol Red (FIG. 9B top right), Neutral Red (FIG. 9B bottom left) and Phenol Red (FIG. 9B bottom right) with Lambda target, which demonstrated the wide range of concentrations that are compatible with the chemistry. LAMP assays using 130 ng Schistosoma mansoni gDNA with 50 μM Phenol Red (FIG. 9C) and Human GAPDH mRNA with 0.2 mM Neutral Red (FIG. 9D) were also tested visual detection of these targets was demonstrated at end-point.

Figure 10:
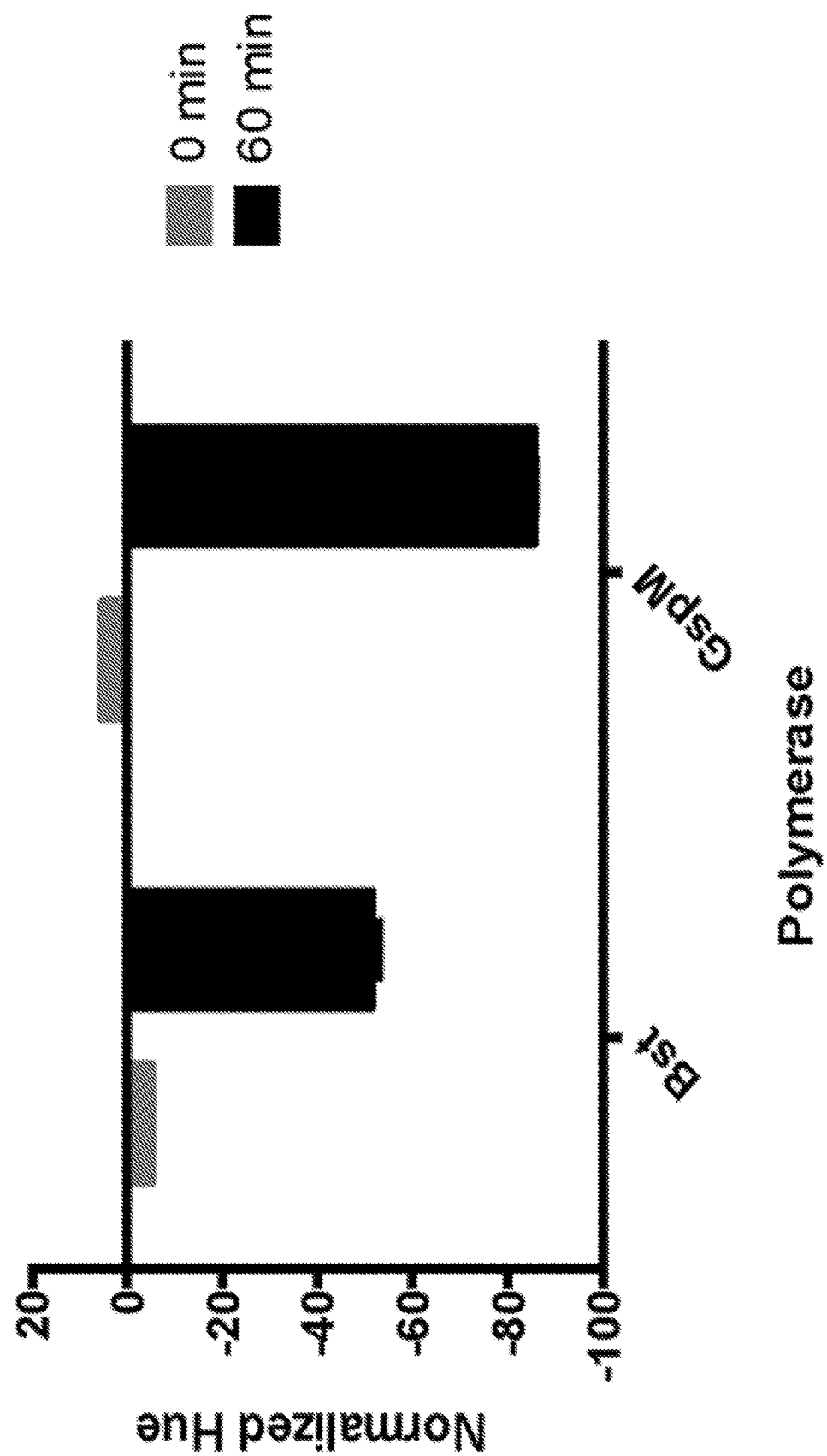
FIG. 10 shows the compatibility of different polymerases with visual detection of LAMP amplification, according to an embodiment.

In FIG. 10, the compatibility of different polymerases with visual detection of LAMP amplification was evaluated. The reactions were performed with 1.3 mM final Tris buffer concentration, 5 ng lambda DNA target and 0.2 mM Neutral Red. 0.8 U/μl of two different polymerases, Bst 2.0 and Gspm 2.0 (OptiGene), were used. High contrast color change was observed for both polymerases after 60 minutes of incubation (FIG. 10).

TABLE 2

Sequences Used

| | |
|---|---|
| Lambda FIP | SEQ ID NO: 5 |
| Lambda BIP | SEQ ID NO: 6 |
| Lambda F3 | SEQ ID NO: 7 |
| Lambda B3 | SEQ ID NO: 8 |
| Lambda Loop F | SEQ ID NO: 9 |
| Lambda Loop B | SEQ ID NO: 10 |
| *Schistosoma* F3 | SEQ ID NO: 1 |
| *Schistosoma* B3 | SEQ ID NO: 2 |
| *Schistosoma* FIP | SEQ ID NO: 3 |
| *Schistosoma* BIP | SEQ ID NO: 4 |
| GAPDH F3 | SEQ ID NO: 11 |
| GAPDH B3 | SEQ ID NO: 12 |
| GAPDH FIP | SEQ ID NO: 13 |
| GAPDH BIP | SEQ ID NO: 14 |
| GAPDH Loop F | SEQ ID NO: 15 |
| GAPDH Loop B | SEQ ID NO: 16 |

Figure 11A:
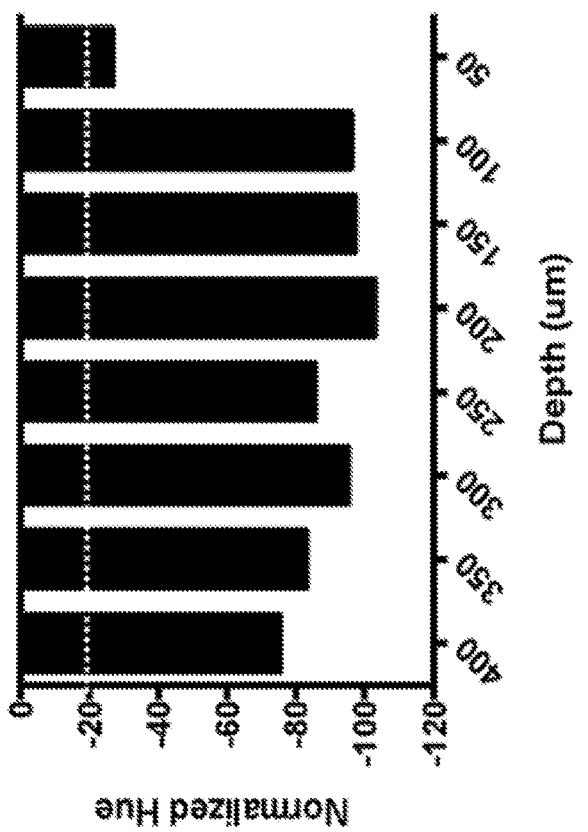
FIGS. 11A and 11B show the normalized hue values for amplification reactions using varying channel depths, according to an embodiment.
Figure 11B:
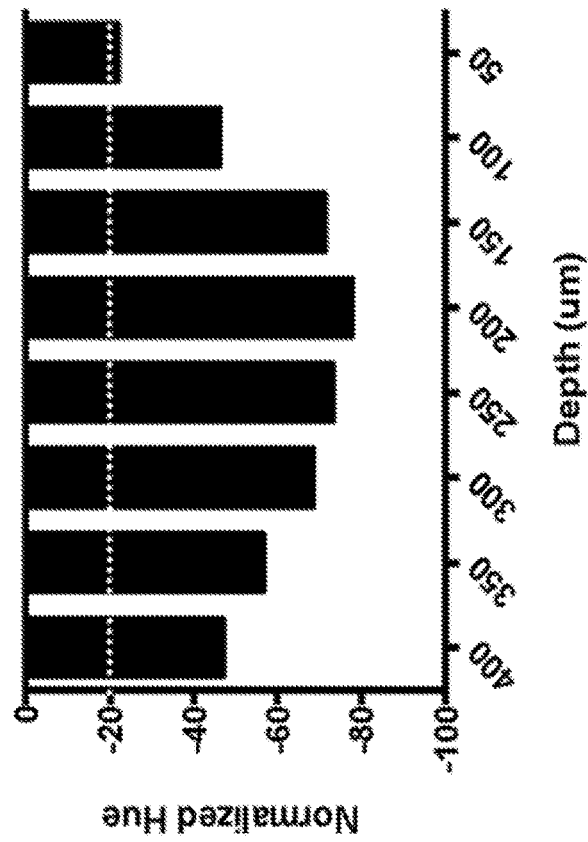

Example 3: Visual Detection of LAMP Amplification in Sub-Millimeter Path Lengths LAMP reactions were performed as in Example 1 with 1.3 mM final Tris buffer concentration (buffer formulated to pH 8.8), 0.8 U/μl of Bst 2.0 DNA Polymerase, 5 ng lambda DNA template and 0.2 mM Neutral Red or 160 μM Bromothymol Blue. Both the positive and the no-template negative reactions were added after amplification to flow chambers with varying channel depths (FIG. 11A for Neutral Red and FIG. 11B for Bromothymol Blue). These flow chambers were machined in acrylic with channel depths ranging from 50 μm to 400 μm. High contrast color difference (above the visual detection threshold; dotted line) between the positive and the negative reactions was observed for channel depths of 50 μm and above. This demonstrates that this visual detection chemistry is amenable for use in reaction chambers with sub-millimeter path lengths (depths) and above. Such reaction chambers can be used to reduce the amount of reagents used and to allow multiple reactions to take place in a certain footprint (e.g. in a microfluidic cartridge).

Figure 16:
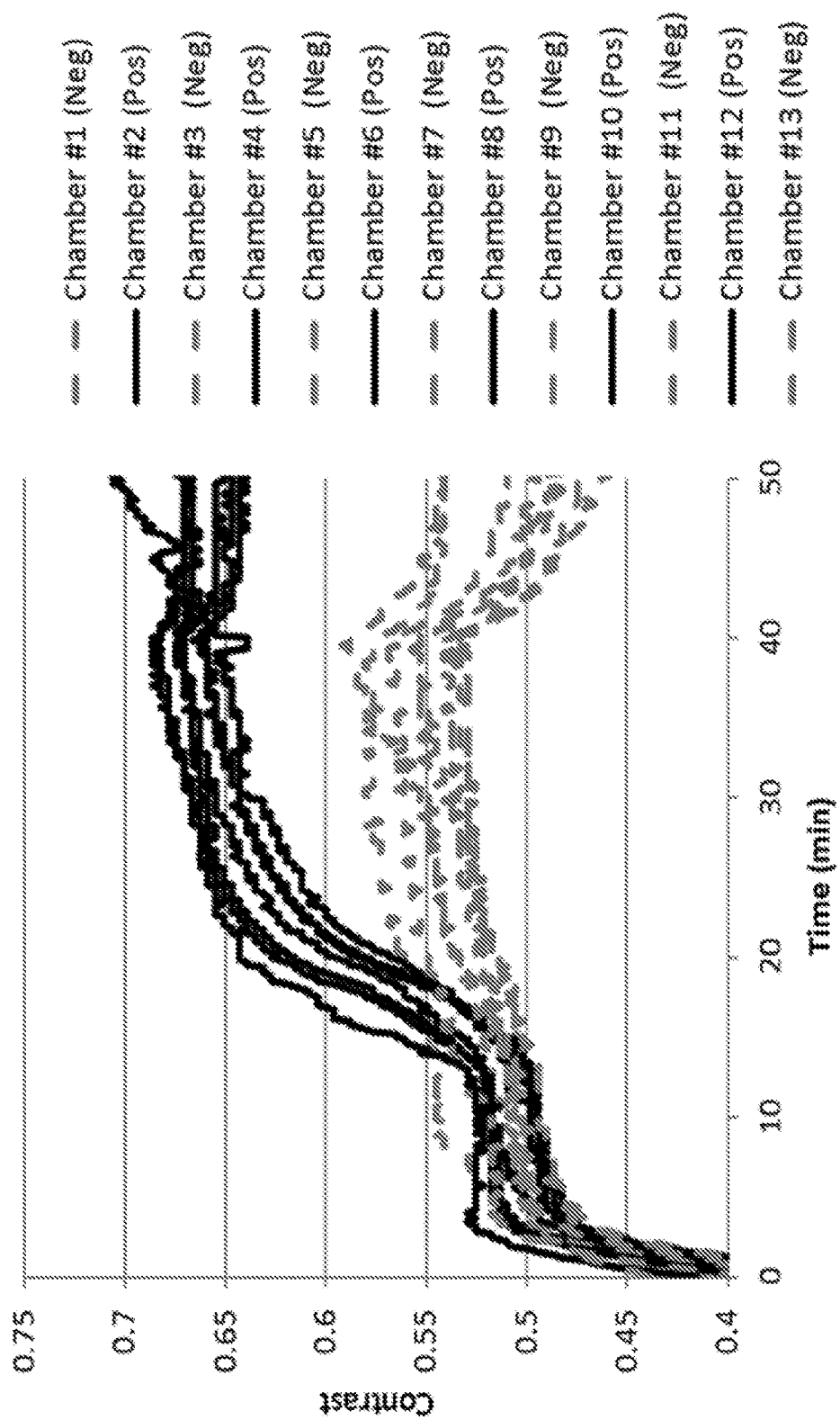
FIG. 16 provides LAMP amplification data from amplification in a device having a selective venting element.

Example 4: Detection of LAMP Amplification in Devices Having a Selective Venting Element LAMP reactions were performed as in Example 1 with 1.6 mM final Tris buffer concentration (buffer formulated to pH 8.8), 0.8 U/μl of Bst 2.0 DNA Polymerase, 5 ng lambda DNA template, and Phenol Red and Bromothymol Blue at 50 μM and 160 μM concentrations respectively. The solution was loaded into a fluidic device with reaction chambers consisting of a sample receiving input and a vent outlet. The vent outlet of each reaction chambers was sealed with a selective venting element, e.g., a self-sealing element. Alternating chambers had lambda primers dried in them. The sample receiving inputs are all connected to a bus channel connected to the device inlet. The reaction chambers were heated to 63° C. for 1 hour. The color change in the chambers was measured with a camera and the data is shown in FIG. 16.

Figure 12:
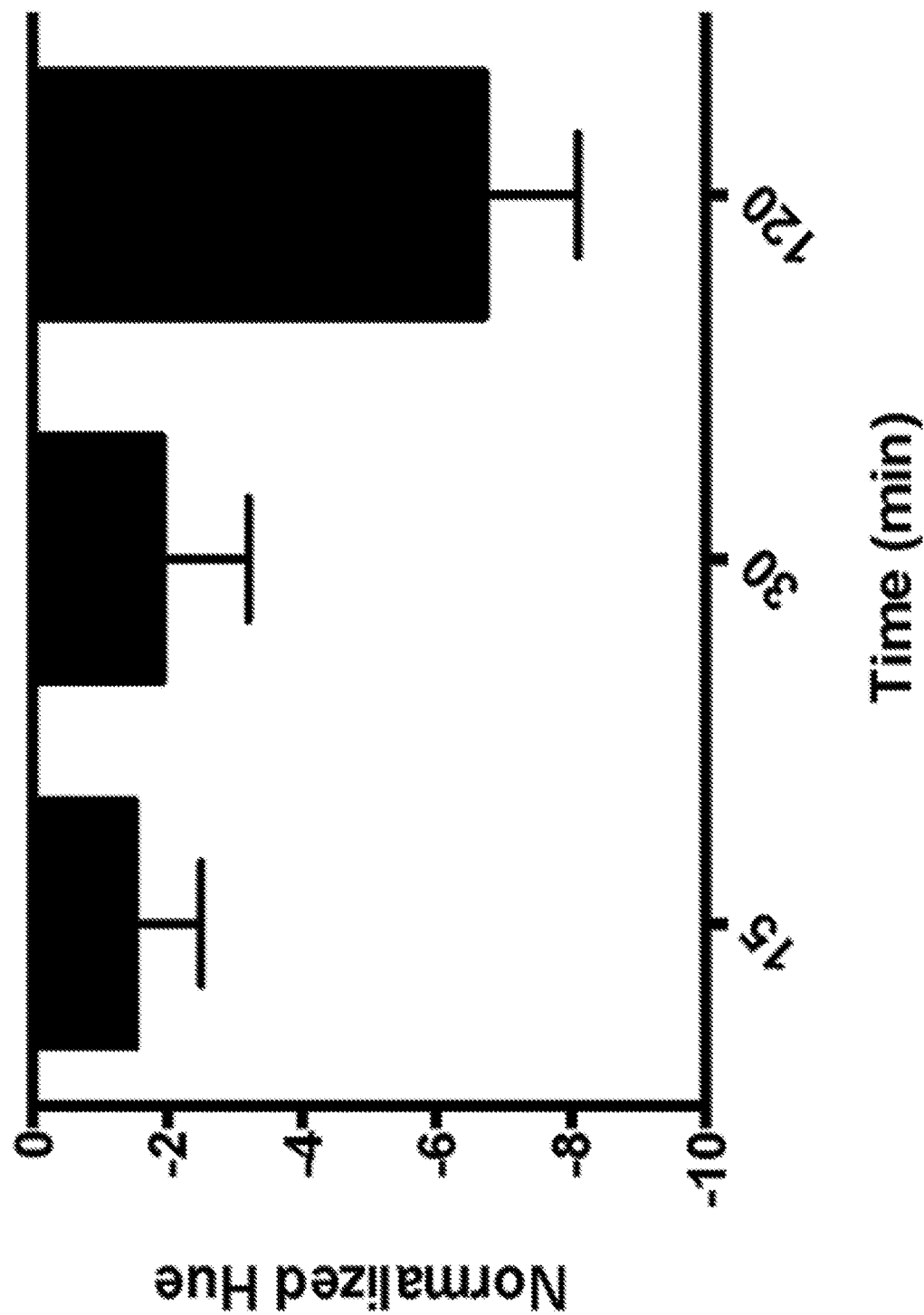
FIG. 12 shows the normalized hue values over time for SDA, according to an embodiment.

Example 5: Detection of Strand Displacement Amplification (SDA) Using a Visual Halochromic Agent SDA reactions were performed using a reaction mix comprising of: 1.3 mM final Tris buffer concentration (buffer formulated to pH 8.8), 10 mM $(NH_4)_2SO_4$, 50 mM KCl (adjusted to pH 8.5), 8 mM $MgSO_4$, 4.4 mM each dATP, dGTP, dTTP, 0.8 mM dCTP-aS (TriLink Biotechnologies), 0.1% v/v TWEEN® 20, 0.8 M Betaine, 0.32 U/μl Bst DNA polymerase (New England Biolabs), 0.2 U/uL BSoBI (New England Biolabs) and 0.2 mM Neutral Red halochromic agent. Primers designed for human BRCA1 (SDAf: SEQ ID NO: 17; SDAr: SEQ ID NO: 18; BF: SEQ ID NO: 19; BR: SEQ ID NO: 20) were added to the reaction at 0.5 μM final concentration each. 5 ng of HeLa gDNA was added to a final reaction volume of 25 μL and was held at 65° C. for different incubation times. A change in Normalized Hue value over time (FIG. 12) indicates that this visual detection chemistry works with SDA.

Example 6: Detection of PCR Amplification Using a Visual Halochromic Aunt

Figure 13:
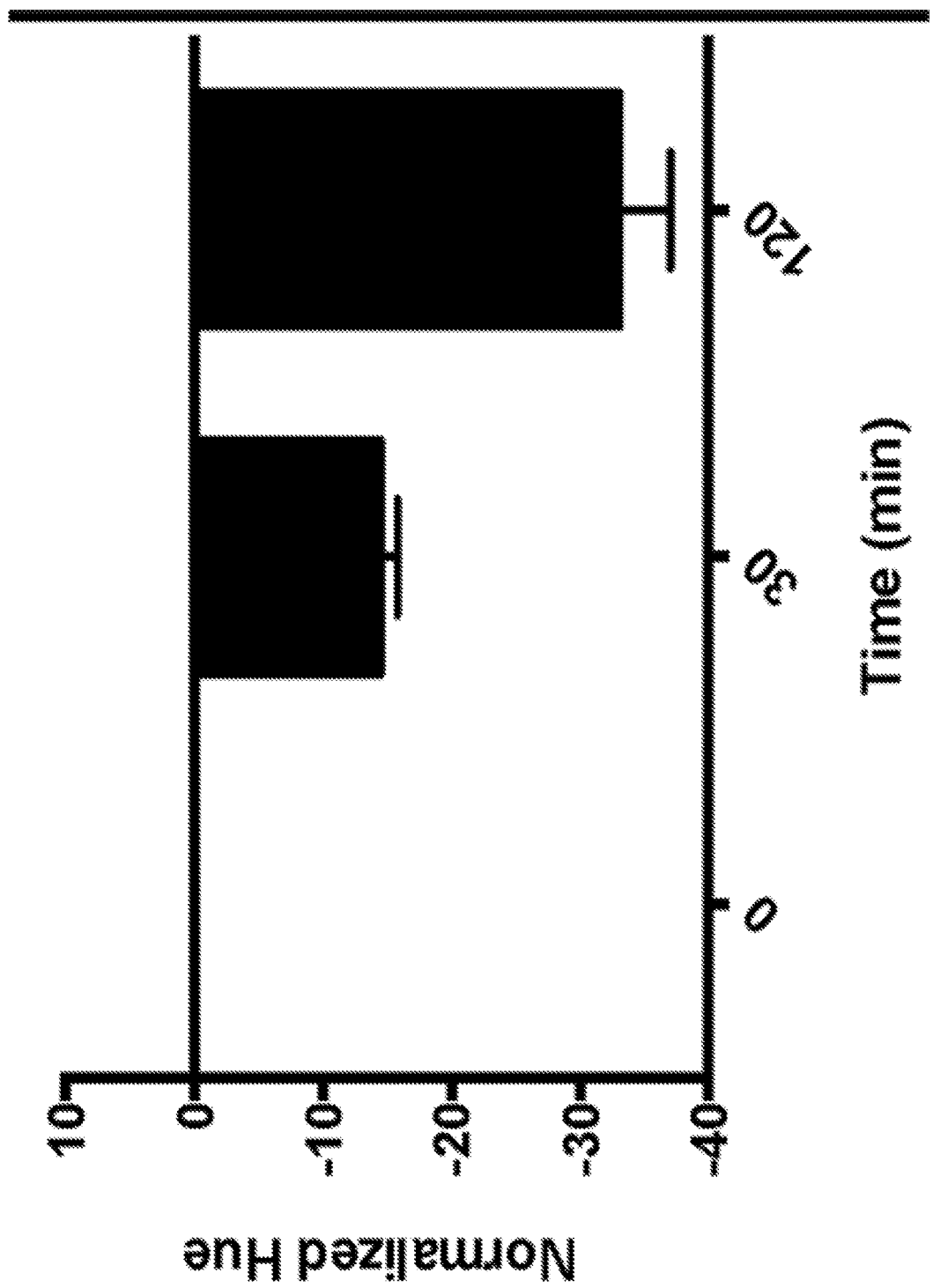
FIG. 13 shows the normalized hue values over time for PCR, according to an embodiment.

PCR reactions were performed using a reaction mix comprising of: 50 mM KCl and 2 mM $MgCl_2$ (pH adjusted 8.5), 0.5 mM each dNTP, 5U Taq DNA polymerase (New England Biolabs) and 0.2 mM Neutral Red halochromic agent. Total carry-over Tris-HCl concentration from enzyme storage buffer and primers (Forward: SEQ ID NO: 21; Reverse: SEQ ID NO: 22) was 1.15 mM in the final reaction mix. Primers were designed for Escherichia coli 16s rRNA gene and added to the reaction at 0.5 μM final concentration each. 10 ng of E. coli gDNA was added to a final reaction volume of 25 NL and was initially held at 95° C. hold for 2 min, followed by 50 cycles of 95° C. for 10 sec, 55° C. for 30 sec, 68° C. for 30 sec. A change in Normalized Hue value over time (FIG. 13) indicates that this visual detection chemistry works with PCR.

Figure 14A:
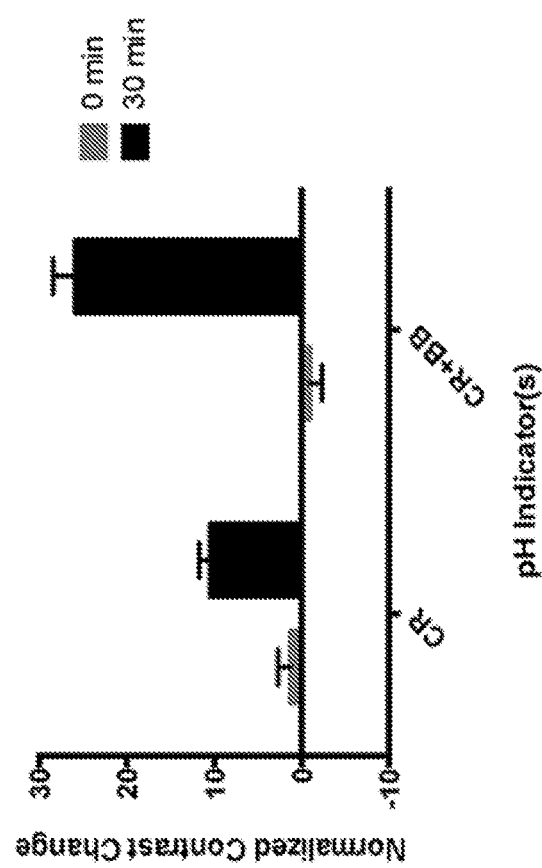
FIGS. 14A and 14B show the normalized contrast changes for amplification reactions using combinations of halochromic agents, according to an embodiment.
Figure 14B:
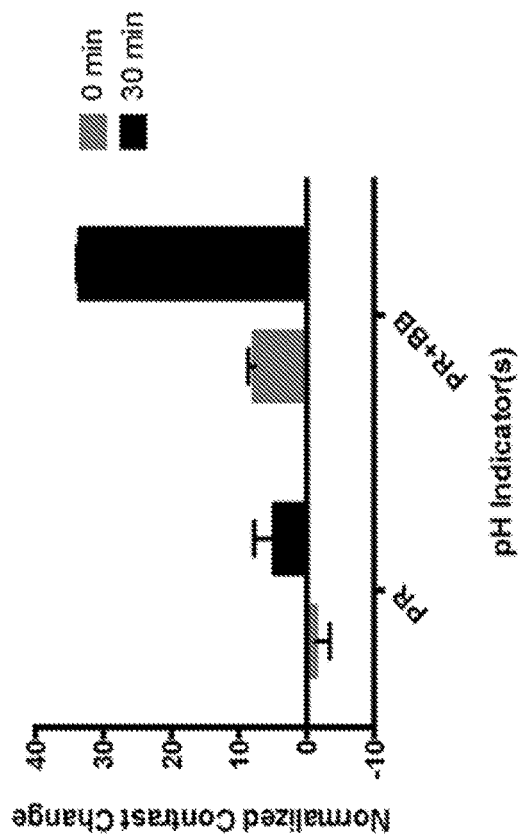

Example 7: Increase in Visual Detection Contrast with Combination of Halochromic Aunts LAMP reactions were performed as in Example 1 with 1.3 mM final Tris buffer concentration (buffer formulated to pH 8.8), 0.8 U/µl of Bst 2.0 DNA Polymerase and 5 ng lambda DNA template. The color change contrast was evaluated for Phenol Red at 50 µM concentration and combination of Phenol Red and Bromothymol Blue at 50 µM and 160 µM concentrations respectively (FIG. 14A). The color change contrast was also evaluated for Cresol Red at 260 µM concentration and combination of Cresol Red and Bromothymol Blue at 260 µM and 160 µM concentrations respectively (FIG. 14B). The contrast values were calculated from the RGB values of images of the reaction mix using the formula: 0.299R+0.587G+0.114B. The normalized contrast change was defined as the difference between positive and negative reaction contrast values normalized to the background. The increase in the normalized contrast change with the use of the halochromic agent combination demonstrates the utility of such combinations.

Figure 15:
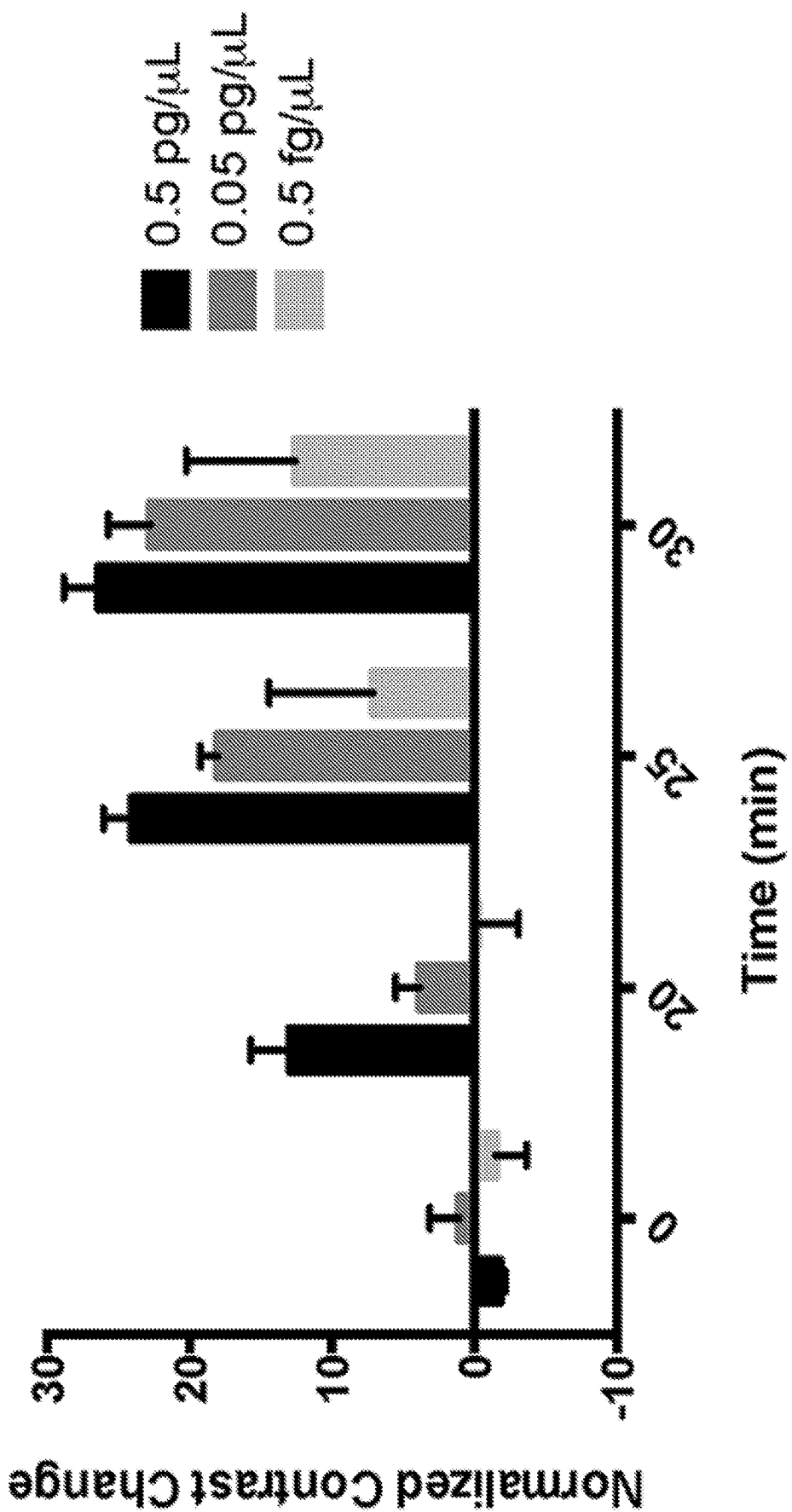
FIG. 15 shows the normalized contrast changes over time for different DNA template concentrations, according to an embodiment.

Example 8: Real-Time Color Monitoring of Amplification for Quantification Using Visual Halochromic Agents LAMP reactions were performed as in Example 1 with 1.3 mM final Tris buffer concentration (buffer formulated to pH 8.8), 0.8 U/µl of Bst 2.0 DNA Polymerase, Phenol Red and Bromothymol Blue at 50 µM and 160 µM concentrations respectively and varying lambda DNA template concentrations. Color change contrast was evaluated for lambda DNA target at 0.5 fg/µl, 0.05 pg/µl and 0.5 pg/µl final concentrations. The contrast values were calculated from the RGB values of images of the reaction mix as described in Example 5. The results (FIG. 15) indicate that the higher DNA concentrations led to a detectable change in visual contrast earlier than the lower DNA concentrations. Hence, we demonstrate the ability to distinguish between different target concentrations with the real-time color monitoring of this chemistry.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims.

The invention claimed is:

1. A biological sample assay optical property modifying device, the device comprising:
   a) a sample receiving cartridge comprising i) a sample inlet, ii) reaction chambers each comprising an optical property modifying reagent, and iii) one or more conduits operatively connecting the reaction chambers with the sample inlet;
   b) a substrate comprising:
      i) a heating element; and
      ii) a power source operatively coupled to the heating element; and
   c) an adhesive layer operatively connecting the sample receiving cartridge and the substrate, wherein the adhesive layer forms a wall of each of the reaction chambers, and wherein the adhesive layer comprises one or more adhesive.

2. The device according to claim 1, wherein each of the reaction chambers are microfluidic reaction chambers.

3. The device according to claim 1, further comprising a selective venting element forming a wall of each of the reaction chambers.

4. The device according to claim 3, wherein the selective venting element comprises a porous polymer matrix and a hydrogel having a passively tunable porosity.

5. The device according to claim 4, wherein the porous polymer matrix comprises polyethylene.

6. The device according to claim 4, wherein the hydrogel comprises carboxymethyl cellulose.

7. The device according to claim 1, wherein each of the reaction chambers comprises a first opening on a first side of the sample receiving cartridge and a second opening on a second side of the sample receiving cartridge, wherein the first side is opposite the second side and the adhesive layer seals each second opening.

8. The device according to claim 7, further comprising a selective venting element which seals each first opening.

9. The device according to claim 1, wherein the substrate is a printed circuit board.

10. The device according to claim 1, wherein the power source is a battery.

11. The device according to claim 1, wherein the substrate comprises a control unit.

12. The device according to claim 11, wherein the substrate comprises a sensor.

13. The device according to claim 12, wherein the control unit activates the heating element to heat a sample in the reaction chambers when the sensor detects the sample.

14. The device according to claim 12, wherein the substrate comprises a light source that emits light when the sensor detects the sample.

15. The device according to claim 11, wherein the control unit is configured to perform a colorimetric analysis of a sample in the reaction chambers.

16. The device according to claim 1, further comprising a housing.

17. The device according to claim 16, wherein the housing comprises a first portion and a second portion, wherein the second portion is mateable with the first portion to encapsulate the sample receiving cartridge, the substrate and the adhesive layer.

18. The device according to claim 16, wherein the housing has a volume of 300 $cm^3$ or less.

19. The device according to claim 1, wherein the device is a hand-held device.

20. The device according to claim 1, wherein the sample receiving cartridge is transparent.

21. The device according to claim 1, wherein the sample receiving cartridge comprises a polymeric material.

22. The device according to claim 21, wherein the polymeric material is polyethylene.

23. The device according to claim 1, wherein the adhesive layer is transparent.

24. The device according to claim 1, wherein the adhesive layer is reflective.

25. The device according to claim 1, wherein the adhesive layer comprises an acrylic adhesive.

26. The device according to claim 1, wherein the chambers each comprise a nucleic acid amplification composition.

27. The device according to claim 1, wherein the biological sample is a nucleic acid amplification sample.

28. The device according to claim 1, wherein the optical property modifying reagent is a halochromic reagent.

29. The device according to claim 1, wherein the adhesive layer has a thermal conductivity of conductivity of 0.1 W/m-K to 10 W/m-K.

30. The device according to claim 1, wherein the adhesive layer does not comprise an acid.

31. The device according to claim 1, wherein the adhesive layer is opaque and white.

32. The device according to claim 1, wherein the adhesive layer comprises a first layer laminated with a second layer.

33. The device according to claim 32, wherein the first layer does not comprise an acid.

34. The device according to claim 32, wherein the second layer is opaque and white.

35. The device according to claim 1, wherein the optical property modifying reagent is an enzyme-linked immunosorbent assay (ELISA) reagent.

36. The device according to claim 35, wherein the ELISA reagent is selected from the group consisting of alkaline phosphatase, horseradish peroxidase, β-galactosidase, BCIP/NBT (5-bromo-4-chloro-3-indolyl-phosphate/nitrobluetetrazolium), TMB (3,3', 5,5' tetramethylbenzidine), DAB (3,3', 4,4' diaminobenzidine), 4CN (4-chloro-1-naphthol), TMB (dual function substrate), ABTS (2,2'-azino-di [3-ethylbenzthiazoline] sulfonate), OPD (o-phenylenediamine), MUG (4-methylumbelliferyl galactoside), HPA (hydroxyphenylacetic acid), and HPPA (3-p-hydroxyphenylproprionic acid).

37. The device according to claim 1, wherein the heating element comprises two or more heat-generating reactants that produce heat when mixed with one another.

38. The device according to claim 1, wherein the adhesive layer is opaque and a color complementary to a reaction start color.

39. The device according to claim 1, wherein the device further comprises a housing, the housing comprising:
    a first portion and
    a second portion mated with the first portion,
    wherein the housing encapsulates the sample receiving cartridge, the substrate, and the adhesive layer and wherein the housing further comprises one or more inlet opening providing access to the sample inlet for a sample to be loaded into the sample receiving cartridge.

40. A method of modifying an optical property in a biological sample assay, the method comprising:
    a. transmitting a biological sample into the reaction chambers of the biological sample assay optical property modifying device of claim 1, thereby generating a reaction mixture;
    b. heating the reaction mixture with a heating element of a substrate of the device and thereby generating a reaction product, wherein the substrate further comprises a power source operatively coupled to the heating element; and
    c. reacting the reaction product with the optical property modifying reagent, wherein the reacting sufficiently modifies an optical property of the optical property modifying reagent to allow detection of the modified optical property.

41. The method according to claim 40, wherein the biological sample comprises a nucleic acid.

42. The method according to claim 41, wherein the reaction chambers further comprise an amplification composition.

43. The method according to claim 42, wherein the heating accelerates a nucleic acid amplification reaction comprising the nucleic acid and the amplification composition, the reaction generating an amplified nucleic acid and the reaction product, wherein the reaction product comprises a plurality of protons.

44. The method according to claim 40, wherein the reaction chambers are each microfluidic reaction chambers.

45. The method according to claim 40, wherein the optical property modifying device is a hand-held device.

46. The method according to claim 40, wherein the optical property modifying device comprises a housing having a volume of 300 cm$^3$ or less.

47. The method according to claim 40, wherein the transmitting the biological sample into the reaction chambers comprises flowing the sample through the sample inlet operatively connecting each of the reaction chambers.

48. The method according to claim 40, wherein the optical property modifying device further comprises a selective venting element, and the method further comprises containing the sample in the reaction chambers with the selective venting element.

49. The method according to claim 48, wherein transmitting a biological sample into the reaction chambers comprises flowing a gas through the selective venting element.

50. The method according to claim 49, wherein the gas is air.

51. The method according to claim 40, wherein heating the reaction mixture comprises flowing heat through the substrate operatively coupled to the heating element and to the reaction chambers of the optical property modifying device.

52. The method according to claim 51, wherein the substrate comprises a sensor, and wherein transmitting a biological sample into the reaction chambers comprises detecting the sample in the reaction chambers with the sensor.

53. The method according to claim 51, wherein the substrate comprises a light source, and wherein transmitting a biological sample into the sample receiving cartridge comprises activating the light source to emit light.

54. The method according to claim 51, wherein heating the reaction mixture comprises actuating printed circuitry on the substrate.

55. The method according to claim 51, heating the reaction mixture comprises flowing power from the power source operatively coupled to the heating element.

56. The method according to claim 51, wherein the substrate comprises a control unit, and wherein modifying an optical property of the biological sample comprises performing a colorimetric analysis of a sample in the reaction chambers with the control unit.

57. The method according to claim 40, wherein the optical property modifying device further comprises a housing comprising a first portion comprising a receptacle, and a second portion mateable with the first portion to encapsulate the sample receiving cartridge and the heating element, and wherein transmitting the biological sample into the reaction chambers comprises flowing the sample through the receptacle.

58. The method according to claim 40, further comprising performing a colorimetric analysis of the reaction product after reacting it with the optical property modifying reagent.

59. The method according to claim 58, wherein the sample receiving cartridge is transparent, and wherein performing a colorimetric analysis comprises detecting one or more characteristics of light transmitted through the sample receiving cartridge.

60. The method according to claim 40, further comprising performing a colorimetric analysis of the reaction product after reacting it with the optical property modifying reagent, wherein the adhesive layer is opaque white, and wherein performing the colorimetric analysis comprises visually inspecting the reaction chambers to detect a modified optical property.

61. The method according to claim 40, wherein each of the reaction chambers comprises a first opening on a first side of the sample receiving cartridge and a second opening on a second side of the sample receiving cartridge, wherein the first side is opposite the second side.

62. The method according to claim 61, wherein the adhesive layer seals each second opening, and wherein transmitting a biological sample into the reaction chambers comprises containing the sample in the reaction chambers with the adhesive layer.

63. The method according to claim 40, wherein the adhesive layer is transparent and wherein the detecting comprises visually inspecting light passing through the adhesive layer.

64. The method according to claim 40, wherein the adhesive layer is reflective and wherein the detecting comprises visually inspecting light reflecting from the adhesive layer.

65. The method according to claim 40, wherein the adhesive layer comprises an acrylic adhesive.

66. The method according to claim 40, wherein the optical property modifying reagent is a halochromic reagent.

67. The method according to claim 40, wherein the adhesive layer has a thermal conductivity of 0.1 W/m-K to 10 W/m-K.

68. The method according to claim 40, wherein the adhesive layer does not comprise an acid.

69. The method according to claim 40, wherein the adhesive layer is opaque and white.

70. The method according to claim 40, wherein the adhesive layer comprises a first layer laminated with a second layer.

71. The method according to claim 70, wherein the first layer does not comprise an acid.

72. The method according to claim 70, wherein the second layer is opaque and white.

73. The method according to claim 40 wherein the optical property modifying reagent is an enzyme-linked immunosorbent assay (ELISA) reagent.

74. The method according to claim 73, wherein the ELISA reagent is selected from the group consisting of alkaline phosphatase, horseradish peroxidase, β-galactosidase, BCIP/NBT (5-bromo-4-chloro-3-indolyl-phosphate/nitrobluetetrazolium), TMB (3,3', 5,5' tetramethylbenzidine), DAB (3,3', 4,4' diaminobenzidine), 4CN (4-chloro-1-naphthol), TMB (dual function substrate), ABTS (2,2'-azino-di [3-ethylbenzthiazoline] sulfonate), OPD (o-phenylenediamine), MUG (4-methylumbelliferyl galactoside), HPA (hydroxyphenylacetic acid), and HPPA (3-p-hydroxyphenylproprionic acid).

75. The method according to claim 40, wherein the reacting sufficiently modifies an optical property of the optical property modifying reagent to allow detection of the modified optical property by an un-assisted human eye.

76. The method according to claim 40, wherein the heating element comprises one or more heat-generating reactants that produce heat when mixed with one another or with the reaction mixture and wherein heating the reaction mixture comprises mixing the one or more heat-generating reactants with one another or with the reaction mixture.

77. The method according to claim 40, wherein the adhesive layer is opaque and a color complementary to a reaction start color.

78. A method of modifying an optical property with the biological sample assay optical property modifying device of claim 1, the method comprising:
  a. generating a reaction product from a biological sample;
  b. reacting the reaction product with the optical property modifying reagent, wherein the reacting sufficiently modifies an optical property of the optical property modifying reagent to allow detection of the modified optical property.

79. The method according to claim 78, wherein the reacting sufficiently modifies an optical property of the optical property modifying reagent to allow detection of the modified optical property by an un-assisted human eye.

80. A method of manufacturing the biological sample assay optical property modifying device of claim 1, the method comprising:
  operatively coupling the sample receiving cartridge and the substrate with the adhesive layer.

81. The method of manufacturing according to claim 80, wherein the adhesive layer comprises a first side and a second side opposite the first side, and wherein operatively coupling the sample receiving cartridge and substrate comprises adhesively attaching the sample receiving cartridge to the first side and the substrate to the second side.

82. The method of manufacturing according to claim 80, wherein the substrate is a printed circuit board.

83. The method according to claim 80, wherein the method comprises a step of inserting the optical property modifying reagent into each the reaction chambers and storing the optical property modifying reagent therein while retaining functionality of the optical property modifying reagent.

* * * * *